US012220400B2

(12) United States Patent
Vidyasagar et al.

(10) Patent No.: US 12,220,400 B2
(45) Date of Patent: Feb. 11, 2025

(54) AMINO ACID COMPOSITIONS AND METHODS FOR TREATING CYSTIC FIBROSIS

(71) Applicant: UNIVERSITY OF FLORIDA RESEARCH FOUNDATION, INCORPORATED, Gainesville, FL (US)

(72) Inventors: Sadasivan Vidyasagar, Gainesville, FL (US); Astrid Grosche, Gainesville, FL (US); Xiaodong Xu, Gainesville, FL (US); Shanshan Lin, Gainesville, FL (US); Sreekala Prabhakaran, Gainesville, FL (US)

(73) Assignees: AmiLyfe, LLC, Norwood, MA (US); University of Florida Research Foundation, Incorporated, Gainesville, FL (US)

( * ) Notice: Subject to any disclaimer, the term of this patent is extended or adjusted under 35 U.S.C. 154(b) by 889 days.

(21) Appl. No.: 17/289,374

(22) PCT Filed: Oct. 30, 2019

(86) PCT No.: PCT/US2019/058954
§ 371 (c)(1),
(2) Date: Apr. 28, 2021

(87) PCT Pub. No.: WO2020/092639
PCT Pub. Date: May 7, 2020

(65) Prior Publication Data
US 2021/0393584 A1 Dec. 23, 2021

Related U.S. Application Data

(60) Provisional application No. 62/752,847, filed on Oct. 30, 2018.

(51) Int. Cl.
*A61K 31/401* (2006.01)
*A61K 31/198* (2006.01)
*A61K 31/47* (2006.01)
*A61K 45/06* (2006.01)
*A61P 11/00* (2006.01)

(52) U.S. Cl.
CPC .......... *A61K 31/401* (2013.01); *A61K 31/198* (2013.01); *A61K 31/47* (2013.01); *A61K 45/06* (2013.01); *A61P 11/00* (2018.01)

(58) Field of Classification Search
CPC ........ A61K 31/198; A61K 31/47; A61P 11/00
See application file for complete search history.

(56) References Cited

U.S. PATENT DOCUMENTS

| 8,389,736 | B2 | 3/2013 | Kurth et al. | |
|---|---|---|---|---|
| 9,132,123 | B2 | 9/2015 | Maiuri et al. | |
| 9,901,559 | B2 * | 2/2018 | Conti | A61K 31/405 |
| 2004/0192756 | A1 * | 9/2004 | Conti | A61P 17/02 |
| | | | | 514/567 |
| 2004/0253319 | A1 | 12/2004 | Netke et al. | |
| 2005/0020656 | A1 * | 1/2005 | Horie | A61P 13/12 |
| | | | | 514/400 |
| 2005/0129787 | A1 | 6/2005 | Murad | |
| 2013/0085170 | A1 | 4/2013 | Conti et al. | |

FOREIGN PATENT DOCUMENTS

| WO | 2002098405 A1 | 12/2002 | |
|---|---|---|---|
| WO | 2004110383 A2 | 12/2004 | |
| WO | 2016191263 A1 | 12/2016 | |
| WO | WO2016/191263 | * 12/2016 | ............. A61K 38/08 |
| WO | 2017223188 A1 | 12/2017 | |
| WO | WO2017/223188 | * 12/2017 | ............. A61K 38/08 |

OTHER PUBLICATIONS

Extended EP Search Report to corresponding EP Application No. 19879930.6 mailed Jul. 6, 2022 (12 pages).
Mizuguchi Shinjiro et al., "S-allyl cysteine attenuated CC14-induced oxidative stress and pulmonary fibrosis in rats," Biofactors, Oxford University Press, Oxford, GB, vol. 26, No. 1, pp. 81-92 (2006).
International Search Report to corresponding International Application No. PCT/US19/58954 mailed Jan. 22, 2020 (4 pages).

* cited by examiner

*Primary Examiner* — Paul V Ward
(74) *Attorney, Agent, or Firm* — Greenberg Traurig, LLP

(57) ABSTRACT

Provided herein are amino acid compositions useful for increasing the translocation of the cystic fibrosis transmembrane conductance (CFTR) protein from the cytoplasm to the plasma membrane, particularly in epithelial cells. Methods for increasing the concentration of CFTR in the plasma membrane, increasing chloride ion transport, and increasing water transport are also provided. These compositions and methods are useful in treating cystic fibrosis in subjects bearing one or more mutations in the CFTR protein. Use of these compositions for the treatment of cystic fibrosis and in the preparation of a medicament for the treatment of cystic fibrosis are also encompassed herein.

24 Claims, 18 Drawing Sheets

Specification includes a Sequence Listing.

AMINO ACID COMPOSITIONS AND METHODS FOR TREATING CYSTIC FIBROSIS

RELATED APPLICATIONS

This application is a U.S. National Phase Application of International Application No. PCT/US19/58954, which claims priority of U.S. Provisional Application No. 62/752,847 filed Oct. 30, 2018, the entirety of both applications are incorporated herein by reference for all purposes.

SEQUENCE LISTING

The instant application contains a Sequence Listing which has been submitted electronically in ASCII format and is hereby incorporated by reference in its entirety. Said ASCII copy, created on Oct. 25, 2019, is named 174821-013301PCT_SL.txt and is 25,987 bytes in size.

FIELD OF INVENTION

Amino acid compositions useful for increasing the translocation of the cystic fibrosis transmembrane conductance (CFTR) protein from the cytoplasm to the plasma membrane are described herein. Methods for increasing the concentration of CFTR in the plasma membrane, increasing chloride ion transport, and increasing water transport are also presented. Compositions and methods described herein are useful for treating cystic fibrosis in subjects bearing one or more mutations in the CFTR protein. Use of these compositions for the treatment of cystic fibrosis and in the preparation of a medicament for the treatment of cystic fibrosis are also encompassed herein.

BACKGROUND OF THE INVENTION

Cystic fibrosis (CF) is a hereditary recessive disease caused by reduction or lack of CFTR synthesis, protein misfolding and/or channel dysfunction resulting in decreased chloride secretion, increased sodium absorption (ENaC), and impaired fluid homeostasis in airways, intestinal and pancreas epithelial cells. CF is the most common life-limiting genetic disorder that can affect the lungs, liver, pancreas, kidneys, and intestines. Cystic fibrosis is inherited in an autosomal recessive manner, where each parent carries a mutation in at least one allele of the gene encoding the cystic fibrosis transmembrane conductance (CFTR) protein, leading to one out of four progeny carrying two mutated copies (e.g., alleles) of the CFTR gene. Thus, more than 75% of patients are diagnosed with cystic fibrosis by age 2.[1] While the life expectancy of people living with cystic fibrosis has increased in recent years, the median age of survival is currently around 40 years. Current therapies often involve burdensome supportive treatments designed to manage the increased risk of lung infection and poor nutritional status. In addition, while small molecule therapies that treat the underlying genetic cause of CF have recently been approved, these therapies are minimally effective against the most common CFTR mutation, Phe508del, and are cost prohibitive at upwards of $300,000 annually per patient.[2]

While over 2,000 CFTR mutations have been identified in patients suffering from cystic fibrosis, the vast majority of cystic fibrosis diagnoses exhibit one or more of only a handful of mutations.[3] The most common mutation, Phe508del, is a deletion of 3 nucleotides, resulting in the loss of a single codon for the amino acid phenylalanine (three letter code: Phe, single letter code: F). This mutation results in defective CFTR protein processing (e.g., folding and trafficking to the plasma membrane), resulting in little to no membrane expression of CFTR, a chloride ion transporter protein involved in ion and water transport across the cell membrane. In addition, the small amount of Phe508del CFTR that successfully translocates to the plasma membrane is often functionally defective, as characterized by impaired chloride ion transport. In general, CFTR mutations lead to the dysregulation of the ion gradient across membranes, resulting in reduced osmotic pressure for water to flow out of the epithelial cells and manifestation of a thick mucus layer that covers the cells. The thick, nutrient rich mucus serves as an optimal environment for the trapping and growth of bacteria, such as *Pseudomonas aeruginosa* and *Staphylococcus aureus*, that lead to persistent infection that is often unresponsive to antibiotics. In addition, many CF patients also develop other lung diseases, such as bronchopulmonary aspergilliosis and bronchiectasis, leading to increased morbidity and mortality.

While targeted therapies for cystic fibrosis caused by specific mutations in CFTR have been developed, many are only efficacious in patients with certain CFTR mutations, and adverse side effects have been reported.[2] One example is ivacaftor (VX-770, KAYLDECO™), a small molecule potentiator of CFTR,[4] as described in U.S. Patent Application Publication US 2014/0221424 and International Patent Application Number PCT/US2015/036691. However, ivacaftor is directed to the treatment of CF in patients with the missense mutation Gly551Asp (G551D) on at least one allele of the CFTR gene, which encompasses around 4 to 5% of patients suffering from CF.[5] There is a clear, unmet need for therapies directed toward the treatment of cystic fibrosis, particularly in patients harboring the most prevalent CFTR mutation, Phe508del CFTR.

BRIEF DESCRIPTION OF THE DRAWINGS

FIG. 7A shows the benzamil insensitive current (anion current) of CF cells bathed in vehicle was significantly lower compared to normal HBECs, but CF-5AA-3 increased the anion current by a factor of >10 (n=4). FIG. 7B shows the bumetanide sensitive current (chloride current) was significantly higher in CF cells bathed in CF-5AA-3 compared to vehicle (n=4), but it did not reach the value of normal HBECs. FIGS. 7C, 7D, 7E, and 7F: show that CF cells bathed in CF-5AA-3 had a significantly higher anion peak current (FIG. 7E) and total chloride secretion (FIG. 7F), and stimulation with FSK and GLPG1837 did not contribute to the increased values in the presence of AA (FIGS. 7C, D).

FIG. 8A shows that CF cells bathed in vehicle or CF-5AA-3 had a significantly higher ENaC activity (benzamil sensitive current) compared to normal HBECs, but the ENaC activity was slightly lower in CF cells bathed in CF-5AA-3 compared to vehicle (n=4). FIG. 8B shows similarly, that sodium absorption was significantly increased in CF cells with a moderate lower sodium absorption in CF cells bathed in CF-5AA-3 (n=7).

SUMMARY OF THE INVENTION

Figure 1A:
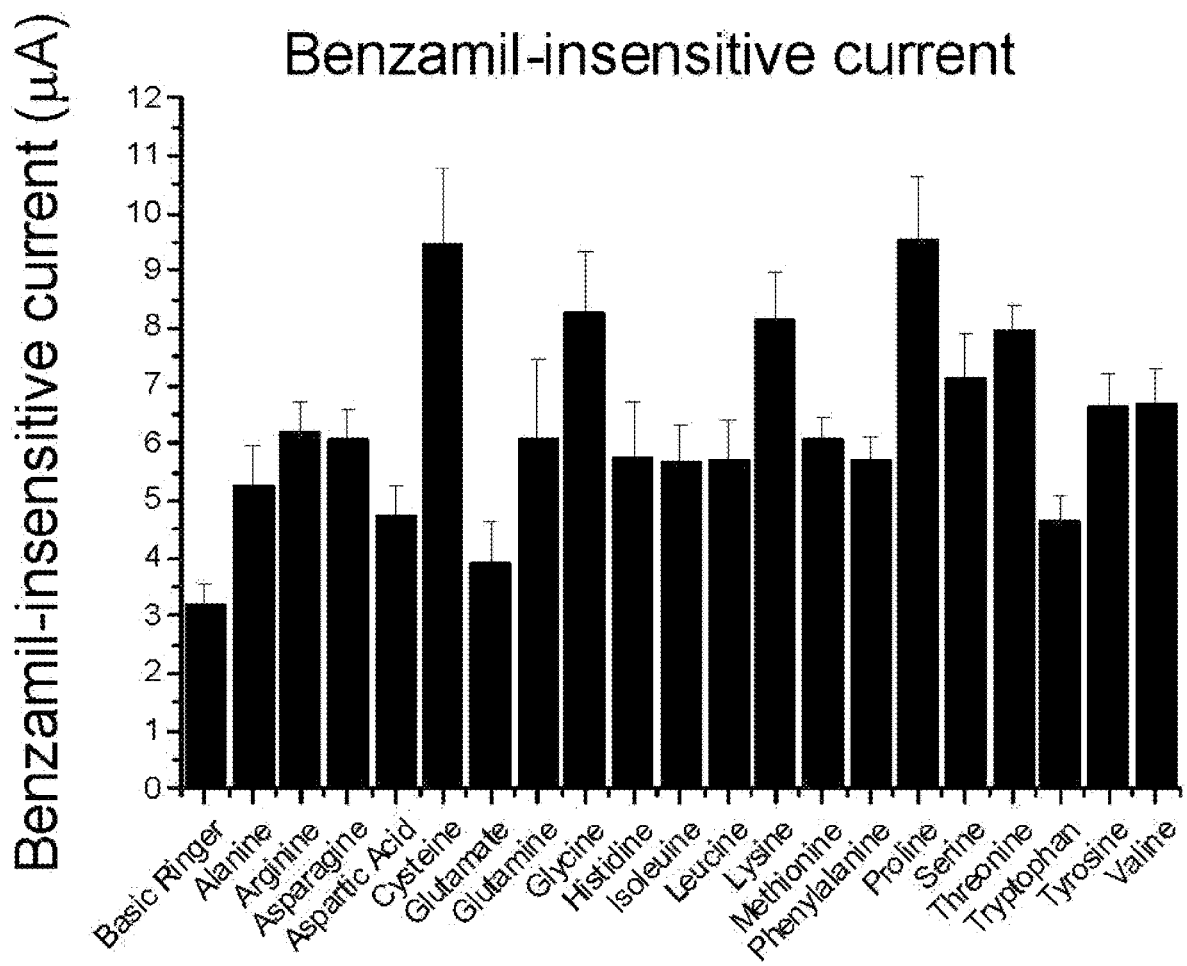
FIG. 1A shows a graph of benzamil-insensitive current (μA) without C18 for a control (Basic Ringers) solution and for various individual amino acids (AA) (n=4).

Covered embodiments are defined by the claims, not this summary. This summary is a high-level overview of various aspects and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

The present disclosure recognizes the need to provide more cost-effective and efficacious treatment options for cystic fibrosis patients. The amino acid compositions described herein may be particularly useful in treating CF patients carrying at least one Phe508del mutation on an allele of the CFTR gene. When the CFTR gene is homozygous for the Phe508del mutation, little to no CFTR is trafficked to the plasma membrane, rendering treatment with a CFTR potentiator (e.g., ivacaftor), which increases the function of CFTR present in the plasma membrane, virtually ineffective. The present disclosure provides compositions shown to increase the translocation of both wild-type and Phe508del CFTR proteins from the cytoplasm to the plasma membrane. In particular, the compositions described herein are particularly effective at increasing the number of mutant CFTR proteins on the plasma membrane. In addition, methods for treating diseases in which CFTR dysfunction is present (e.g., cystic fibrosis) are also provided herein.

Formulation—Amino Acids

In a first aspect, the present invention provides a formulation comprising: cysteine and proline as free amino acids and at least one additional free amino acid selected from the group consisting of glycine, tyrosine and lysine, with the proviso that at least one of the free amino acids is an L-amino acid.

In one embodiment, the free amino acids are L-amino acids.

In one embodiment, the formulation does not comprise free amino acids other than cysteine, proline and at least one additional amino acid selected from the group consisting of glycine, tyrosine and lysine.

In one embodiment, the formulation consists essentially of cysteine and proline as free amino acids and one or more additional free amino acids selected from the group consisting of glycine, tyrosine and lysine, with the proviso that at least one of the free amino acids is an L-amino acid.

In one embodiment, the formulation consists of cysteine and proline as free amino acids and one or more additional free amino acids selected from the group consisting of glycine, tyrosine and lysine, with the proviso that at least one of the free amino acids is an L-amino acid.

In one embodiment, the formulation comprises, consists, or consists essentially of cysteine, proline and glycine as free amino acids and optionally one or more additional free amino acids selected from the group consisting of tyrosine and lysine, with the proviso that at least one of the free amino acids is an L-amino acid.

In one embodiment, the formulation comprises, consists, or consists essentially of cysteine, proline and glycine as free amino acids, with the proviso that at least one of the free amino acids is an L-amino acid, and no other free amino acids.

In one embodiment, the formulation comprises, consists, or consists essentially of cysteine, proline and tyrosine as free amino acids and optionally one or more additional free amino acids selected from the group consisting of glycine and lysine, with the proviso that at least one of the free amino acids is an L-amino acid.

In one embodiment, the formulation comprises, consists, or consists essentially of cysteine, proline and tyrosine as free amino acids, with the proviso that at least one of the free amino acids is an L-amino acid, and no other free amino acids.

In one embodiment, the formulation comprises, consists, or consists essentially of cysteine, proline and lysine as free amino acids and optionally one or more additional free amino acids selected from the group consisting of glycine and tyrosine, with the proviso that at least one of the free amino acids is an L-amino acid.

In one embodiment, the formulation comprises, consists, or consists essentially of cysteine, proline and lysine as free amino acids, with the proviso that at least one of the free amino acids is an L-amino acid, and no other free amino acids.

In one embodiment, the formulation comprises, consists, or consists essentially of cysteine, proline, glycine and tyrosine as free amino acids and optionally additionally comprises lysine as a free amino acid, with the proviso that at least one of the free amino acids is an L-amino acid.

In one embodiment, the formulation comprises, consists or consists essentially of cysteine, proline, glycine and tyrosine as free amino acids, with the proviso that at least one of the free amino acids is an L-amino acid, and no other free amino acids.

In one embodiment, the formulation comprises, consists, or consists essentially of cysteine, proline, glycine and lysine as free amino acids and optionally additionally comprises tyrosine as a free amino acid, with the proviso that at least one of the free amino acids is an L-amino acid.

In one embodiment, the formulation comprises, consists, or consists essentially of cysteine, proline, glycine and lysine as free amino acids, with the proviso that at least one of the free amino acids is an L-amino acid, and no other free amino acids.

In one embodiment, the formulation comprises, consists, or consists essentially of cysteine, proline, lysine and tyrosine as free amino acids and optionally additionally comprises glycine as a free amino acid, with the proviso that at least one of the free amino acids is an L-amino acid.

In one embodiment, the formulation comprises, consists, or consists essentially of cysteine, proline, lysine and tyrosine as free amino acids, with the proviso that at least one of the free amino acids is an L-amino acid, and no other free amino acids.

In one embodiment, the formulation comprises, consists, or consists essentially of cysteine, proline, glycine, tyrosine and lysine as free amino acids with the proviso that at least one of the free amino acids is an L-amino acid.

In one embodiment, the formulation comprises no other free amino acids.

In a second aspect, the present invention provides a formulation comprising: cysteine and proline as free amino acids and at least one additional free amino acid selected from the group consisting of glycine, tyrosine, lysine, and valine, with the proviso that at least one of the free amino acids is an L-amino acid.

In one embodiment of the second aspect, the free amino acids are L-amino acids.

In one embodiment of the second aspect, the formulation does not comprise free amino acids other than cysteine, proline and at least one additional amino acid selected from the group consisting of glycine, tyrosine, lysine, and valine.

In one embodiment of the second aspect, the formulation comprises, consists, or consists essentially of cysteine, proline, and valine as free amino acids with the proviso that at least one of the free amino acids is an L-amino acid.

In one embodiment of the second aspect, the formulation comprises, consists, or consists essentially of cysteine, proline, valine, and glycine as free amino acids, with the proviso that at least one of the free amino acids is an L-amino acid.

In one embodiment of the second aspect, the formulation comprises, consists, or consists essentially of cysteine, proline, valine, and tyrosine as free amino acids, with the proviso that at least one of the free amino acids is an L-amino acid.

In one embodiment, any one of the formulations of the second aspect comprises no other free amino acids.

Formulation—Excipients Etc.

In one embodiment, the formulation further comprises water.

In one embodiment, the formulation is a pharmaceutical formulation.

In one embodiment, the formulation further comprises a pharmaceutically acceptable carrier, buffer, electrolyte, adjuvant, or excipient.

In one embodiment, the formulation is sterile.

In one embodiment, the formulation is formulated for administration by an enteral, pulmonary, inhalation, intranasal, or sublingual route.

In one embodiment, in each free amino acid is present in a therapeutically effective amount.

Therapeutic Methods

In a further aspect, the present invention provides a formulation as described hereinabove, for use as a medicament.

In one embodiment of the invention, a formulation as described hereinabove is for use in the treatment of cystic fibrosis.

The invention also provides the use of a formulation as described hereinabove, in the manufacture of a medicament for the treatment of cystic fibrosis.

In a further aspect, the present invention provides a method for treating a subject afflicted with cystic fibrosis, the method comprising administering to the subject afflicted with cystic fibrosis the formulation as herein above described, wherein the administering reduces at least one symptom of cystic fibrosis.

In one embodiment, the subject afflicted with cystic fibrosis expresses wild-type CFTR. In one embodiment, the subject has a mutation in the CFTR gene. In one embodiment, the subject expresses wild-type CFTR and mutant CFTR. In one embodiment, the subject is afflicted with cystic fibrosis in which a CFTR protein that is at least 90%, at least 95%, at least 98%, at least 99%, or at least 99.5% identical to the amino acid sequence of wild-type CFTR is present, wherein the wild-type CFTR sequence comprises SEQ ID NO: 1. In one embodiment, the mutation in the CFTR comprises Gly542X, Gly551Asp, Arg553X, Arg117His, 120del23, Phe508del, or a combination thereof, wherein X is any amino acid. In one embodiment, the CFTR is a Phe508del CFTR mutant.

In one embodiment, the formulation as described herein above is used in combination with an additional therapeutic agent.

In one embodiment, the additional therapeutic agent comprises at least one of a small molecule drug, protein drug, nucleic acid drug, or combination thereof. In one embodiment, the additional therapeutic agent is at least one of a CFTR potentiator, CFTR corrector, CFTR read-through agent, or a combination thereof. In one embodiment, the additional therapeutic agent is a CFTR potentiator. In one embodiment, the CFTR potentiator is ivacaftor.

Further Aspects of the Invention

In a further aspect of the invention is provided a kit comprising: a pharmaceutical formulation as described hereinabove; and instructions for administering to a subject or contacting a biological sample with the formulation.

In a further aspect of the invention is provided a method for increasing the number of cystic fibrosis transmembrane conductance regulator (CFTR) proteins present on the plasma membrane of at least one cell, the method comprising: contacting the at least one cell with an effective amount of the pharmaceutical formulation as described hereinabove, wherein the contacting promotes at least one of folding of CFTR or transport of CFTR to the plasma membrane, thereby increasing the number of CFTR proteins present on the plasma membrane of the cell.

In one embodiment, the number of wild-type CFTR proteins on the plasma membrane increases. In one embodiment, the number of mutant CFTR proteins on the plasma membrane increases. In one embodiment, the number of CFTR proteins that are at least 90%, at least 95%, at least 98%, at least 99%, or at least 99.5% identical to the amino acid sequence of wild-type CFTR on the plasma membrane increases, wherein the wild-type CFTR comprises SEQ ID NO: 1. In one embodiment, one or more of the CFTR proteins comprise Gly542X, Gly551Asp, Arg553X, Arg117His, 120del23, Phe508del, or a combination thereof, wherein X is any amino acid. In one embodiment, one or more of the CFTR proteins comprise the Phe508del mutation. In one embodiment, increasing the number of CFTR proteins present on the plasma membrane of the cell is detected by increased chloride ion export from the cell. In one embodiment, increasing the number of CFTR proteins present on the plasma membrane of the cell is associated with increased water export from the cell. In one embodiment, the cell is an epithelial cell. In one embodiment, the epithelial cell is a lung epithelial cell. In one embodiment, the lung epithelial cell is a bronchial epithelial cell. In one embodiment, the bronchial epithelial cell is isolated from a subject afflicted with cystic fibrosis.

In a particular aspect, a pharmaceutical formulation is presented comprising: a therapeutically effective amount of cysteine and proline as free amino acids and a therapeutically effective amount of at least one additional free amino acid consisting of glycine, tyrosine or lysine, with the proviso that at least one of the free amino acids is an L-amino acid, wherein the pharmaceutical formulation consists essentially of cysteine, proline, and the at least one additional free amino acid.

In a particular embodiment of the pharmaceutical formulation, the free amino acids are L-amino acids. In another particular embodiment, the pharmaceutical formulation further comprises water. In another particular embodiment, the pharmaceutical formulation further comprises a pharmaceutically acceptable carrier, buffer, electrolyte, adjuvant, or excipient. In another particular embodiment, the pharmaceutical formulation is sterile. In another particular embodiment, the pharmaceutical formulation is formulated for administration by an enteral, pulmonary, inhalation, intranasal, or sublingual route.

In a particular embodiment of the pharmaceutical formulation, the pharmaceutical formulation comprises, consists essentially of, or consists of a therapeutically effective amount of cysteine and proline as free amino acids and a therapeutically effective amount of at least one additional free amino acid consisting of glycine, tyrosine or lysine, and no other free amino acids. Combinations of the recited amino acids include, for example: cysteine, proline, and glycine; cysteine, proline, and tyrosine; cysteine, proline, and lysine; cysteine, proline, glycine, and tyrosine; cysteine, proline, glycine, and lysine; cysteine, proline, tyrosine, and lysine; and cysteine, proline, glycine, tyrosine, and lysine.

In another particular embodiment of the pharmaceutical formulation, the pharmaceutical formulation comprises, consists essentially of, or consists of a therapeutically effective amount of cysteine and proline as free amino acids and a therapeutically effective amount of at least one additional free amino acid consisting of glycine, tyrosine, lysine, or valine, and no other free amino acids. Combinations of the recited amino acids include, for example: cysteine, proline, and valine; cysteine, proline, valine, and glycine; and cysteine, proline, valine, and tyrosine.

In another particular embodiment of the pharmaceutical formulation, the pharmaceutical formulation comprises a therapeutically effective amount of each of cysteine, proline, glycine, tyrosine and lysine, as free amino acids and no other free amino acids. In another particular embodiment of the pharmaceutical formulation, the pharmaceutical formulation consists essentially of or consists of a therapeutically effective amount of each of cysteine, proline, glycine, tyrosine and lysine, as free amino acids.

In a particular embodiment, the pharmaceutical formulation is for use in therapy. In a more particular embodiment, the pharmaceutical formulation is for use in the treatment of cystic fibrosis. In another particular embodiment, the pharmaceutical formulation is used forth manufacture of a medicament for treatment of cystic fibrosis.

In a further aspect, a method for treating a subject afflicted with cystic fibrosis is presented, the method comprising administering to the subject afflicted with cystic fibrosis a pharmaceutical formulation described herein, wherein the administering reduces at least one symptom of cystic fibrosis. In a particular embodiment of the method, the subject expresses wild-type CFTR. In another particular embodiment, the subject has a mutation in the CFTR gene. In another particular embodiment, the subject expresses wild-type CFTR and mutant CFTR. In another particular embodiment, the subject is afflicted with cystic fibrosis in which a CFTR protein that is at least 90%, at least 95%, at least 98%, at least 99%, or at least 99.5% identical to the amino acid sequence of wild-type CFTR is present, wherein the wild-type CFTR sequence comprises SEQ ID NO: 1. In another particular embodiment, the mutation in the CFTR comprises Gly542X, Gly551Asp, Arg553X, Arg117His, 120del23, Phe508del, or a combination thereof, wherein X is any amino acid. In another particular embodiment, the CFTR is a Phe508del CFTR mutant. In another particular embodiment of the method, the method further comprises administering an additional therapeutic agent. In another particular embodiment of the method, the additional therapeutic agent comprises at least one of a small molecule drug, protein drug, nucleic acid drug, or combination thereof. In another particular embodiment of the method, the additional therapeutic agent is at least one of a CFTR potentiator, CFTR corrector, CFTR read-through agent, or a combination thereof. In another particular embodiment of the method, the additional therapeutic agent is a CFTR potentiator. In another particular embodiment of the method, the CFTR potentiator is ivacaftor.

In a particular embodiment of the method, the pharmaceutical formulation comprises, consists essentially of, or consists of a therapeutically effective amount of cysteine and proline as free amino acids and a therapeutically effective amount of at least one additional free amino acid consisting of glycine, tyrosine or lysine, and no other free amino acids.

Combinations of the recited amino acids include, for example: cysteine, proline, and glycine; cysteine, proline, and tyrosine; cysteine, proline, and lysine; cysteine, proline, glycine, and tyrosine; cysteine, proline, glycine, and lysine; cysteine, proline, tyrosine, and lysine; and cysteine, proline, glycine, tyrosine, and lysine.

In another particular embodiment of the method, the pharmaceutical formulation comprises a therapeutically effective amount of each of cysteine, proline, glycine, tyrosine and lysine, as free amino acids and no other free amino acids. In another particular embodiment of the method, the pharmaceutical formulation consists essentially of or consists of a therapeutically effective amount of each of cysteine, proline, glycine, tyrosine and lysine, as free amino acids.

In a further aspect, a method for increasing the number of cystic fibrosis transmembrane conductance regulator (CFTR) proteins present on the plasma membrane of at least one cell is presented, the method comprising: contacting the at least one cell with an effective amount of a pharmaceutical formulation described herein, wherein the contacting promotes at least one of folding of CFTR or transport of CFTR to the plasma membrane, thereby increasing the number of CFTR proteins present on the plasma membrane of the cell. In a particular embodiment of the method, the number of wild-type CFTR proteins on the plasma membrane increases. In another particular embodiment of the method, the number of mutant CFTR proteins on the plasma membrane increases. In another particular embodiment of the method, the number of CFTR proteins that are at least 90%, at least 95%, at least 98%, at least 99%, or at least 99.5% identical to the amino acid sequence of wild-type CFTR on the plasma membrane increases, wherein the wild-type CFTR comprises SEQ ID NO: 1. In another particular embodiment of the method, the one or more of the CFTR proteins comprise Gly542X, Gly551Asp, Arg553X, Arg117His, 120del23, Phe508del, or a combination thereof wherein X is any amino acid. In another particular embodiment of the method, the one or more of the CFTR proteins comprise the Phe508del mutation. In another particular embodiment of the method, the increasing the number of CFTR proteins present on the plasma membrane of the cell is detected by increased chloride ion export from the cell. In another particular embodiment of the method, the increasing the number of CFTR proteins present on the plasma membrane of the cell is associated with increased water export from the cell. In another particular embodiment of the method, the cell is an epithelial cell. In a more particular embodiment of the method, the epithelial cell is a lung epithelial cell. In a still more particular embodiment of the method, the lung epithelial cell is a bronchial epithelial cell. In another particular embodiment of the method, the bronchial epithelial cell is isolated from a subject afflicted with cystic fibrosis and results from in vitro assays performed on such cells provides guidance on what therapeutic agents and/or combinations thereof will confer therapeutic efficacy to the subject form whom the cells were isolated. In another particular embodiment of the method, the method further comprises administering an additional therapeutic agent. In another particular embodiment of the method, the additional therapeutic agent comprises at least one of a small molecule drug, protein drug, nucleic acid drug, or combination thereof. In another particular embodiment of the method, the additional therapeutic agent is at least one of a CFTR potentiator, CFTR corrector, CFTR read-through agent, or a combination thereof. In another particular embodiment of the method, the additional therapeutic agent is a CFTR potentiator. In another particular embodiment of the method, the CFTR potentiator is ivacaftor.

In a particular embodiment of the method, the pharmaceutical formulation comprises, consists essentially of, or consists of a therapeutically effective amount of cysteine and proline as free amino acids and a therapeutically effective amount of at least one additional free amino acid consisting of glycine, tyrosine or lysine, and no other free amino acids. Combinations of the recited amino acids include, for example: cysteine, proline, and glycine; cysteine, proline, and tyrosine; cysteine, proline, and lysine; cysteine, proline, glycine, and tyrosine; cysteine, proline, glycine, and lysine; cysteine, proline, tyrosine, and lysine; and cysteine, proline, glycine, tyrosine, and lysine.

In another particular embodiment of the method, the pharmaceutical formulation comprises a therapeutically effective amount of each of cysteine, proline, glycine, tyrosine and lysine, as free amino acids and no other free amino acids. In another particular embodiment of the method, the pharmaceutical formulation consists essentially of or consists of a therapeutically effective amount of each of cysteine, proline, glycine, tyrosine and lysine, as free amino acids.

In another particular embodiment, a kit is presented comprising: a pharmaceutical formulation comprising, consisting essentially of, or consisting of cysteine, proline, glycine, tyrosine and lysine, as free amino acids; and instructions for administering to a subject or contacting a biological sample with the composition.

In another aspect, the present disclosure provides compositions comprising, consisting essentially of, or consisting of a composition comprising, consisting essentially of, or consisting of cysteine, proline, glycine, tyrosine and lysine for use in treating cystic fibrosis. In a further aspect, the present invention provides use of the compositions of amino acids to treat cystic fibrosis in a subject in need thereof. In a further aspect, the present invention provides use of the compositions of amino acids in the preparation of a medicament for the treatment of cystic fibrosis in a subject in need thereof.

In one aspect, the present disclosure provides compositions comprising, consisting essentially of, or consisting of, cysteine, proline, glycine, tyrosine and lysine. In certain embodiments, the amino acids are L-amino acids. In certain embodiments, the composition further comprises water. In another aspect, the composition further comprises a pharmaceutically acceptable carrier, buffer, electrolyte, adjuvant, or excipient. In certain embodiments, the composition is sterile. In another aspect, the composition is formulated for administration by an enteral, pulmonary, inhalation, intranasal, or sublingual route.

In certain embodiments, the subject is suffering from cystic fibrosis in which wild-type CFTR is present. In one aspect, the subject has a mutation in the CFTR gene. In a further aspect, the subject is suffering from cystic fibrosis in which both wild-type and mutant CFTR are present. In yet another aspect, the subject is suffering from cystic fibrosis in which a CFTR protein that is at least 90%, at least 95%, at least 98%, at least 99%, or at least 99.5% identical to the amino acid sequence of wild-type CFTR as provided by SEQ ID NO: 1 is present. In still further aspects, the CFTR is a Gly542X, Gly551Asp, Arg553X, Arg117His, 120del23, or Phe508del CFTR mutant, wherein X is any amino acid. In certain embodiments, the CFTR is a Phe508del CFTR mutant.

Also provided herein are methods for increasing the number of cystic fibrosis transmembrane conductance regulator (CFTR) proteins present on the plasma membrane of a cell, the method comprising contacting the cell with an effective amount of a composition comprising, consisting essentially of, or consisting of cysteine, proline, glycine, tyrosine and lysine. In certain aspects, the effective amount increases the number of CFTR proteins present on the plasma membrane of the cell. In further aspects, the number of wild-type CFTR proteins on the plasma membrane increases. In still further aspects, the number of mutant CFTR proteins on the plasma membrane increases. In certain aspects, the number of CFTR proteins that are at least 90%, at least 95%, at least 98%, at least 99%, or at least 99.5% identical to the amino acid sequence of wild-type CFTR as provided by SEQ ID NO: 1 on the plasma membrane increases. In some embodiments, the one or more of the CFTR proteins are a Gly542X, Gly551Asp, Arg553X, Arg117His, 120del23, or Phe508del mutant, wherein X is any amino acid. In further embodiments, the one or more of the CFTR proteins are a Phe508del CFTR mutant. In certain embodiments, chloride ion export from the cell is increased. In further embodiments, water export from the cell is increased. In still further embodiments, the cell is an epithelial cell. In certain embodiments, the epithelial cell is a lung epithelial cell. In some embodiments, the lung epithelial cell is a bronchial epithelial cell. In further embodiments, the bronchial epithelial cell was obtained from a subject suffering from cystic fibrosis. The cells may be in vitro, in vivo, or ex vivo.

In certain aspects, the methods provided herein further comprise administering an additional therapeutic agent. In certain embodiments, the additional therapeutic agent is a small molecule drug, protein drug, or nucleic acid drug. In certain embodiments, the additional therapeutic agent is a small molecule drug. In further embodiments, the additional therapeutic agent is a CFTR potentiator, corrector, or read-through agent. In still further embodiments, the additional therapeutic agent is a CFTR potentiator. In some aspects, the CFTR potentiator is ivacaftor. In certain embodiments, the additional therapeutic agent is a CFTR corrector. In certain embodiments, the CFTR corrector is lumeaftor. The additional therapeutic agent may be included in any of the compositions described herein (e.g., the composition further comprises an additional therapeutic agent). The additional therapeutic agent may be administered concurrently with, prior to, or subsequently after, administration of any of the compositions described herein (e.g., combination therapy).

In a further aspect, the present disclosure provides a method for treating cystic fibrosis, the method comprising administering to a subject in need thereof a composition described herein, wherein the composition is formulated for administration by an enteral, pulmonary, inhalation, intranasal, or sublingual route. In certain embodiments, the composition is formulated for pulmonary administration to the subject. In certain embodiments, the composition is formulated for enteral administration to the subject. In certain embodiments, the composition is formulated for oral administration to the subject.

In a further aspect, the present disclosure provides a method for treating cystic fibrosis, the method comprising administering to a subject in need thereof a composition described herein. In certain embodiments, the subject is suffering from cystic fibrosis in which the subject has a mutation in the CFTR gene. In certain embodiments, the subject is suffering from cystic fibrosis in which the subject is heterozygous for both wild-type CFTR and mutant CFTR. In certain embodiments, the subject is suffering from cystic fibrosis in which the subject is heterozygous for a first mutant CFTR and a second mutant CFTR (e.g., wherein the mutations are different). In certain embodiments, the subject is suffering from cystic fibrosis in which the subject is homozygous for mutant CFTR (e.g., both alleles have the same mutation). In certain embodiments, the subject is suffering from cystic fibrosis in which the subject is homozygous for wild-type CFTR (e.g., both alleles are not mutated). In certain embodiments, the mutant CFTR is a Gly542X, Gly551Asp, Arg553X, Arg117His, 120del23, or Phe508del CFTR mutant, wherein X is any amino acid. In certain embodiments, the mutant CFTR is a Phe508del CFTR mutant. In certain embodiments, the CFTR protein present in the subject is least 90%, at least 95%, at least 98%, at least 99%, or at least 99.5% identical to the amino acid sequence of wild-type CFTR as provided by SEQ ID NO: 1. In certain embodiments, the CFTR protein present in the subject is least 90%, at least 95%, at least 98%, at least 99%, or at least 99.5% identical to the amino acid sequence of Phe508del CFTR as provided by SEQ ID NO: 2.

Information regarding diagnosis and treatments of various diseases, including cystic fibrosis and related pulmonary diseases, is found in Longo, D., et al. (eds.), *Harrison's Principles of Internal Medicine*, 18$^{th}$ Ed.; McGraw-Hill Professional, 2011. Information regarding various therapeutic agents and human diseases, including pulmonary disease, is found in Brunton, L., et al. (eds.) *Goodman and Gilman's The Pharmacological Basis of Therapeutics*, 12$^{th}$ Ed., McGraw Hill, 2010 and/or Katzung, B. (ed.) *Basic and Clinical Pharmacology*, McGraw-Hill/Appleton & Lange; 11$^{th}$ edition (July 2009). All patents, patent applications, books, articles, documents, databases, websites, publications, references, etc., mentioned herein are incorporated by reference in their entirety. In case of a conflict between the specification and any of the incorporated references, the specification (including any amendments thereof) shall control. Applicants reserve the right to amend the specification based, e.g., on any of the incorporated material and/or to correct obvious errors. None of the content of the incorporated material shall limit the invention. Standard art-accepted meanings of terms are used herein unless indicated otherwise. Standard abbreviations for various terms are used herein.

In certain aspects, the composition provided herein comprises, consists essentially of, or consists of one or more free amino acids selected from cysteine, proline, glycine, tyrosine and lysine, and no other free amino acids.

Also provided herein are uses of a composition to treat cystic fibrosis in a subject in need thereof, wherein the composition comprises cysteine, proline, glycine, tyrosine and lysine.

Also provided herein are kits comprising a composition comprising, consisting essentially of, or consisting of cysteine, proline, glycine, tyrosine and lysine; and instructions for administering to a subject or contacting a biological sample with the composition.

All combinations of separately described embodiments are envisaged.

The details of certain embodiments of the invention are set forth in the Detailed Description of Certain Embodiments, as described below. Other features, objects, and advantages of the invention will be apparent from the Definitions, Examples, Figures, and Claims.

Definitions

Descriptions and certain information relating to various terms used in the present disclosure are collected herein for convenience.

The term "agent" is used herein to refer to any substance, compound (e.g., molecule), supramolecular complex, material, or combination or mixture thereof. A compound may be any agent that can be represented by a chemical formula, chemical structure, or sequence. Example of agents, include, e.g., small molecules, polypeptides, nucleic acids (e.g., RNAi agents, antisense oligonucleotide, aptamers), lipids, polysaccharides, etc. In general, agents may be obtained using any suitable method known in the art. The ordinary skilled artisan will select an appropriate method based, e.g., on the nature of the agent. An agent may be at least partly purified. In some embodiments an agent may be provided as part of a composition, which may contain, e.g., a counterion, aqueous or non-aqueous diluent or carrier, buffer, preservative, or other ingredient, in addition to the agent, in various embodiments. In some embodiments an agent may be provided as a salt, ester, hydrate, or solvate. In some embodiments an agent is cell-permeable, e.g., within the range of typical agents that are taken up by cells and acts intracellularly, e.g., within mammalian cells, to produce a biological effect. Certain compounds may exist in particular geometric or stereoisomeric forms. Such compounds, including cis- and trans-isomers, E- and Z-isomers, R- and S-enantiomers, diastereomers, (D)-isomers, (L)-isomers, (−)- and (+)-isomers, racemic mixtures thereof, and other mixtures thereof are encompassed by this disclosure in various embodiments unless otherwise indicated. Certain compounds may exist in a variety or protonation states, may have a variety of configurations, may exist as solvates [e.g., with water (i.e. hydrates) or common solvents] and/or may have different crystalline forms (e.g., polymorphs) or different tautomeric forms. Embodiments exhibiting such alternative protonation states, configurations, solvates, and forms are encompassed by the present disclosure where applicable. The term "agent" may also encompass a "therapeutic agent". The term "compound" and "agent" may be used interchangeably.

An "effective amount" or "effective dose" of an agent (or composition containing such agent) refers to the amount sufficient to achieve a desired biological and/or pharmacological effect, e.g., when delivered to a cell or organism according to a selected administration form, route, and/or schedule. The phrases "effective amount" and "therapeutically effective amount" are used interchangeably. As will be appreciated by those of ordinary skill in this art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered to a subject in a single dose, or through use of multiple doses, in various embodiments. In certain embodiments, an effective amount is an amount that increases the trafficking of CFTR to the plasma membrane of a cell. In certain embodiments, an effective amount is an amount that increases the translocation of CFTR from the cytoplasm to the plasma membrane of a cell. In certain embodiments, an effective amount is an amount that increases the chloride ion export from a cell. In certain embodiments, an effective amount is an amount that increases water export from a cell. In certain embodiments, an effective amount is an amount that reduces the symptoms of and/or treats a lung disease. In certain embodiments, an effective amount is an amount that reduces the symptoms of and/or treats cystic fibrosis.

The term "consisting essentially of" as used herein, limits the scope of the ingredients and steps to the specified materials or steps and those that do not materially affect the basic and novel characteristic(s) of the present invention, e.g., compositions and use thereof for the treatment of cystic fibrosis and methods for treating cystic fibrosis. For instance, by using "consisting essentially of" the therapeutic composition does not contain any unspecified ingredients including, but not limited to, free amino acids, di-, oligo-, or polypeptides or proteins; and mono-, di-, oligo-, polysaccharides, and carbohydrates that have a direct beneficial or adverse therapeutic effect on treatment of cystic fibrosis. Also, by using the term "consisting essentially of" the composition may comprise substances that do not have therapeutic effects on the treatment of cystic fibrosis; such ingredients include carriers, excipients, adjuvants, flavoring agents, etc. that do not affect the health or function of the lung epithelium.

The description herein of any aspect or embodiment using terms such as "comprising", "having", "including", or "containing with reference to an element or elements is intended to provide support for a similar aspect or embodiment "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The term "gene" refers to a locus (e.g., region) of DNA that is comprised of nucleotides. Generally, a gene contains multiple regions, including one or more upstream or downstream regulatory sequences (e.g., enhancer/silencer, promoter, 5' non-coding sequences, 3' non-coding sequences) that is normally required to initiate transcription, an open reading frame comprising one or more exons and one or more introns. An "exon" is any part of a gene that will encode part of the final mature RNA, which will be translated into a protein sequence. An "intron" is any part of a gene that is removed by RNA splicing during maturation of the final mature RNA. A "cryptic exon" is an exon that can introduce a premature translation stop codon into mature RNA or result in atypical splicing patterns. The term "gene" may refer to a nucleic acid fragment that expresses a protein, including regulatory sequences preceding (5' non-coding sequences) and following (3' non-coding sequences) the coding sequence. "Native gene" refers to a gene as found in nature with its own regulatory sequences. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes.

The term "gene product" (also referred to herein as "gene expression product" or "expression product") encompasses products resulting from expression of a gene, such as RNA transcribed from a gene and polypeptides arising from translation of such RNA. It will be appreciated that certain gene products may undergo processing or modification, e.g., in a cell. For example, RNA transcripts may be spliced, polyadenylated, etc., prior to mRNA translation, and/or polypeptides may undergo co-translational or post-translational processing such as removal of secretion signal sequences, removal of organelle targeting sequences, or modifications such as phosphorylation, fatty acylation, etc. The term "gene product" encompasses such processed or modified forms. Genomic, mRNA, polypeptide sequences from a variety of species, including human, are known in the art and are available in publicly accessible databases such as those available at the National Center for Biotechnology Information (www.ncbi.nih.gov) or Universal Protein Resource (www.uniprot.org). Databases include, e.g., GenBank, RefSeq, Gene, UniProtKB/SwissProt, UniProtKB/Trembl, and the like. In general, sequences, e.g., mRNA and polypeptide sequences, in the NCBI Reference Sequence database may be used as gene product sequences for a gene of interest. It will be appreciated that multiple alleles of a gene may exist among individuals of the same species. For example, differences in one or more nucleotides (e.g., up to about 1%, 2%, 3-5% of the nucleotides) of the nucleic acids encoding a particular protein may exist among individuals of a given species. Due to the degeneracy of the genetic code, such variations often do not alter the encoded amino acid sequence, although DNA polymorphisms that lead to changes in the sequence of the encoded proteins can exist. Examples of polymorphic variants can be found in, e.g., the Single Nucleotide Polymorphism Database (dbSNP), available at the NCBI website at www.ncbi.nlm.nih.gov/projects/SNP/ [Sherry, S. T., et al. (2001) dbSNP: The NCBI database of genetic variation. *Nucl Acids Res,* 29: 308-311; Kitts, A. and Sherry, S. (2009) The single nucleotide polymorphism database (dbSNP) of nucleotide sequence variation. In: *The NCBI Handbook* (Internet); McEntyre, J., Ostell, J., editors. Bethesda (Md.): National Center for Biotechnology Information (US); 2002 (www.ncbi.nlm.nih.gov/bookshelf/br.fcgi?book=handbook&part=ch5)]. Multiple isoforms of certain proteins may exist, e.g., as a result of alternative RNA splicing or editing. In general, where aspects of this disclosure pertain to a gene or gene product, embodiments pertaining to allelic variants or isoforms are encompassed, if applicable, unless indicated otherwise. Certain embodiments may be directed to particular sequence(s), e.g., particular allele(s) or isoform(s).

The term "amino acid" encompasses all known amino acids comprising an amine (—NH2) functional group, a carboxyl (—COOH) functional group, and a side chain ("R") group specific to each amino acid. "Amino acids" encompasses the 21 amino acids encoded by the human genome (i.e., proteinogenic amino acids), amino acids encoded or produced by bacteria or single-celled organisms, and naturally derived amino acids. For the purposes of this disclosure, the conjugate acid form of amino acids with basic side chains (arginine, lysine, and histidine) or the conjugate base form of amino acids with acidic side chains (aspartic acid and glutamic acid) are essentially the same, unless otherwise noted. "Amino acids" also encompass derivatives thereof that retain substantially the same, or better, activity in terms of enhancing the effect of a composition of the present invention (e.g., increasing the number of CFTR proteins in the plasma membrane, increasing chloride ion export from a cell, treating cystic fibrosis). The derivatives may be, for example, enantiomers, and include both the D- and L-forms of the amino acids. The derivatives may be derivatives of "natural" or "non-natural" amino acids (e.g., R-amino acids, homo-amino acids, proline derivatives, pyruvic acid derivatives, 3-substituted alanine derivatives, glycine derivatives, ring-substituted tyrosine derivatives, ring-substituted phenylalanine derivatives, linear core amino acids, and N-methyl amino acids), for example, selenocysteine, pyrrolysine, iodotyrosine, norleucine, or norvaline. Other amino acid derivatives include, but are not limited to, those that are synthesized by, for example, acylation, methylation, glycosylation, and/or halogenation of the amino acid. These include, for example, P-methyl amino acids, C-methylamino acids, and N-methyl amino acids. The amino acids described herein may be present as free amino acids. The term "free amino acid" refers to an amino acid that is not part of a peptide or polypeptide (e.g., is not connected to another amino acid through a peptide bond). A free amino acid is free in solution, but may be associated with a salt or other component in solution.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. In some embodiments, a protein comprises a homodimer or a heterodimer. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain (e.g., the gRNA binding domain of Cas9 that directs the binding of the protein to a target site) and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA. In some embodiments, a protein comprises a ligand binding domain. In some embodiments, a protein comprises an active site (e.g., site of biological or enzymatic activity). In some embodiments, a protein comprises an allosteric site (e.g., site of a protein that can bind to a ligand that can be remote from an active site). Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* [4$^{th}$ ed., Cold Spring Harbor Laboratory Press, Cold Spring Harbor, N.Y. (2012)], the entire contents of which are incorporated herein by reference.

"Identity" or "percent identity" is a measure of the extent to which the sequence of two or more nucleic acids or polypeptides is the same. The percent identity between a sequence of interest A and a second sequence B may be computed by aligning the sequences, allowing the introduction of gaps to maximize identity, determining the number of residues (nucleotides or amino acids) that are opposite an identical residue, dividing by the minimum of TGA and TGB (here TGA and TGB are the sum of the number of residues and internal gap positions in sequences A and B in the alignment), and multiplying by 100. When computing the number of identical residues needed to achieve a particular percent identity, fractions are to be rounded to the nearest whole number. Sequences can be aligned with the use of a variety of computer programs known in the art. For example, computer programs such as BLAST2, BLASTN, BLASTP, Gapped BLAST, etc., may be used to generate alignments and/or to obtain a percent identity. The algorithm of Karlin and Altschul (Karlin and Altschul, *Proc Natl Acad Sci USA*, 87: 22264-2268, 1990) modified as in Karlin and Altschul, *Proc Natl Acad Sci USA*, 90: 5873-5877, 1993 is incorporated into the NBLAST and XBLAST programs of Altschul et al. [Altschul, et al. (1990) *J Mol Biol,* 215: 403-410]. In some embodiments, to obtain gapped alignments for comparison purposes, Gapped BLAST is utilized as described in Altschul et al. [Altschul, et al. (1997) *Nucleic Acids Res,* 25: 3389-3402]. When utilizing BLAST and Gapped BLAST programs, the default parameters of the respective programs may be used. See the Web site having URL www.ncbi.nlm.nih.gov and/or McGinnis, S. and Madden, T L, W20-W25 Nucleic Acids Research, 2004, Vol. 32, Web server issue. Other suitable programs include CLUSTALW [Thompson, J. D., Higgins, D. G., and Gibson, T. J. (1994) *Nuc Acid Res,* 22: 4673-4680], CLUSTAL Omega [Sievers, F., Wilm, A., Dineen, D., et al. (2011) Fast, scalable generation of high-quality protein multiple sequence alignments using Clustal Omega. *Mol Sys Biol,* 7: doi:10.1038/msb.2011.75], and GAP (GCG Version 9.1; which implements the Needleman & Wunsch, 1970 algorithm [Needleman, S. B. and Wunsch, C. D. (1970) *J Mol Biol,* 48: 443-453]). Percent identity may be evaluated over a window of evaluation. In some embodiments a window of evaluation may have a length of at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more, e.g., 100%, of the length of the shortest of the sequences being compared. In some embodiments a window of evaluation is at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments no more than 20%, 10%, 5%, or 1% of positions in either sequence or in both sequences over a window of evaluation are occupied by a gap. In some embodiments no more than 20%, 10%, 5%, or 1% of positions in either sequence or in both sequences are occupied by a gap.

A "variant" of a particular polypeptide or polynucleotide has one or more additions, substitutions, and/or deletions with respect to the polypeptide or polynucleotide, which may be referred to as the "original polypeptide" or "original polynucleotide," respectively. An addition may be an insertion or may be at either terminus. A variant may be shorter or longer than the original polypeptide or polynucleotide. The term "variant" encompasses "fragments". A "fragment" is a continuous portion of a polypeptide or polynucleotide that is shorter than the original polypeptide. In some embodiments a variant comprises or consists of a fragment. In some embodiments a fragment or variant is at least 20%, 30%, 40%, 50%, 60%, 70%, 80%, 90%, 95%, 96%, 97%, 98%, 99%, or more as long as the original polypeptide or polynucleotide. A fragment may be an N-terminal, C-terminal, or internal fragment. In some embodiments a variant polypeptide comprises or consists of at least one domain of an original polypeptide. In some embodiments a variant polypeptide or polynucleotide comprises or consists of a polypeptide or polynucleotide that is at least 70%, 80%, 90%, 95%, 96%, 97%, 98%, 99%, or more identical in sequence to the original polypeptide or polynucleotide. In some embodiments a variant polypeptide or polynucleotide comprises or consists of a polypeptide or polynucleotide that is over at least 50%, 60%, 70%, 80%, 90%, 95%, 96%, 97%, 98%, 99%, or 100% of the original polypeptide or polynucleotide. In some embodiments the sequence of a variant polypeptide comprises or consists of a sequence that has N amino acid differences with respect to an original sequence, wherein N is any integer up to 1%, 2%, 5%, or 10% of the number of amino acids in the original polypeptide, where an "amino acid difference" refers to a substitution, insertion, or deletion of an amino acid. In some embodiments a substitution is a conservative substitution. Conservative substitutions may be made, e.g., on the basis of similarity in side chain size, polarity, charge, solubility, hydrophobicity, hydrophilicity and/or the amphipathic nature of the residues involved. In some embodiments, conservative substitutions may be made according to Table A, wherein amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

TABLE A

| Aliphatic | Non-polar | G A P |
|---|---|---|
|  |  | I L V |
|  | Polar (uncharged) | C S T M |
|  |  | N Q |
|  | Polar (charged) | D E |
|  |  | K R |
| Aromatic |  | H F Y W |

In some embodiments, proline (P), cysteine (C), or both are each considered to be in an individual group. Within a particular group, certain substitutions may be of particular interest in certain embodiments, e.g., replacements of leucine by isoleucine (or vice versa), serine by threonine (or vice versa), or alanine by glycine (or vice versa).

In some embodiments a variant is a biologically active variant, i.e., the variant at least in part retains at least one activity of the original polypeptide or polynucleotide. In some embodiments a variant at least in part retains more than one or substantially all known biologically significant activities of the original polypeptide or polynucleotide. An activity may be, e.g., a catalytic activity, binding activity, ability to perform or participate in a biological structure or process, etc. In some embodiments an activity of a variant may be at least 10%, 20%, 30%, 40%, 50%, 60%, 70%, 80%, 90%, 95%, or more, of the activity of the original polypeptide or polynucleotide, up to approximately 100%, approximately 125%, or approximately 150% of the activity of the original polypeptide or polynucleotide, in various embodiments. In some embodiments a variant, e.g., a biologically active variant, comprises or consists of a polypeptide at least 95%, 96%, 97%, 98%, 99%, 99.5% or 100% identical to an original polypeptide or over at least 70%, 75%, 80%, 85%, 90%, 95%, 96%, 97%, 98%, or 99% or 100% of the original polypeptide. In some embodiments an alteration, e.g., a substitution or deletion, e.g., in a functional variant, does not alter or delete an amino acid or nucleotide that is known or predicted to be important for an activity, e.g., a known or predicted catalytic residue or residue involved in binding a substrate or cofactor. Variants may be tested in one or more suitable assays to assess activity.

The term "small molecule" as used herein, is an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference. All listed drugs are considered acceptable for use in accordance with the present invention.

The terms "composition" and "formulation" are used interchangeably.

The term "administer," "administering," or "administration" refers to implanting, absorbing, ingesting, injecting, inhaling, or otherwise introducing a compound described herein, or a composition thereof, in or on a subject.

A "subject" may be any vertebrate organism in various embodiments. A subject may be individual to whom an agent is administered, e.g., for experimental, diagnostic, and/or therapeutic purposes or from whom a sample is obtained or on whom a procedure is performed. In some embodiments a subject is a mammal, e.g., a human, non-human primate, or rodent (e.g., mouse, rat, rabbit). Mammalian species that can benefit from the disclosed methods of treatment include, but are not limited to, apes, chimpanzees, orangutans, humans, monkeys; domesticated animals such as dogs, cats; livestock such as horses, cattle, pigs, sheep, goats, chickens; and animals such as mice, rats, guinea pigs, and hamsters. In certain embodiments, the subject is a human. The human may be of either sex and may be at any stage of development. In certain embodiments, a subject has been diagnosed with cystic fibrosis. In certain embodiments, a subject has been diagnosed with cystic fibrosis caused by a CFTR mutation. In certain embodiments, a subject has been diagnosed with cystic fibrosis caused by a Phe508del CFTR mutation.

Animal models of human CF are known in the art and are described herein. See, for example, Example 4. See also, Grubb et al. (Am J Physiol Lung Cell Mol Physiol 290: L270-L277, 2006); McCarron et al. (Respiratory Research 19:54, 2018); and Lavelle et al. (BioMed Research International Volume 2016, Article ID 5258727, 14 pages), the entire content of each of which is incorporated herein by reference. Lavelle et al., for example, describes mouse and pig models of CF.

"Treat," "treatment", "treating" and similar terms as used herein in the context of treating a subject refer to providing medical and/or surgical management of a subject. Treatment may include, but is not limited to, administering an agent or composition (e.g., a pharmaceutical composition) to a subject. The term "treatment" or any grammatical variation thereof (e.g., treat, treating, and treatment etc.), as used herein, includes but is not limited to, alleviating a symptom of a disease or condition; and/or reducing, suppressing, inhibiting, lessening, or affecting the progression, severity, and/or scope of a disease or condition. The effect of treatment may also include reducing the likelihood of occurrence or recurrence of the disease or one or more symptoms or manifestations of the disease. A therapeutic agent may be administered to a subject who has a disease or is at increased risk of developing a disease relative to a member of the general population. In some embodiments, a therapeutic agent may be administered to a subject who has had a disease but no longer shows evidence of the disease. The agent may be administered, e.g., to reduce the likelihood of recurrence of the disease. A therapeutic agent may be administered prophylactically, i.e., before development of any symptom or manifestation of a disease.

"Prophylactic treatment" refers to providing medical and/or surgical management to a subject who has not developed a disease or does not show evidence of a disease in order, e.g., to reduce the likelihood that the disease will occur or to reduce the severity of the disease should it occur. The subject may have been identified as being at risk of developing the disease (e.g., at increased risk relative to the general population or as having a risk factor that increases the likelihood of developing the disease).

The term "amelioration" or any grammatical variation thereof (e.g., ameliorate, ameliorating, and amelioration, etc.), as used herein, includes, but is not limited to, delaying the onset, or reducing the severity of a disease or condition (e.g., cystic fibrosis or a complication thereof). Amelioration, as used herein, does not require the complete absence of symptoms.

The terms "condition," "disease," and "disorder" are used interchangeably.

An "effective amount" of a compound described herein refers to an amount sufficient to elicit the desired biological response. In certain embodiments, an effective amount is an amount sufficient to increase chloride ion transport. In certain embodiments, an effective amount is an amount sufficient to modulate (e.g., increase) the function of the cystic fibrosis transmembrane conductance regulator (CFTR) protein (e.g., wild-type CFTR or mutant CFTR). In certain embodiments, an effective amount is an amount sufficient to modulate (e.g., increase) the function of Phe508del CFTR. In certain embodiments, an effective amount is an amount sufficient to increase the translocation of CFTR from the cytoplasm to the plasma membrane. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for increasing chloride ion transport (e.g., increasing chloride export from an epithelial cell). In certain embodiments, a therapeutically effective amount is an amount sufficient for increasing water transport (e.g., increasing water export from an epithelial cell). In certain embodiments, a therapeutically effective amount is an amount sufficient for modulating (e.g., increasing) the function of the cystic fibrosis transmembrane conductance regulator (CFTR) protein (e.g., wild-type CFTR or mutant CFTR). In certain embodiments, a therapeutically effective amount is an amount sufficient to modulate (e.g., increase) the function of Phe508del CFTR. In certain embodiments, a therapeutically effective amount is an amount sufficient to increase the translocation of CFTR from the cytoplasm to the plasma membrane. In certain embodiments, a therapeutically effective amount is an amount sufficient for treating a lung disease. In certain embodiments, a therapeutically effective amount is an amount sufficient for treating cystic fibrosis.

As used herein, the term "salt" refers to any and all salts, and encompasses pharmaceutically acceptable salts.

The term "carrier" may refer to any diluent, adjuvant, excipient, or vehicle with which a composition of the present disclosure is administered. Examples of suitable pharmaceutical carriers are described in *Remington's Essentials of Pharmaceuticals*, 21$^{st}$ ed., Ed. Felton, 2012, which is herein incorporated by reference.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition. The exact amount of a composition comprising amino acids required to achieve an effective amount will vary from subject to subject, depending, for example, on species, age, and general condition of a subject, severity of the side effects or disorder, identity of the particular compound, mode of administration, and the like.

An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a composition comprising amino acids described herein. In certain embodiments, a dose described herein includes independently between 1 mg and 3 mg, inclusive, of a composition comprising amino acids described herein. In certain embodiments, a dose described herein includes independently between 3 mg and 10 mg, inclusive, of a composition comprising amino acids described herein. In certain embodiments, a dose described herein includes independently between 10 mg and 30 mg, inclusive, of a composition comprising amino acids described herein. In certain embodiments, a dose described herein includes independently between 30 mg and 100 mg, inclusive, of a composition comprising amino acids described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The composition can be administered concurrently with, prior to, or subsequent to one or more additional pharmaceutical agents or therapeutic agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, lung disease, gastrointestinal disease, hematological disease, neurological disease, painful condition, psychiatric disorder, or metabolic disorder). In certain embodiments, the additional therapeutic agent is an agent useful for treating a lung disease.

In certain embodiments, the additional therapeutic agent is an agent useful for treating cystic fibrosis. In certain embodiments, an agent useful for treating cystic fibrosis may be ivacaftor (KALYDECO®), lumacaftor (ORKAMBI®), ataluren, or tezacaftor. In certain embodiments, the additional therapeutic agent is ivacaftor. In certain embodiments, the additional therapeutic agent is lumacaftor. In certain embodiments, the additional therapeutic agent is an agent useful for treating cystic fibrosis, managing the symptoms associated with cystic fibrosis, or for treating diseases or infections which occur concurrently with cystic fibrosis (e.g., bacterial infection, viral infection, bronchiolitis, asthma, etc.). Additional therapeutics useful for the purposes of this disclose include, but are not limited to, dornase alfa systemic (Pulmozyme), azithromycin (e.g., Zithromax, Zmax), aztreonam (Cayston, Azactam), tobramycin (e.g., TOBI®, Nebcin, Bethkis, Kitabis Pak, TOBI Podhaler), Amikin, pancrelipase (Creon, Zenpep, Pancreaze, Viokase, Pertzye, Ultresa, Pangestyme EC, Panocaps), gentamicin (Garamycin), and pancreatin. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

The term "lung disease" or "pulmonary disease" refers to a disease of the lung. Examples of lung diseases include, but are not limited to, cystic fibrosis and conditions associated therewith, including: bronchiectasis, bronchitis, asthma (e.g., intermittent asthma, mild persistent asthma, moderate persistent asthma, severe persistent asthma), chronic bronchitis, and pulmonary fibrosis.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form. In certain embodiments, a kit described herein further includes instructions for using the kit.

DETAILED DESCRIPTION OF CERTAIN EMBODIMENTS

CF is the most common lethal recessive genetic disorder among individuals of European decent, affecting between 1 in 2,500 to 1 in 3,500 newborns each year. CF is caused by mutations in the cystic fibrosis transmembrane conductance regulator (CFTR) gene that result in reduction or lack of CFTR synthesis, protein misfolding and/or channel dysfunction, which lead to decreased chloride secretion, increased sodium absorption (ENaC), and impaired fluid homeostasis in airway, intestinal, and pancreas epithelial cells. The CFTR gene is expressed in multiple tissues. CF is characterized by multi-system pathology that includes the respiratory, gastrointestinal, pancreatic, and hepatobiliary systems. Primary morbidity and mortality are related to chronic pulmonary infection and inflammation.

CF mutations are classified as: Class I (22%)=no CFTR expression; Class II (88%)=misfolded CFTR protein; Class III (6%)=CFTR channel does not open; Class IV (6%) =faulty CFTR channel; Class V (5%)=too little CFTR. Mutations may also span more than one category. Drugs such as lumacaftor are used to address Class II mutations (folding); drugs such as tezacaftor or ivacaftor are 'potentiators' which are used to address Class III-V mutations.

Recent advances in CF therapy using small molecules that selectively activate CFTR activity or correct protein misfolding have shown limited success with respect to treating subjects having the CFTRΔF508 mutation. The present inventors have identified select amino acid (AA) combinations that can stimulate chloride secretion and reduce ENaC activity, thereby increasing apical chloride channel activity and decreasing sodium absorption on the apical membrane. Accordingly, the select AA combinations and compositions thereof are presented as therapeutic agents for the treatment of subjects afflicted with CF alone and in combination with other CF therapeutic agents such as, for example, lumacaftor, tezacaftor, and/or ivacaftor. Also encompassed herein is the use of the select AA combinations for the treatment CF or in the preparation of medicaments for treating CF, wherein the use is alone and/or in combination with other CF therapeutic agents such as, for example, lumacaftor, tezacaftor, and/or ivacaftor.

Figure 7A:
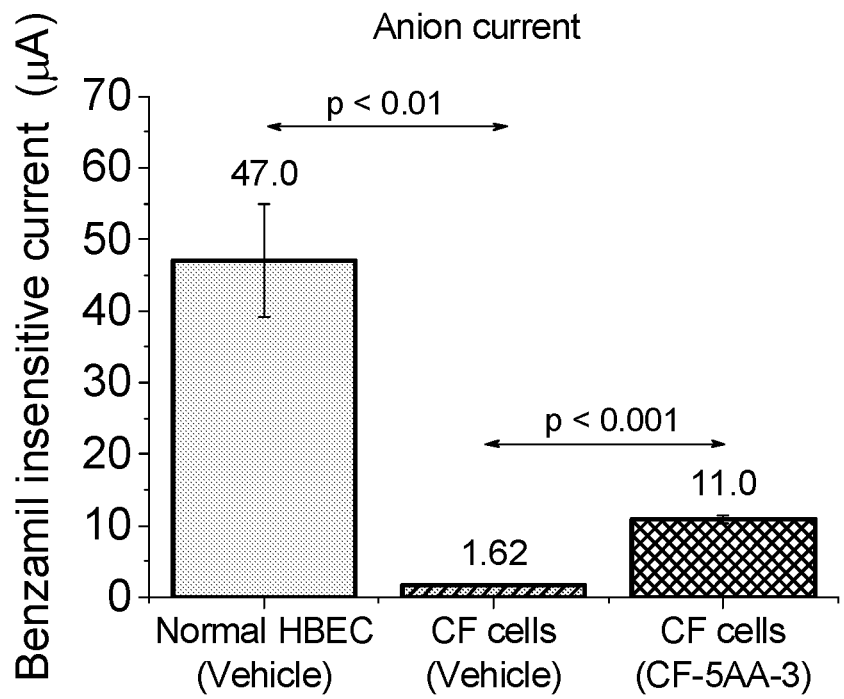
FIG. 7A-7F shows graphs depicting anion currents and stimulated chloride flux.
Figure 7B:
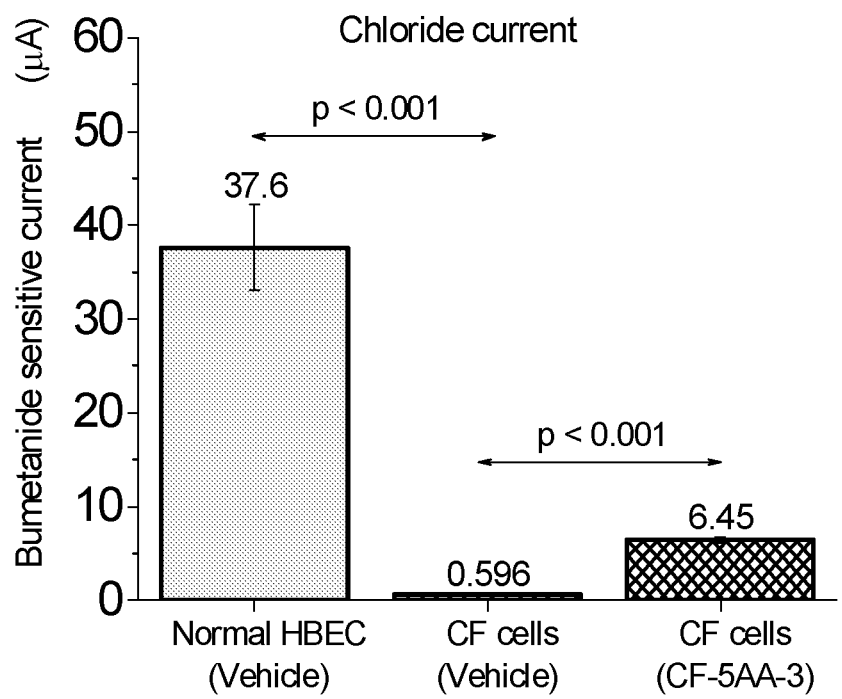
Figure 7C:
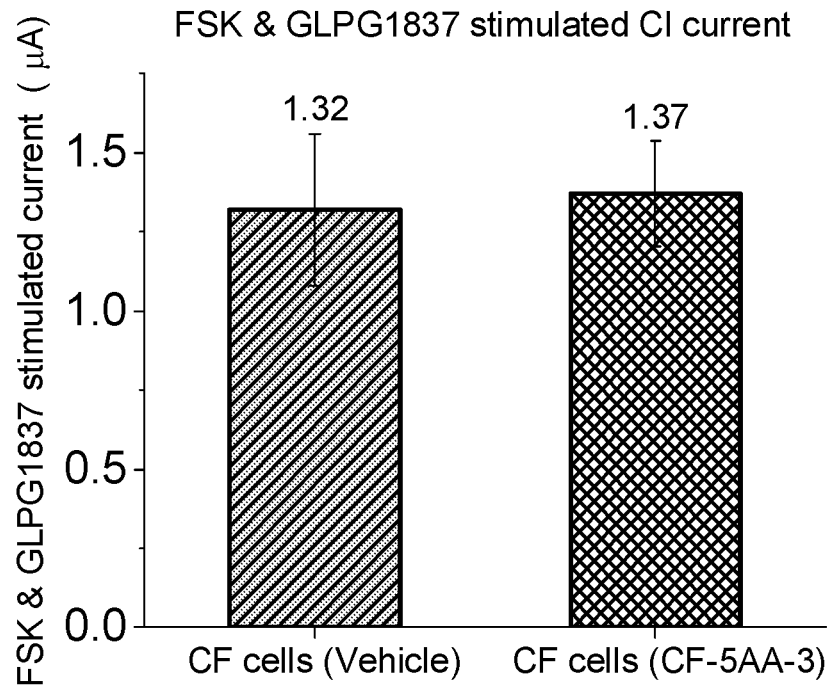
Figure 7D:
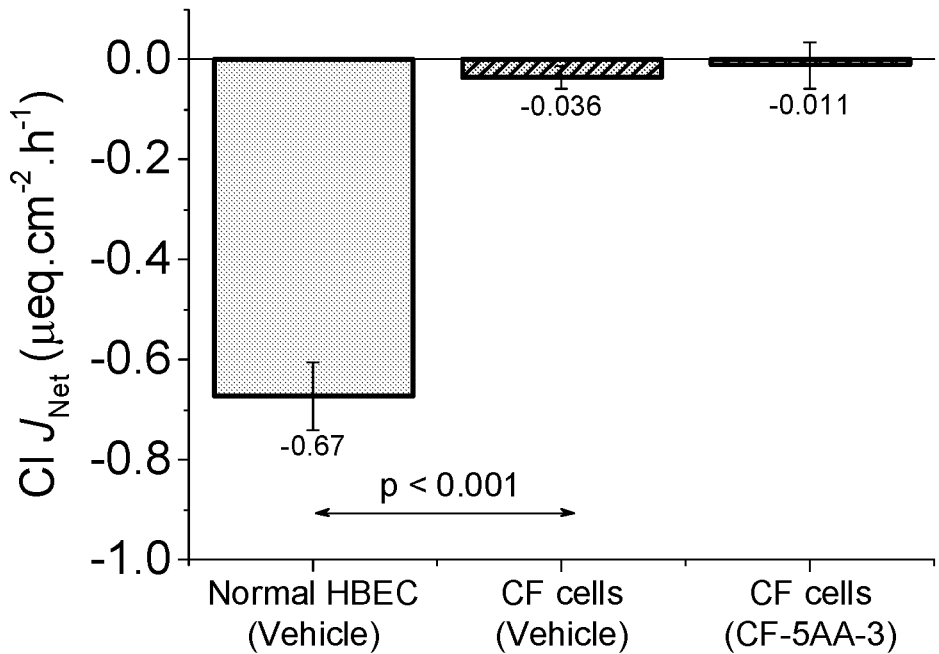
Figure 7E:
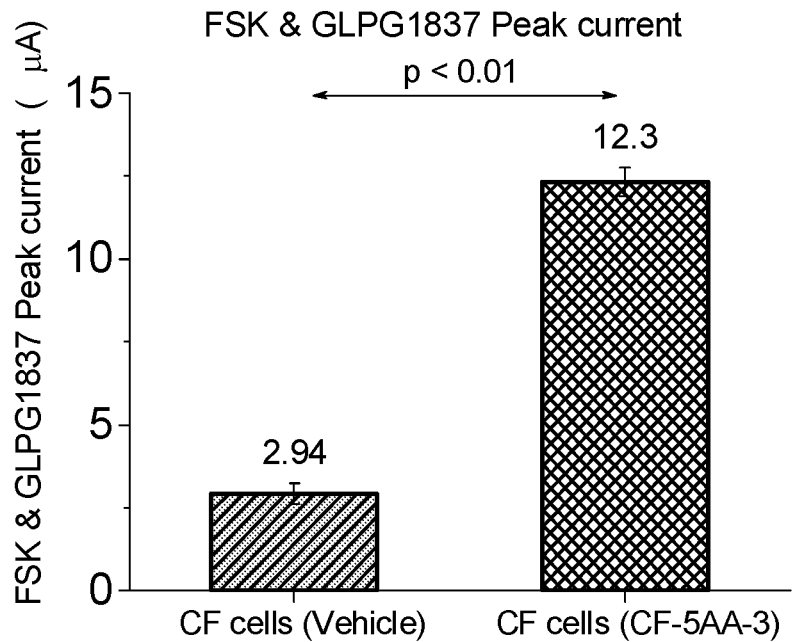
Figure 7F:
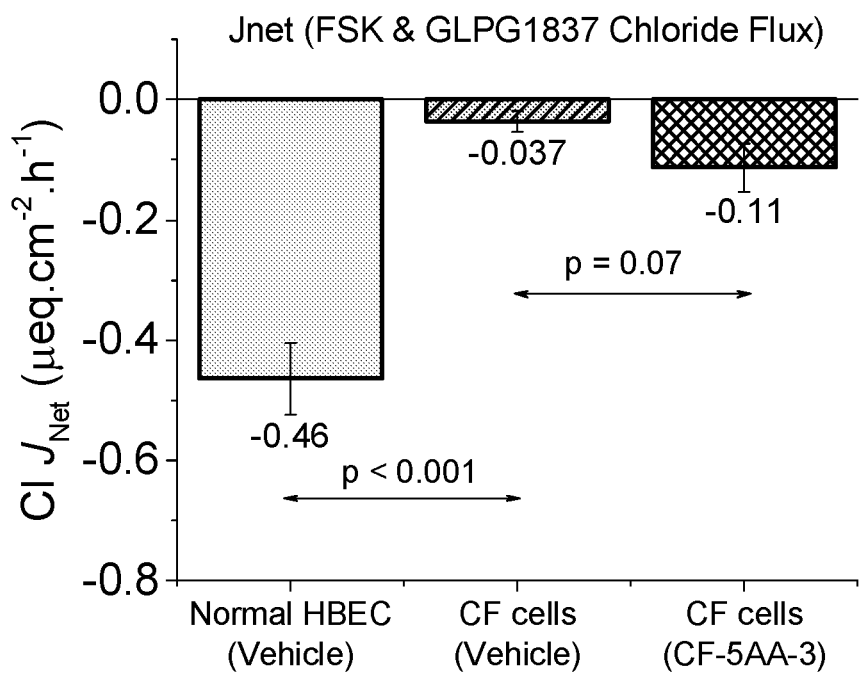
Figure 8A:
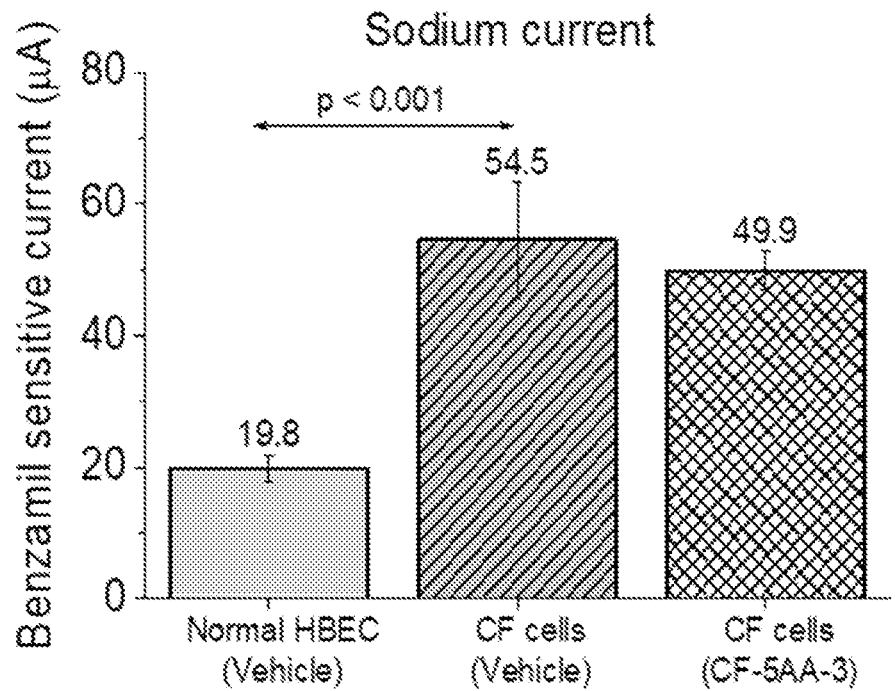
FIG. 8A and FIG. 8B show graphs depicting ENaC activity and blocked sodium flux.
Figure 8B:
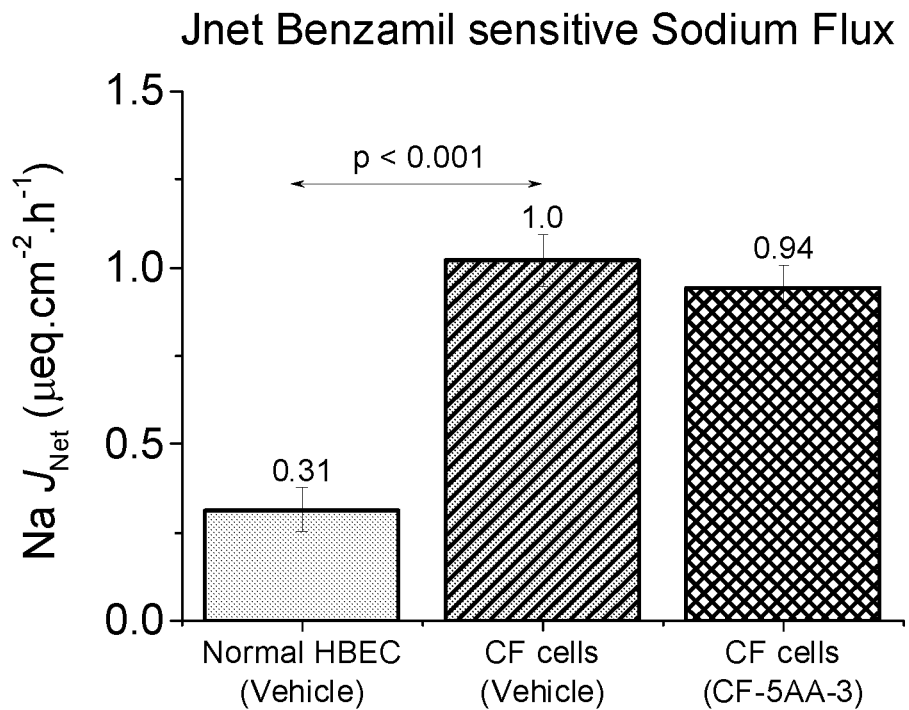
Figure 9:
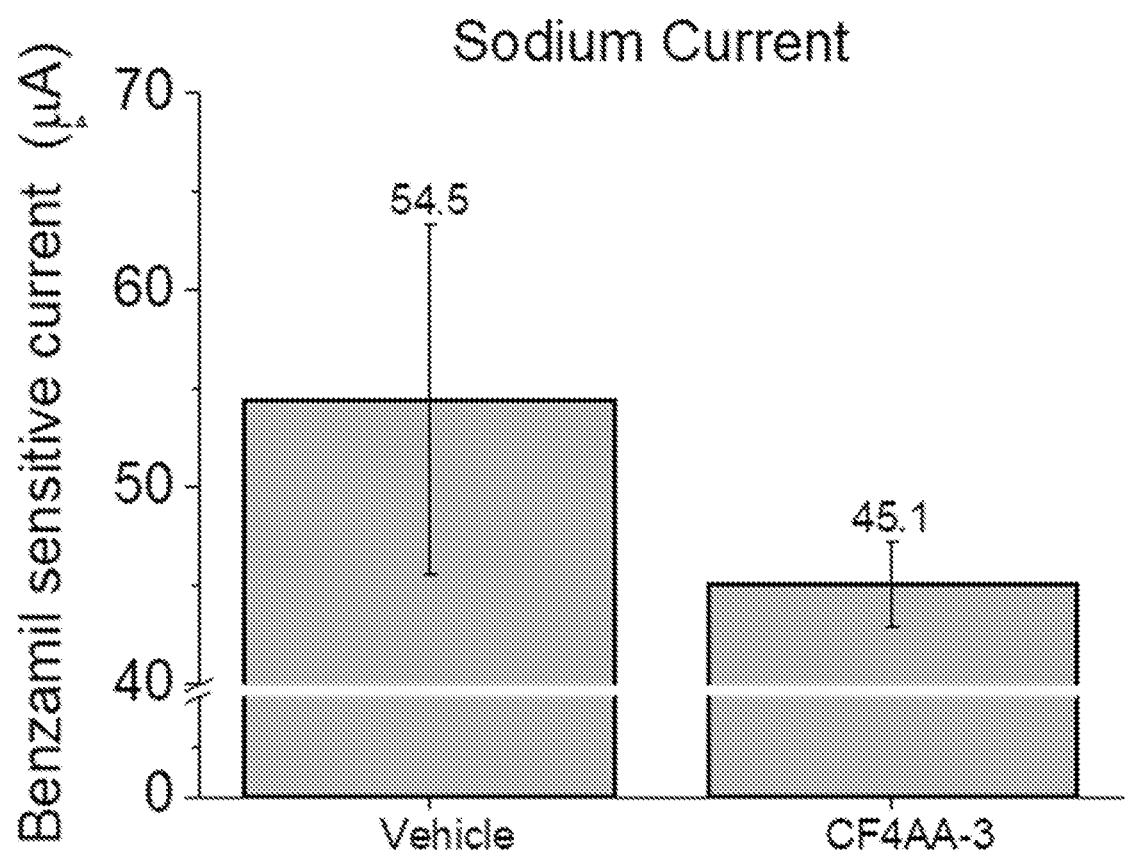
FIG. 9 shows a graph depicting an effect of the indicated AA formulation on ENaC activity in CF cells. CF cells bathed in CF-4AA-3 could further decrease the ENaC activity compared to vehicle and CF-5AA-3 (n=4).

As described herein, the present inventors have experimentally compared fully differentiated primary normal human bronchial epithelial cells to homozygous CFTRΔF508 (Class II mutation) human bronchial epithelial cells. Briefly, transepithelial short-circuit current ($I_{sc}$), resistance (R), and unidirectional ($J_{ms}$ & $J_{sm}$) and net fluxes ($J_{net}$) of $^{22}$Na and $^{36}$Cl have been measured in Ussing chambers. When CF cells were stimulated with forskolin and GLPG1837 (potentiator alternative to ivacaftor) in the absence (control) or presence of CF-5AA-3 (amino acid formulation for treating CF), peak current (FIG. 7E) and chloride secretion (FIG. 7F) were significantly improved in the presence of CF-5AA-3 (also referred to herein as CF5AA-3). For additional study details, see Example 2 below.

Results presented in, for example, FIGS. 5-9 demonstrate that select amino acid combinations (e.g., CF-5AA-3) improve dysfunctional chloride and sodium channel activity in CFTRΔF508 fully differentiated primary normal human bronchial epithelial cells (HBEC), which are homozygous for CFTRΔF508, by correcting and/or modifying plasma membrane channel function. Accordingly, select amino acid formulations (e.g., CF-5AA-3) are proposed to complement existing standard of care in patients with the CFTRΔF508 mutation.

Figure 10A:
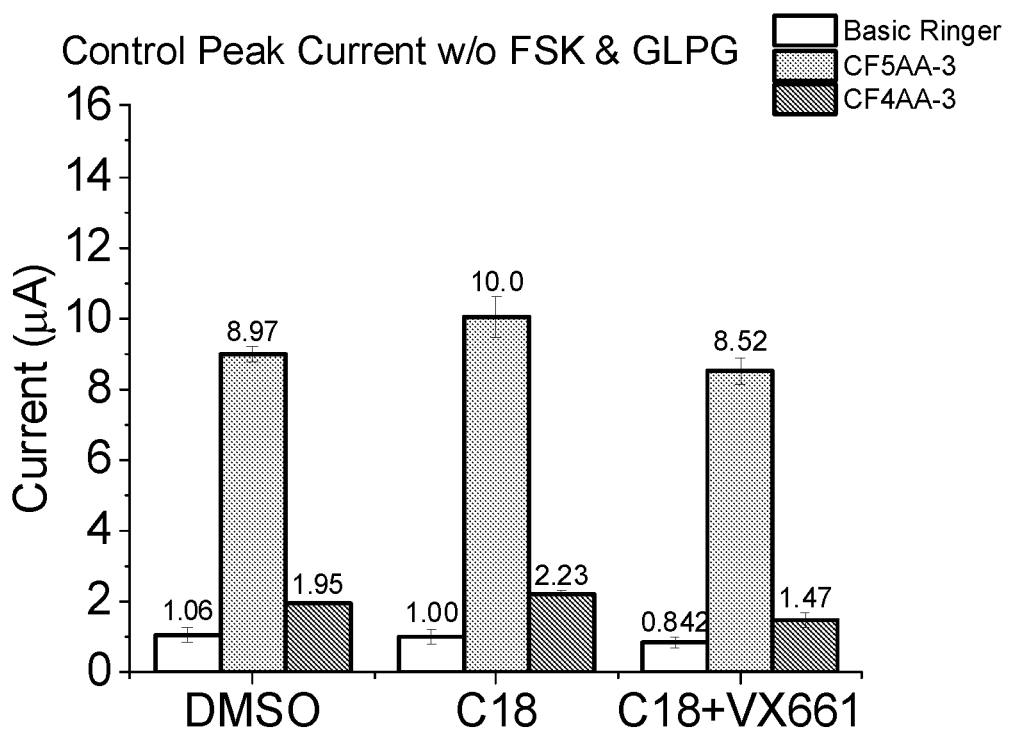
FIG. 10A and FIG. 10B present graphs depicting an effect of C18 (corrector; similar to Lumacaftor) and/or VX661 (corrector; tezacaftor) in the presence of forskolin and potentiator on CFTRΔF508 cells. Ivacaftor: GLPG1837 (reversible potentiator); Symdeko: VX661(tezacaftor)/C18. CF5AA-3 increased current to a greater extent than C18 or Symdeko.
Figure 10B:
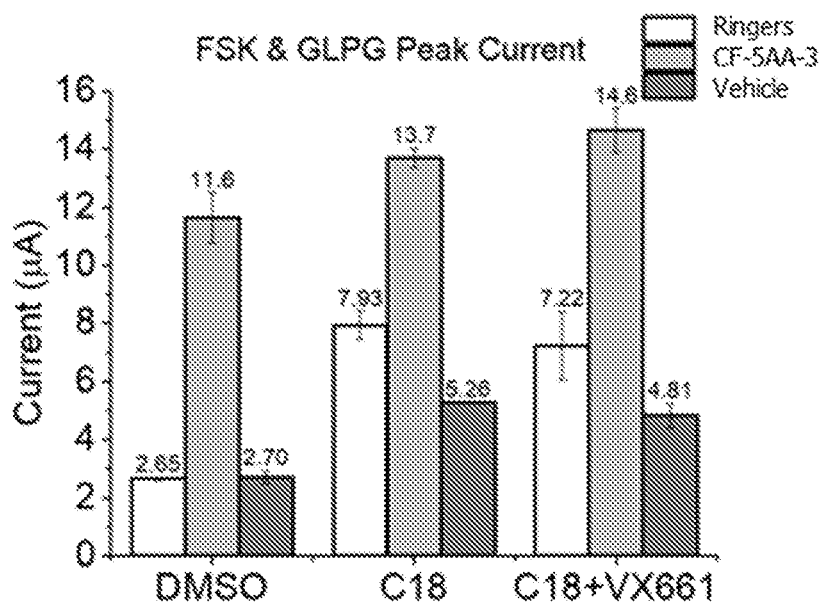

In the presence of correctors (C18; VX661, tezacaftor) and potentiator (GLPG1837, alternative to ivacaftor), peak currents more than doubled from baseline, but remained below CF-5AA-3 basal peak current when used alone. The addition of the same triple cocktail to CF-5AA-3 increased current another 26% relative to that of CF-5AA-3 alone (FIG. 10A and FIG. 10B).

In addition, it was further demonstrated that chloride flux was dramatically increased by CF-5AA-3 compared to triple cocktail (FIG. 11) due to direct effects on both CFTR and ANO1 channels. CF-5AA-3 exhibited only a minor effect on ENaC. For additional study details, see Example 2 below.

In summary, the in vitro electrophysiological research using primary human bronchial epithelial cells with the CFTRΔF508 mutation (Class II) show that CF-5AA-3 alone quantitatively increases chloride secretion (negative flux) in F508del human bronchial cells similarly to common correctors and potentiators [column AA DMSO BASAL vs. column C18+GLPG] and CF-5AA-3 in combination with a commonly used corrector (C18) and potentiator (GLPG) doubles chloride secretion (negative flux) when compared to corrector and potentiator alone.

Results presented herein indicate that additional chloride channels may also be active (e.g., SLC26A9) in HBEC. Activation of chloride channels other than CFTR suggests that CF-5AA-3 may provide relief to all 5 classes of CF mutations by inducing chloride secretion via CFTR independent means. This is particularly noteworthy with respect to subjects having CFTR Class I mutations for which there are currently no drugs.

Compositions Comprising Amino Acids that Increase Translocation of CFTR to the Plasma Membrane The compositions provided herein increase the translocation of both wild-type and mutant CFTR proteins from the cytoplasm to the plasma membrane. In particular, the compositions described herein are particularly effective at increasing the number of Phe508del CFTR proteins on the plasma membrane, leading to more chloride ion and water secretion from epithelial cells to combat the formation of thick mucus, a hallmark of cystic fibrosis.

In one aspect, the composition comprises, consists essentially of, or consists of one or more free amino acids selected from cysteine, proline, glycine, tyrosine and lysine; and optionally, pharmaceutically acceptable carriers, buffers, electrolytes, adjuvants, excipients, and/or an additional therapeutic agent. In certain embodiments, the composition comprises, consists essentially of, or consists of the free amino acids cysteine, proline, glycine, tyrosine and lysine. In certain embodiments, the composition consists essentially of, or consists of only the specified free amino acids and no other free amino acids, or a negligible amount of other free amino acids. The compositions include, in certain embodiments, derivatives of the amino acids that are derivatives of "natural" or "non-natural" amino acids. The compositions include, in certain embodiments, salts and/or prodrugs of the amino acids. In certain embodiments, the composition comprises, consists essentially of, or consists of the free amino acids cysteine, proline, glycine, tyrosine and lysine. In certain embodiments, the composition further comprises, consists essentially of, or consists of one or more of the free amino acids selected from cysteine, proline, glycine, tyrosine and lysine. In yet another aspect, the composition comprises, consists essentially of, or consists of two or more, three or more, four or more, or all five free amino acids selected from cysteine, proline, glycine, tyrosine and lysine; and optionally, pharmaceutically acceptable carriers, buffers, electrolytes, adjuvants, excipients, and/or an additional therapeutic agent. In yet another aspect, the composition comprises, consists essentially of, or consists of free amino acids cysteine and proline and at least one additional free amino acid selected from glycine, tyrosine and/or lysine; and optionally, pharmaceutically acceptable carriers, buffers, electrolytes, adjuvants, excipients, and/or an additional therapeutic agent.

In one aspect, the composition comprises, consists essentially of, or consists of one or more free amino acids selected from threonine and lysine; and optionally, pharmaceutically acceptable carriers, buffers, electrolytes, adjuvants, excipients, and/or an additional therapeutic agent. In certain embodiments, the composition comprises, consists essentially of, or consists of the free amino acids threonine and lysine. In certain embodiments, the composition consists essentially of, or consists of only the specified free amino acids and no other free amino acids, or a negligible amount of other free amino acids. The compositions include, in certain embodiments, derivatives of the amino acids that are derivatives of "natural" or "non-natural" amino acids. The compositions include, in certain embodiments, salts and/or prodrugs of the amino acids. In certain embodiments, the composition comprises, consists essentially of, or consists of the free amino acids threonine and lysine. In certain embodiments, the composition further comprises, consists essentially of, or consists of one or more of the free amino acids selected from threonine and lysine.

In one aspect, the composition comprises, consists essentially of, or consists of one or more free amino acids selected from cysteine, proline and valine; and optionally, pharmaceutically acceptable carriers, buffers, electrolytes, adjuvants, excipients, and/or an additional therapeutic agent. In certain embodiments, the composition comprises, consists essentially of, or consists of the free amino acids cysteine, proline and valine. In certain embodiments, the composition consists essentially of, or consists of only the specified free amino acids and no other free amino acids, or a negligible amount of other free amino acids. The compositions include, in certain embodiments, derivatives of the amino acids that are derivatives of "natural" or "non-natural" amino acids. The compositions include, in certain embodiments, salts and/or prodrugs of the amino acids. In certain embodiments, the composition comprises, consists essentially of, or consists of the free amino acids cysteine, proline and valine. In certain embodiments, the composition further comprises, consists essentially of, or consists of one or more of the free amino acids selected from cysteine, proline and valine. In yet another aspect, the composition comprises, consists essentially of, or consists of two or more, or all three free amino acids selected from cysteine, proline and valine; and optionally, pharmaceutically acceptable carriers, buffers, electrolytes, adjuvants, excipients, and/or an additional therapeutic agent.

In one aspect, the composition comprises, consists essentially of, or consists of one or more free amino acids selected from cysteine, proline, glycine, and valine; and optionally, pharmaceutically acceptable carriers, buffers, electrolytes, adjuvants, excipients, and/or an additional therapeutic agent. In certain embodiments, the composition comprises, consists essentially of, or consists of the free amino acids cysteine, proline, glycine, and valine. In certain embodiments, the composition consists essentially of, or consists of only the specified free amino acids and no other free amino acids, or a negligible amount of other free amino acids. The compositions include, in certain embodiments, derivatives of the amino acids that are derivatives of "natural" or "non-natural" amino acids. The compositions include, in certain embodiments, salts and/or prodrugs of the amino acids. In certain embodiments, the composition comprises, consists essentially of, or consists of the free amino acids cysteine, proline, glycine, and valine. In certain embodiments, the composition further comprises, consists essentially of, or consists of one or more of the free amino acids selected from cysteine, proline, glycine, and valine. In yet another aspect, the composition comprises, consists essentially of, or consists of two or more, three or more, or all four free amino acids selected from cysteine, proline, glycine, and valine; and optionally, pharmaceutically acceptable carriers, buffers, electrolytes, adjuvants, excipients, and/or an additional therapeutic agent.

In one aspect, the composition comprises, consists essentially of, or consists of one or more free amino acids selected from cysteine, proline, valine and tyrosine; and optionally, pharmaceutically acceptable carriers, buffers, electrolytes, adjuvants, excipients, and/or an additional therapeutic agent. In certain embodiments, the composition comprises, consists essentially of, or consists of the free amino acids cysteine, proline, valine and tyrosine. In certain embodiments, the composition consists essentially of, or consists of only the specified free amino acids and no other free amino acids, or a negligible amount of other free amino acids. The compositions include, in certain embodiments, derivatives of the amino acids that are derivatives of "natural" or "non-natural" amino acids. The compositions include, in certain embodiments, salts and/or prodrugs of the amino acids. In certain embodiments, the composition comprises, consists essentially of, or consists of the free amino acids cysteine, proline, valine and tyrosine. In certain embodiments, the composition further comprises, consists essentially of, or consists of one or more of the free amino acids selected from cysteine, proline, valine and tyrosine. In yet another aspect, the composition comprises, consists essentially of, or consists of two or more, three or more, or all four free amino acids selected from cysteine, proline, valine and tyrosine; and optionally, pharmaceutically acceptable carriers, buffers, electrolytes, adjuvants, excipients, and/or an additional therapeutic agent.

In one aspect, the composition comprises, consists essentially of, or consists of one or more free amino acids selected from glycine, leucine and lysine; and optionally, pharmaceutically acceptable carriers, buffers, electrolytes, adjuvants, excipients, and/or an additional therapeutic agent. In certain embodiments, the composition comprises, consists essentially of, or consists of the free amino acids glycine, leucine and lysine. In certain embodiments, the composition consists essentially of, or consists of only the specified free amino acids and no other free amino acids, or a negligible amount of other free amino acids. The compositions include, in certain embodiments, derivatives of the amino acids that are derivatives of "natural" or "non-natural" amino acids. The compositions include, in certain embodiments, salts and/or prodrugs of the amino acids. In certain embodiments, the composition comprises, consists essentially of, or consists of the free amino acids glycine, leucine and lysine. In certain embodiments, the composition further comprises, consists essentially of, or consists of one or more of the free amino acids selected from glycine, leucine and lysine. In yet another aspect, the composition comprises, consists essentially of, or consists of two or more, or all three free amino acids selected from glycine, leucine and lysine; and optionally, pharmaceutically acceptable carriers, buffers, electrolytes, adjuvants, excipients, and/or an additional therapeutic agent.

In one aspect, the composition comprises, consists essentially of, or consists of one or more free amino acids selected from glycine, leucine, lysine, tyrosine, arginine and isoleucine; and optionally, pharmaceutically acceptable carriers, buffers, electrolytes, adjuvants, excipients, and/or an additional therapeutic agent. In certain embodiments, the composition comprises, consists essentially of, or consists of the free amino acids glycine, leucine, lysine, tyrosine, arginine and isoleucine. In certain embodiments, the composition consists essentially of, or consists of only the specified free amino acids and no other free amino acids, or a negligible amount of other free amino acids. The compositions include, in certain embodiments, derivatives of the amino acids that are derivatives of "natural" or "non-natural" amino acids. The compositions include, in certain embodiments, salts and/or prodrugs of the amino acids. In certain embodiments, the composition comprises, consists essentially of, or consists of the free amino acids glycine, leucine, lysine, tyrosine, arginine and isoleucine. In certain embodiments, the composition further comprises, consists essentially of, or consists of one or more of the free amino acids selected from glycine, leucine, lysine, tyrosine, arginine and isoleucine. In yet another aspect, the composition comprises, consists essentially of, or consists of two or more, three or more, four or more, five or more, or all six free amino acids selected from glycine, leucine, lysine, tyrosine, arginine and isoleucine; and optionally, pharmaceutically acceptable carriers, buffers, electrolytes, adjuvants, excipients, and/or an additional therapeutic agent.

Non-limiting examples of compositions comprising amino acids that increase translocation of CFTR to the plasma membrane are provided in Table B below.

TABLE B

Compositions Comprising Amino Acids

| Composition Name | Amino Acids |
|---|---|
| CF2AA | Threonine, lysine |
| CF3AA-2 | Cysteine, proline, valine |
| CF4AA | Cysteine, proline, glycine, valine |
| CF4AA-2 | Cysteine, proline, valine, tyrosine |
| CF5AA-3 | Cystine, proline, glycine, tyrosine, lysine |
| CF4AA-3 | Histidine, tryptophan, aspartic acid, phenylalanine |
| CF3AA | Glycine, leucine, lysine |
| CF4AA-4 | Cysteine, proline, glycine, lysine |
| CF6AA-3 | Glycine, leucine, lysine, tyrosine, arginine, isoleucine |

Each of the free amino acids, if present in the composition, may be present in, for example, the following concentrations: proline at about 0.4 to about 1.5, about 0.7 to about 1.3, about 0.9 to about 1.1 grams/liter, or about 1.5 to about 1.7 grams/liter; glutamic acid at about 0.7 to about 1.7, about 0.9 to about 1.5, about 1.1 to about 1.3 grams/liter, or about 1.5 to about 1.7 grams/liter; glutamine at about 0.6 to about 1.6, about 0.8 to about 1.4, about 1.0 to about 1.2 grams/liter, or about 1.5 to about 1.7 grams/liter; leucine at about 0.05 to about 0.4, about 0.1 to about 0.3 grams/liter, or about 1.5 to about 1.7 grams/liter; alanine at about 0.4 to about 1.5, about 0.7 to about 1.3, at about 1.1 to about 2.1, about 1.3 to about 1.9, or about 1.5 to about 1.7 grams/liter; aspartic acid at about 0.4 to about 1.5, about 0.7 to about 1.3, at about 1.1 to about 2.1, about 1.3 to about 1.9, or about 1.5 to about 1.7 grams/liter; phenylalanine at 0.4 to about 1.5, about 0.7 to about 1.3, at about 1.1 to about 2.1, about 1.3 to about 1.9, or about 1.5 to about 1.7 grams/liter; histidine at 0.4 to about 1.5, about 0.7 to about 1.3, at about 1.1 to about 2.1, about 1.3 to about 1.9, or about 1.5 to about 1.7 grams/liter; threonine at about 0.4 to about 1.5, about 0.7 to about 1.3, about 0.9 to about 1.1 grams/liter, or about 1.5 to about 1.7 grams/liter; isoleucine at 0.4 to about 1.5, about 0.7 to about 1.3, at about 1.1 to about 2.1, about 1.3 to about 1.9, or about 1.5 to about 1.7 grams/liter; asparagine at 0.4 to about 1.5, about 0.7 to about 1.3, at about 1.1 to about 2.1, about 1.3 to about 1.9, or about 1.5 to about 1.7 grams/liter; tryptophan at 0.4 to about 1.5, about 0.7 to about 1.3, at about 1.1 to about 2.1, about 1.3 to about 1.9, or about 1.5 to about 1.7 grams/liter.

In certain embodiments, the amino acids of the composition are free amino acids. In certain embodiments, the amino acids of the composition are L-amino acids. In certain embodiments, the amino acids of the composition are D-amino acids. In certain embodiments, the amino acids of the composition are a combination of D- and L-amino acids.

In certain embodiments, the amino acids of the compositions described herein may be prodrugs of the free amino acids. The term "prodrugs" refers to compounds that have cleavable groups and become by solvolysis or under physiological conditions the compounds described herein, which are pharmaceutically active in vivo.

In certain embodiments, the amino acids of the compositions described herein may be salts of amino acids (i.e., amino acid salts). Amino acids may be in salt form with cations (e.g., salts of amino acids with negatively charged side chains in solution (e.g., glutamate and aspartate)), anions (salts of amino acids with positively charged side chains in solution (e.g., lysine, arginine, histidine)), and inorganic compounds. Exemplary amino acid salts are listed in Fleck M and Petrosyan A M, *Salts of Amino Acids*, 1$^{st}$ Ed; Springer International Publishing, 2014, which is herein incorporated by reference.

In certain embodiments, the composition further comprises water.

In certain embodiments, the composition further comprises a buffer. Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

In certain embodiments, phosphate ions, such as $H_2PO_4^-$, $HPO_4^{2-}$, and $PO_4^{3-}$, are used to buffer the composition of the subject invention. In certain embodiments, the therapeutic composition uses $HCO_3^-$ or $CO_3^{2-}$ as a buffer. In other embodiments, the therapeutic composition does not use $HCO_3^-$ or $CO_3^{2-}$ as a buffer.

In certain embodiments, the composition comprises one or more electrolytes selected from, for example, $Na^+$; $K^+$; $HCO_3^-$; $CO_3^{2-}$; $Ca^{2+}$; $Mg^{2+}$; $Fe^{2+}$; $Cl^-$; phosphate ions, such as $H_2PO_4^-$, $HPO_4^{2-}$, and $PO_4^{3-}$; zinc; iodine; copper; iron; selenium; chromium; and molybdenum. In an alternative embodiment, the composition does not contain $HCO_3^-$ or $CO_3^{2-}$. In another alternative embodiment, the composition comprises $HCO_3^-$ and $CO_3^{2-}$ at a total concentration of less than 5 mg/l, or concentrations lower than 5 mg/l. In certain embodiments, the composition does not contain electrolytes. In certain embodiments, the composition does not contain carbohydrates (e.g., di-, oligo-, or polysaccharides). In certain alternative embodiments the composition does not comprise one or more, or any, of $Na^+$; $K^+$; $HCO_3^-$; $CO_3^{2-}$; $Ca^{2+}$; $Mg^{2+}$; $Fe_2$; $Cl^-$; phosphate ions, such as $H_2PO_4^-$, $HPO_4^{2-}$, and $PO_4^{3-}$; zinc; iodine; copper; iron; selenium; chromium; and molybdenum.

In certain embodiments, the composition further comprises sugars, vitamins, electrolytes, minerals, proteins, or lipids. In certain embodiments, the composition further comprises sugars. In certain embodiments, the composition further comprises vitamins. In certain embodiments, the composition further comprises electrolytes. In certain embodiments, the composition further comprises minerals. In certain embodiments, the composition further comprises proteins. In certain embodiments, the composition further comprises lipids.

In certain embodiments, the composition does not contain one or more of the ingredients selected from oligo-, polysaccharides, and carbohydrates; oligo-, or polypeptides or proteins; lipids; small-, medium-, and/or long-chain fatty acids; and/or food containing one or more above-mentioned nutrients.

The composition may have a pH ranging from about 2.5 to about 8.5. In certain embodiments, the pH of the composition ranges from about 2.5 to about 6.5, about 3.0 to about 6.0, about 3.5 to about 5.5, about 3.9 to about 5.0, or about 4.2 to about 4.6. In other embodiments, the pH of the composition ranges from about 6.5 to about 8.5, about 7.0 to about 8.0, or about 7.2 to about 7.8. In certain embodiments, the composition has a pH from, for example, about 2.5 to about 8.5. In certain embodiments, the composition has a pH from about 2.5 to about 6.5, about 2.5 to about 6.0, about 3.0 to about 6.0, about 3.5 to about 6.0, about 3.9 to about 6.0, about 4.2 to about 6.0, about 3.5 to about 5.5, about 3.9 to about 5.0, or about 4.2 to about 4.6. In other embodiments, the pH is about 6.5 to about 8.5, about 7.0 to about 8.5, about 7.0 to about 8.0, about 7.2 to about 8.0, or about 7.2 to about 7.8. In certain embodiments, the pH is about 7.3 to about 7.5. In certain embodiments, the pH is about 7.3 to about 7.4. In certain embodiments, the pH is about 7.4 to about 7.5. In certain embodiments, the pH is about 7.4.

In certain embodiments, the total osmolarity of the composition is from about 100 mosm to 280 mosm, or any value therebetween. In certain embodiments, the total osmolarity is from about 150 msom to 260 mosm. In another embodiment, the composition has a total osmolarity that is any value lower than 280 mosm.

In certain embodiments, the composition is sterile.

Compositions described herein can be prepared by any method known in the art of pharmacology. In general, such preparatory methods include bringing compounds of the compositions described herein (i.e., the free amino acid(s)) into association with a carrier or excipient, and/or one or more other accessory ingredients, and then, if necessary and/or desirable, shaping, and/or packaging the product into a desired single- or multi-dose unit.

Relative amounts of the active ingredient/s, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in enhancing the activity of CFTR in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compositions described herein can be administered concurrently with, prior to, or subsequent to one or more additional pharmaceutical agents or therapeutic agents, which are different from the compound or composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, lung disease, or metabolic disorder). In certain embodiments, the additional pharmaceutical agent is useful for treating a lung disease. In certain embodiments, the additional pharmaceutical agent is useful for treating cystic fibrosis. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the compositions are administered concurrently with, prior to, or subsequent to one or more additional therapeutic agents, wherein the additional therapeutic agent is a CFTR potentiator, corrector, or read-through agent. A "CFTR potentiator" is a compound that increases the function of a CFTR on the plasma membrane of a cell. These compounds may be useful for treating cystic fibrosis mutations that result in CFTR proteins that are correctly trafficked to the plasma membrane, but do not function properly (e.g., channel gating is defective, ATP binding is reduced or abrogated, and/or chloride transport is reduced). In certain embodiments, the CFTR potentiator is ivacaftor (VX-770, KALYDECO®). A "CFTR corrector" is a compound that improves the intracellular processing and translocation of mutant CFTR, allowing more protein to reach the plasma membrane. In certain embodiments, the CFTR corrector is lumacaftor (VX-809, ORKAMBI®). In certain embodiments, the CFTR corrector is tezacaftor (VX-661). A "CFTR read-through agent" is a compound that promotes transcription in the presence of a premature termination codon (PTC) mutation resulting from a point mutation in the CFTR gene sequence.

Normally, the PTC would result in a truncated CFTR protein which is not properly processed and/or is malfunctioning (e.g., channel gating is defective, ATP binding is reduced or abrogated, and/or chloride transport is reduced). In certain embodiments, the CFTR read-through agent is ataluren (TRANSLARNA™). In certain embodiments, a composition comprising amino acids as described herein is administered in combination with ivacaftor. In certain embodiments, a composition comprising amino acids as described herein is administered in combination with lumacaftor. In certain embodiments, a composition comprising amino acids as described herein is administered in combination with ataluren. In certain embodiments, a composition comprising amino acids as described herein is administered in combination with ivacaftor and lumacaftor. In certain embodiments, a composition comprising amino acids as described herein is administered in combination with ivacaftor and ataluren. In certain embodiments, a composition comprising amino acids as described herein is administered in combination with lumacaftor and ataluren. In certain embodiments, the compositions are administered alone, i.e., are not administered concurrently with, prior to, or subsequent to one or more additional pharmaceutical agents or therapeutic agents. In certain embodiments, the compositions are administered in the absence of a CFTR potentiator, corrector, or read-through agent.

Solid dosage forms for oral administration include capsules, tablets, pills, powders and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

In certain embodiments, a composition comprising amino acids described herein may be provided in powdered form and reconstituted for administration to a subject. A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

Methods for Increasing Translocation of CFTR to the Plasma Membrane

The present disclosure provides compositions for use for increasing the translocation of the cystic fibrosis transmembrane conductance regulator (CFTR) protein from the cytoplasm to the plasma membrane. In general, without wishing to be bound by any particular theory, mutations in the CFTR protein (e.g., Phe508del) may disrupt correct processing, folding, and/or trafficking to the plasma membrane, resulting in a lower number of CFTR proteins on the plasma membrane and impaired chloride ion transport function in cells expressing the mutated CFTR protein. Impaired chloride ion transport results in an imbalanced osmotic profile, such that water is not being drawn out of the cells expressing the mutated CFTR protein via osmosis due to the abnormally high intracellular concentration of chloride ions. This results in formation of a thick mucus layer covering the cells, a hallmark of cystic fibrosis.

Thus, in one aspect, the present disclosure provides a method for increasing the number of CFTR proteins on the plasma membrane of a cell, the method comprising contacting the cell with an effective amount of a composition comprising amino acids of the present disclosure. In certain embodiments, the cell is an epithelial cell. In certain embodiments, the epithelial cell is a small intestine epithelial cell or lung epithelial cell. In certain embodiments, the epithelial cell is a lung epithelial cell. In certain embodiments, the lung epithelial cell is a bronchial epithelial cell.

The bronchial epithelial cell may be a normal human bronchial epithelial cell (NHBE) or a diseased human bronchial epithelial cell (DHBE). A diseased human bronchial epithelial cell may be obtained from a human donor diagnosed with a lung disease (e.g., asthma, COPD, cystic fibrosis). In certain embodiments, the bronchial epithelial cells are expressing wild-type CFTR. In certain embodiments, the bronchial epithelial cells are expressing mutant CFTR. In certain embodiments, the bronchial epithelial cells are expressing both wild-type and mutant CFTR (i.e., one allele in the CFTR gene encodes wild-type CFTR and the second allele contains a mutation (e.g., Phe508del CFTR)). In certain embodiments, the bronchial epithelial cells are expressing only the Phe508del mutant CFTR. The cells may be present in vitro, in vivo, or ex vivo.

In certain embodiments, the number of wild-type CFTR proteins on the plasma membrane increases. In certain embodiments, the number of mutant CFTR proteins on the plasma membrane increases. In certain embodiments, the number of Gly542X mutant CFTR proteins on the plasma membrane increases, where X is any amino acid. In certain embodiments, the number of Gly551Asp mutant CFTR proteins on the plasma membrane increases. In certain embodiments, the number of Arg553X mutant CFTR proteins on the plasma membrane increases, where X is any amino acid. In certain embodiments, the number of Arg117His mutant CFTR proteins on the plasma membrane increases. In certain embodiments, the number of 120del23 mutant CFTR proteins on the plasma membrane increases. In certain embodiments, the number of Phe508del mutant CFTR proteins on the plasma membrane increases. In certain embodiments, the number of CFTR proteins that are at least 90%, at least 95%, at least 98%, at least 99%, or at least 99.5% identical to the amino acid sequence of wild-type CFTR as provided by SEQ ID NO: 1 on the plasma membrane increases. In certain embodiments, the number of CFTR proteins that are at least 90%, at least 95%, at least 98%, at least 99%, or at least 99.5% identical to the amino acid sequence of Phe508del CFTR as provided by SEQ ID NO: 2 on the plasma membrane increases.

In certain embodiments, the present disclosure provides a method for increasing the number of CFTR proteins on the plasma membrane of a cell, the method comprising contacting the cell with an effective amount of a composition described herein. In certain embodiments, the composition comprises, consists essentially of, or consists of one or more free amino acids selected from threonine and lysine. In certain embodiments, the composition comprises, consists essentially of, or consists of one or more free amino acids selected from cysteine, proline and valine. In certain embodiments, the composition comprises, consists essentially of, or consists of one or more free amino acids selected from cysteine, proline, glycine, and valine. In certain embodiments, the composition comprises, consists essentially of, or consists of one or more free amino acids selected from cysteine, proline, valine and tyrosine. In certain embodiments, the composition comprises, consists essentially of, or consists of one or more free amino acids selected from cysteine, proline, glycine, tyrosine and lysine. In certain embodiments, the composition comprises, consists essentially of, or consists of one or more free amino acids selected from glycine, leucine and lysine. In certain embodiments, the composition comprises, consists essentially of, or consists of one or more free amino acids selected from glycine, leucine, lysine, tyrosine, arginine and isoleucine. In yet another aspect, the composition comprises, consists essentially of, or consists of free amino acids cysteine and proline and at least one additional free amino acid selected from glycine, tyrosine and/or lysine; and optionally, buffers, electrolytes, adjuvants, and/or excipients.

By "negligible amount" it is meant that the amino acid present has no effect on the CFTR protein. Or, in certain embodiments, even if the amino acid is present in the composition, it is not present in an amount that would affect the translocation of CFTR to the plasma membrane, chloride ion transport, or the therapeutic effect of treating a subject in need thereof. In certain embodiments, a negligible amount is an amount wherein the total concentration of the amino acid is less than 100 mg/l, 50 mg/l, 10 mg/l, 5 mg/l, 1 mg/l, 0.5 mg/l, 0.1 mg/l, or 0.01 mg/l. In certain embodiments, a negligible amount is an amount wherein the total concentration of the amino acid is less than 100 mg/l. In certain embodiments, a negligible amount is an amount wherein the total concentration of the amino acid is less than 50 mg/l. In certain embodiments, a negligible amount is an amount wherein the total concentration of the amino acid is less than 10 mg/l. In certain embodiments, a negligible amount is an amount wherein the total concentration of the amino acid is less than 5 mg/l. In certain embodiments, a negligible amount is an amount wherein the total concentration of the amino acid is less than 1 mg/l. In certain embodiments, a negligible amount is an amount wherein the total concentration of the amino acid is less than 0.5 mg/l. In certain embodiments, a negligible amount is an amount wherein the total concentration of the amino acid is less than 0.1 mg/l. In certain embodiments, a negligible amount is an amount wherein the total concentration of the amino acid is less than 0.01 mg/l. It is understood that a negligible amount is an amount greater zero.

In certain embodiments, compositions of the present disclosure comprise one or more free amino acids that are essential (e.g., necessary) for increasing the translocation of CFTR to the plasma membrane. In certain embodiments, compositions of the present disclosure may include one or more free amino acids that are not essential for increasing the translocation of CFTR to the plasma membrane (i.e., do not directly stabilize CFTR), but may instead provide alternative beneficial properties to the composition (e.g., maintain a specific pH or osmolarity).

In one aspect, the method of increasing the number of CFTR proteins on the plasma membrane of a cell involves increasing the translocation of CFTR from the cytoplasm of the cell to the cell membrane, the method comprising contacting the cell with an effective amount of a composition comprising amino acids of the present disclosure. In one embodiment, the method leads to an increase in the number of CFTR proteins on the plasma membrane of the treated cell. An increase in the number of CFTR proteins on the plasma membrane can be determined by comparing the cells contacted with a composition comprising amino acids described herein to untreated cells (e.g., control cells). For example, a western blot may be used to compare the presence and amount of CFTR in membrane vesicles isolated from epithelial cells contacted with a composition comprising amino acids as described herein versus the amount of CFTR in membrane vesicles isolated from untreated epithelial cells (e.g., control cells). Conducting a western blot analysis as described herein is within the ability of a person of ordinary skill in the art. Additional related techniques that may be used to determine the expression level of the CFTR protein in a sample include dot blot analysis, immunohistochemistry, immunocytochemistry, and enzyme-linked immunosorbent assay (ELISA), among others.

The CFTR protein is an ABC transporter protein that functions as an ATP-gated ion channel. When activated, CFTR allows chloride ions (Cl⁻), and other negatively charged ions such as thiocyanate ([SCN]⁻), to flow down their electrochemical gradient (e.g., passive diffusion or passive transport). Mutations in CFTR, such as, for example, Gly551X, where X represents any amino acid (e.g., Gly551Asp), result in a CFTR protein characterized by defective ion channel gating function. The most common CFTR mutation, Phe508del, results in a CFTR protein that lacks the codon for phenylalanine 508 and cannot properly fold or traffick to the plasma membrane. Thus, in one aspect, the present disclosure provides a method for increasing the number of CFTR proteins on the plasma membrane of a cell and increasing the transport of chloride ions across the cell membrane (e.g., export of chloride ions from the cell), the method comprising contacting a cell with a composition comprising amino acids as described herein.

Thus, in one aspect, the present disclosure provides a method for increasing chloride ion export from a cell, the method comprising contacting the cell with an effective amount of a composition described herein. In certain embodiments, the composition comprises, consists essentially of, or consists of one or more free amino acids selected from threonine and lysine. In certain embodiments, the composition comprises, consists essentially of, or consists of one or more free amino acids selected from cysteine, proline and valine. In certain embodiments, the composition comprises, consists essentially of, or consists of one or more free amino acids selected from cysteine, proline, glycine, and valine. In certain embodiments, the composition comprises, consists essentially of, or consists of one or more free amino acids selected from cysteine, proline, valine and tyrosine. In certain embodiments, the composition comprises, consists essentially of, or consists of one or more free amino acids selected from cysteine, proline, glycine, tyrosine and lysine. In certain embodiments, the composition comprises, consists essentially of, or consists of one or more free amino acids selected from glycine, leucine and lysine. In certain embodiments, the composition comprises, consists essentially of, or consists of one or more free amino acids selected from glycine, leucine, lysine, tyrosine, arginine and isoleucine. In yet another embodiment, the composition comprises, consists essentially of, or consists of free amino acids cysteine and proline and at least one additional free amino acid selected from glycine, tyrosine and/or lysine; and optionally, buffers, electrolytes, adjuvants, and/or excipients.

In certain embodiments, the export of chloride from a cell is further enhanced by contacting the cell with a CFTR potentiator, corrector, or read-through agent. In certain embodiments, the export of chloride from a cell is increased by contacting the cell with a combination therapy comprising a composition described herein and a CFTR potentiator. In certain embodiments, the export of chloride from a cell is increased by contacting the cell with a combination therapy comprising a composition described herein and a CFTR corrector. In certain embodiments, the export of chloride from a cell is increased by contacting the cell with a combination therapy comprising a composition described herein and a CFTR read-through agent. In certain embodiments, the export of chloride from a cell is increased by contacting the cell with a combination therapy comprising a composition described herein and ivacaftor.

The flow of ions, such as chloride ions, across a membrane is one biological mechanism used to regulate the flow of water across a semi-permeable membrane (e.g., a cell membrane). Osmosis describes a process by which solvent (e.g., water) molecules flow from an area of low solute concentration to an area of higher solute concentration to balance the concentration on each side of a semi-permeable membrane (e.g., passive diffusion of water). When the chloride ion concentration in a cell increases due to malfunction of the CFTR, water molecules do not flow out of the cell and into the surrounding mucus membrane, resulting in the formation of thick mucus. Thus, in a further aspect, the present disclosure provides methods and compositions for increasing the flow of water out of a cell (e.g., osmosis), the method comprising contacting a cell with a composition comprising amino acids as described herein.

Thus, in one aspect, the present disclosure provides a method for increasing the export of water from a cell, the method comprising contacting a cell with a composition described herein. In certain embodiments, the composition comprises, consists essentially of, or consists of one or more free amino acids selected from threonine and lysine. In certain embodiments, the composition comprises, consists essentially of, or consists of one or more free amino acids selected from cysteine, proline and valine. In certain embodiments, the composition comprises, consists essentially of, or consists of one or more free amino acids selected from cysteine, proline, glycine, and valine. In certain embodiments, the composition comprises, consists essentially of, or consists of one or more free amino acids selected from cysteine, proline, valine and tyrosine. In certain embodiments, the composition comprises, consists essentially of, or consists of one or more free amino acids selected from cysteine, proline, glycine, tyrosine and lysine. In certain embodiments, the composition comprises, consists essentially of, or consists of one or more free amino acids selected from glycine, leucine and lysine. In certain embodiments, the composition comprises, consists essentially of, or consists of one or more free amino acids selected from glycine, leucine, lysine, tyrosine, arginine and isoleucine. In yet another embodiment, the composition comprises, consists essentially of, or consists of free amino acids cysteine and proline and at least one additional free amino acid selected from glycine, tyrosine and/or lysine; and optionally, buffers, electrolytes, adjuvants, and/or excipients.

In certain embodiments, the export of water from a cell is further enhanced by contacting the cell with a CFTR potentiator, corrector, or read-through agent. In certain embodiments, the export of water from a cell is increased by contacting the cell with a combination therapy comprising a composition described herein and a CFTR potentiator. In certain embodiments, the export of water from a cell is increased by contacting the cell with a combination therapy comprising a composition described herein and a CFTR corrector. In certain embodiments, the export of water from a cell is increased by contacting the cell with a combination therapy comprising a composition described herein and a CFTR read-through agent. In certain embodiments, the export of water from a cell is increased by contacting the cell with a combination therapy comprising a composition described herein and ivacaftor. Methods for treatment of cystic fibrosis As described above, the flow of chloride ions through the cystic fibrosis transmembrane conductance regulator (CFTR) protein is crucial for maintenance of fluid levels in the cell and surrounding mucosal membrane, particularly in the lungs and small intestines. Mutations in the CFTR protein (e.g., Phe508del) that disrupt CFTR processing, folding, and trafficking to the plasma membrane result in a lower number of functioning CFTR proteins on the plasma membrane. The biological result is the build-up of a thick mucus layer covering the epithelial cell layer, promoting bacterial growth and preventing epithelial cells from obtaining nutrients from the surrounding fluid. Ultimately, respiratory and lung diseases, such as cystic fibrosis, may develop in patients carrying one or more CFTR gene mutations.

The subject can be, for example, a human suffering from a lung disease. In certain embodiments, the subject is suffering from cystic fibrosis. In certain embodiments, the underlying genetic cause of the cystic fibrosis may be the Phe508del mutation in one or more alleles of the CFTR gene. The human may also be suffering from additional complications that often occur concurrently with cystic fibrosis, such as bacterial infections, viral infections, asthma, and chronic respiratory failure, among others. Thus, the compositions comprising amino acids disclosed herein may also be useful in managing the symptoms and other complications in a subject with cystic fibrosis.

In certain embodiments, the methods described herein lead to increased survival of a patient suffering from a lung disease (e.g., cystic fibrosis). The methods and compositions described herein may also be useful for improving the therapeutic outcome of patients with cystic fibrosis.

Thus, in one aspect, the present disclosure provides compositions for use for treatment of cystic fibrosis, wherein the compositions are administered to a subject in need thereof (e.g., a subject with cystic fibrosis). In certain embodiments, a subject is suffering from cystic fibrosis in which wild-type CFTR of SEQ ID NO: 1 is present. In certain embodiments, the subject is suffering from cystic fibrosis in which a CFTR protein that is at least 90%, at least 95%, at least 98%, at least 99%, or at least 99.5% identical to the amino acid sequence of wild-type CFTR as provided by SEQ ID NO: 1 is present. In certain embodiments, the subject is suffering from cystic fibrosis in which mutant CFTR is present. In certain embodiments, the subject is suffering from cystic fibrosis in which the mutant CFTR is a Gly542X, Gly551Asp, Arg553X, Arg117His, 120del23, or Phe508del mutant, wherein X represents any amino acid. In certain embodiments, the subject is suffering from cystic fibrosis in which both wild-type CFTR and mutant CFTR are present. In certain embodiments, the subject is suffering from cystic fibrosis in which a CFTR protein that is at least 90%, at least 95%, at least 98%, at least 99%, or at least 99.5% identical to the amino acid sequence of Phe508del CFTR as provided by SEQ ID NO: 2 is present. In certain embodiments, the subject is suffering from cystic fibrosis in which the mutant CFTR is Phe508del CFTR of SEQ ID NO: 2. In certain embodiments, the subject is suffering from cystic fibrosis in which both wild-type CFTR of SEQ ID NO: 1 and Phe508del CFTR of SEQ ID NO: 2 are present. The compositions described herein may be administered with one or more additional therapeutic agents, e.g., combination therapy, to further increase the therapeutic benefit of the compositions described herein.

In a further aspect, the present disclosure provides a method for treating cystic fibrosis, the method comprising administering to a subject in need thereof a composition described herein. In certain embodiments, the composition comprises, consists essentially of, or consists of one or more free amino acids selected from threonine and lysine. In certain embodiments, the composition comprises, consists essentially of, or consists of one or more free amino acids selected from cysteine, proline and valine. In certain embodiments, the composition comprises, consists essentially of, or consists of one or more free amino acids selected from cysteine, proline, glycine, and valine. In certain embodiments, the composition comprises, consists essentially of, or consists of one or more free amino acids selected from cysteine, proline, valine and tyrosine. In certain embodiments, the composition comprises, consists essentially of, or consists of one or more free amino acids selected from cysteine, proline, glycine, tyrosine and lysine. In certain embodiments, the composition comprises, consists essentially of, or consists of one or more free amino acids selected from glycine, leucine and lysine. In certain embodiments, the composition comprises, consists essentially of, or consists of one or more free amino acids selected from glycine, leucine, lysine, tyrosine, arginine and isoleucine. In yet another embodiment, the composition comprises, consists essentially of, or consists of free amino acids cysteine and proline and at least one additional free amino acid selected from glycine, tyrosine and/or lysine; and optionally, buffers, electrolytes, adjuvants, and/or excipients.

In certain embodiments, the composition further comprises a CFTR potentiator, corrector, or read-through agent. In certain embodiments, the composition further comprises a CFTR potentiator. In certain embodiments, the composition further comprises a CFTR corrector. In certain embodiments, the composition further comprises a CFTR read-through agent. In certain embodiments, the composition further comprises ivacaftor. In certain embodiments, the composition does not further comprise a CFTR potentiator, corrector, or read-through agent.

SYMDEKO® (tezacaftor/ivacaftor and ivacaftor) is indicated for the treatment of patients with cystic fibrosis (CF) age 6 years and older who are homozygous for the F308del mutation or who have at least one mutation in the cystic fibrosis transmembrane conductance regulator (CFTR) gene that is responsive to tezacaftor/ivacaftor based on in vitro data and/or clinical evidence. For patients age 6-11 years, weighing <30 kg, the typical dose is 50 ng tezacaftor+75 mg ivacaftor in the morning and 75 mg ivacaftor 12 hours later. For patients age 6-11 years, weighing≥30 kg or patients 12 years and older, the typical dose is 100 mg tezacaftor+150 mg ivacaftor in the morning and 150 mg ivacaftor 12 hours later.

ORKAMBI® (lumacaftor/ivacaftor) is indicated for cystic fibrosis (CF) in patients who are homozygous for the F508del mutation in the CFTR gene. For patients age 6 through 11 years: 2 tablets (each containing lumacaftor 100 mg/ivacaftor 125 mg) every 12 hours. For patients age 12 years and older: 2 tablets (each containing lumacaftor 200 mg/ivacaftor 125 mg) every 12 hours.

KALYDECO® (ivacaftor) is a cystic fibrosis transmembrane conductance regulator (CFTR) potentiator indicated for the treatment of CF in patients age 6 months and older who have one mutation in the CFTR gene that is responsive to ivacaftor potentiation based on clinical and/or in vitro assay data. For patients age 6 months to <6 years, the recommended dose is weight based 5 kg to <7 kg: One 25 mg packet every 12 hours; 7 kg to <14 kg: One 50 mg packet every 12 hours; ≥14 kg: One 75 mg packet every 12 hours.

Ataluren May be Used at a Dose of 40 mg/kg/Day.

It is understood that when used in combination with pharmaceutical formulations described herein, the typical doses may vary. In a particular embodiment of such combination therapy, the dosing of either of, for example, SYMDEKO®, ORKAMBI®, KALYDECO®, or Ataluren may be reduced, either with respect to the dose administered and/or the frequency of administration, when administered in conjunction with a pharmaceutical formulation described herein.

CFTR Gene and Gene Products and CFTR Mutants

As discussed above, the compositions comprising amino acids as described herein effectively increase the translocation of CFTR to the plasma membrane. In particular, the compositions comprising amino acids as described herein can effectively increase the translocation of mutant (e.g., Phe508del) CFTR to the plasma membrane. The compositions result in an increase in the number of CFTR proteins on the plasma membrane, providing a method for increasing chloride ion transport across the epithelial cell membrane to maintain membrane hyperpolarization and transmembrane water transport. These compositions are useful for the treatment of lung diseases, such as cystic fibrosis, or diseases which result from dysregulation of fluid transport in other epithelial cells, such as those in the pancreas and small intestine.

Sequences of the CFTR gene products of interest herein often comprise or consist of sequences encoded by human CFTR genes, although sequences of non-human mammalian homologs may be used in certain embodiments. In general, the sequence of a CFTR protein or CFTR RNA often comprises or consists of a sequence of a human CFTR. In certain embodiments, the sequence of a gene product of a CFTR gene comprises or consists of a naturally occurring sequence. It will be appreciated that a genetic locus may have more than one sequence or allele in a population of individuals. In some embodiments a naturally occurring sequence is a standard sequence. Unless otherwise indicated, a sequence listed in the Reference Sequence (RefSeq) Database as a reference sequence for a protein that is referred to herein by a particular name, abbreviation, or symbol, is considered to be a "standard sequence." If a sequence has been updated subsequent to the time of the present disclosure a version current at the time of the present disclosure or an updated version thereof may be used in certain embodiments. It will be appreciated that a genetic locus may have more than one sequence or allele in a population of individuals. In some embodiments a naturally occurring sequence differs from a standard sequence at one or more amino acid positions. A naturally occurring polynucleotide or polypeptide whose sequence differs from a standard sequence and that performs the normal function(s) of the polynucleotide or polypeptide may be referred to as having a "normal sequence".

The CFTR gene is approximately 189 kb in length and is comprised of 27 exons and 26 introns. In certain embodiments, the CFTR protein is the full-length, wild-type CFTR. The CFTR may be a mammalian (e.g., human) CFTR. In certain embodiments, the sequence of a CFTR or variant thereof used in the compositions and methods described herein comprises the sequence of a naturally occurring CFTR protein or a biologically active variant thereof. A biologically active variant of an androgen receptor protein may contain one or more additions, substitutions, and/or deletions relative to the sequence of a naturally occurring CFTR protein. In some embodiments, the sequence of a CFTR protein comprises a standard CFTR sequence. The full-length CFTR protein is 1480 amino acids in length and has five domains: two transmembrane domains, one intracellular nucleotide binding domain (NBD) connected to each transmembrane domain, and one intracellular regulatory "R" domain. Full-length, wild-type CFTR has the following standard amino acid sequence (GenBank and NCBI Reference Sequence Accession Number: NG_016465.4):

(SEQ ID NO: 1)
MQRSPLEKASVVSKLFFSWTRPILRKGYRQRLELSDIYQIPSVDSADNLS

EKLEREWDRELASKKNPKLINALRRCFFWRFMFYGIFLYLGEVTKAVQPL

LLGRIIASYDPDNKEERSIAIYLGIGLCLLFIVRTLLLHPAIFGLHHIGM

QMRIAMFSLIYKKTLKLSSRVLDKISIGQLVSLLSNNLNKFDEGLALAHF

VWIAPLQVALLMGLIWELLQASAFCGLGFLIVLALFQAGLGRMMMKYRDQ

RAGKISERLVITSEMIENIQSVKAYCWEEAMEKMIENLRQTELKLTRKAA

YVRYFNSSAFFFSGFFVVFLSVLPYALIKGIILRKIFTTISFCIVLRMAV

TRQFPWAVQTWYDSLGAINKIQDFLQKQEYKTLEYNLTTTEVVMENVTAF

WEEGFGELFEKAKQNNNNRKTSNGDDSLFFSNFSLLGTPVLKDINFKIER

GQLLAVAGSTGAGKTSLLMVIMGELEPSEGKIKHSGRISFCSQFSWIMPG

TIKENIIFGVSYDEYRYRSVIKACQLEEDISKFAEKDNIVLGEGGITLSG

GQRARISLARAVYKDADLYLLDSPFGYLDVLTEKEIFESCVCKLMANKTR

ILVTSKMEHLKKADKILILHEGSSYFYGTFSELQNLQPDFSSKLMGCDSF

DQFSAERRNSILTETLHRFSLEGDAPVSWTETKKQSFKQTGEFGEKRKNS

ILNPINSIRKFSIVQKTPLQMNGIEEDSDEPLERRLSLVPDSEQGEAILP

RISVISTGPTLQARRRQSVLNLMTHSVNQGQNIHRKTTASTRKVSLAPQA

NLTELDIYSRRLSQETGLEISEEINEEDLKECFFDDMESIPAVTTWNTYL

RYITVHKSLIFVLIWCLVIFLAEVAASLVVLWLLGNTPLQDKGNSTHSRN

NSYAVIITSTSSYYVFYIYVGVADTLLAMGFFRGLPLVHTLITVSKILHH

KMLHSVLQAPMSTLNTLKAGGILNRFSKDIAILDDLLPLTIFDFIQLLLI

VIGAIAVVAVLQPYIFVATVPVIVAFIMLRAYFLQTSQQLKQLESEGRSP

IFTHLVTSLKGLWTLRAFGRQPYFETLFHKALNLHTANWFLYLSTLRWFQ

MRIEMIFVIFFIAVTFISILTTGEGEGRVGIILTLAMNIMSTLQWAVNSS

IDVDSLMRSVSRVFKFIDMPTEGKPTKSTKPYKNGQLSKVMIIENSHVKK

DDIWPSGGQMTVKDLTAKYTEGGNAILENISFSISPGQRVGLLGRTGSGK

STLLSAFLRLLNTEGEIQIDGVSWDSITLQQWRKAFGVIPQKVFIFSGTF

RKNLDPYEQWSDQEIWKVADEVGLRSVIEQFPGKLDFVLVDGGCVLSHGH

KQLMCLARSVLSKAKILLLDEPSAHLDPVTYQIIRRTLKQAFADCTVILC

EHRIEAMLECQQFLVIEENKVRQYDSIQKLLNERSLFRQAISPSDRVKLF

PHRNSSKCKSKPQIAALKEETEEEVQDTRL

In certain embodiments, the present disclosure provides compositions comprising amino acids useful for increasing the number of CFTR proteins on the plasma membrane. In certain embodiments, the CFTR protein is at least 70%, 80%, 90%, 95%, 96%, 97%, 98%, 99%, 99.5% or more, e.g. 100%, identical in sequence to wild-type CFTR of SEQ ID NO: 1. In certain embodiments, the CFTR protein is at least 70% identical in sequence to wild-type CFTR of SEQ ID NO: 1. In certain embodiments, the CFTR protein is at least 80% identical in sequence to wild-type CFTR of SEQ ID NO: 1. In certain embodiments, the CFTR protein is at least 90% identical in sequence to wild-type CFTR of SEQ ID NO: 1. In certain embodiments, the CFTR protein is at least 95% identical in sequence to wild-type CFTR of SEQ ID NO: 1. In certain embodiments, the CFTR protein is at least 96% identical in sequence to wild-type CFTR of SEQ ID NO: 1. In certain embodiments, the CFTR protein is at least 97% identical in sequence to wild-type CFTR of SEQ ID NO: 1. In certain embodiments, the CFTR protein is at least 98% identical in sequence to wild-type CFTR of SEQ ID NO: 1. In certain embodiments, the CFTR protein is at least 99% identical in sequence to wild-type CFTR of SEQ ID NO: 1. In certain embodiments, the CFTR protein is at least 99.5% identical in sequence to wild-type CFTR of SEQ ID NO: 1. In certain embodiments, the CFTR protein is at least 100% identical in sequence to wild-type CFTR of SEQ ID NO: 1.

In certain embodiments, the CFTR protein is a variant or fragment of the full-length CFTR of SEQ ID NO: 1. The term "variant" also encompasses splice variants of CFTR that result from alternative splicing of the CFTR gene. In certain embodiments, the CFTR variant comprises or consists of a polypeptide that is over at least 50%, 60%, 70%, 80%, 90%, 95%, 96%, 97%, 98%, 99%, 99.5%, or 100% of the full-length CFTR of SEQ ID NO: 1. In certain embodiments, the CFTR variant comprises or consists of a polypeptide that is over at least 50% of the full-length CFTR of SEQ ID NO: 1. In certain embodiments, the CFTR variant comprises or consists of a polypeptide that is over at least 60% of the full-length CFTR of SEQ ID NO: 1. In certain embodiments, the CFTR variant comprises or consists of a polypeptide that is over at least 70% of the full-length CFTR of SEQ ID NO: 1. In certain embodiments, the CFTR variant comprises or consists of a polypeptide that is over at least 80% of the full-length CFTR of SEQ ID NO: 1. In certain embodiments, the CFTR variant comprises or consists of a polypeptide that is over at least 90% of the full-length CFTR of SEQ ID NO: 1. In certain embodiments, the CFTR variant comprises or consists of a polypeptide that is over at least 95% of the full-length CFTR of SEQ ID NO: 1. In certain embodiments, the CFTR variant comprises or consists of a polypeptide that is over at least 96% of the full-length CFTR of SEQ ID NO: 1. In certain embodiments, the CFTR variant comprises or consists of a polypeptide that is over at least 97% of the full-length CFTR of SEQ ID NO: 1. In certain embodiments, the CFTR variant comprises or consists of a polypeptide that is over at least 98% of the full-length CFTR of SEQ ID NO: 1. In certain embodiments, the CFTR variant comprises or consists of a polypeptide that is over at least 99% of the full-length CFTR of SEQ ID NO: 1. In certain embodiments, the CFTR variant comprises or consists of a polypeptide that is over at least 99.5% of the full-length CFTR of SEQ ID NO: 1. In certain embodiments, the CFTR variant comprises or consists of a polypeptide that is over at least 100% of the full-length CFTR of SEQ ID NO: 1. These variants may be biologically active variants of wild-type CFTR, such that the ion channel gating function and/or the chloride transport function of the CFTR is retained in the variant. These variants may be biologically inactive variants of wild-type CFTR, such that the ion channel gating function and/or the chloride transport function of the CFTR is abrogated (e.g., not functional) in the variant.

In certain embodiments, a CFTR protein is a mutant CFTR protein, e.g., the sequence of the protein comprises the sequence of a naturally occurring mutant form of CFTR. The mutant CFTR may be a mammalian (e.g., human) CFTR mutant. The mutant CFTR may result from a nonsense, frameshift, or mRNA splicing mutation. Over 2,000 mutations in the CFTR gene have been discovered, many of which are clinically relevant and/or lead to a disease (e.g., cystic fibrosis) phenotype. See Bobadilla J L et al., 2002, Human Mutation, 19; pp. 575-606, which is herein incorporated by reference, for additional CFTR gene mutations for which administration of a composition of the present disclosure may prove useful. In certain embodiments, the mutant CFTR is a Gly542X, Gly551Asp, Arg553X, Arg117His, 120del23, or Phe508del mutant, wherein X represents any amino acid. In certain embodiments, the mutant CFTR is a Gly542X mutant, wherein X represents any amino acid. In certain embodiments, the mutant CFTR is a Gly551Asp mutant. In certain embodiments, the mutant CFTR is a Arg553X mutant, wherein X represents any amino acid. In certain embodiments, the mutant CFTR is a Arg117His mutant. In certain embodiments, the mutant CFTR is a 120del23 mutant. In certain embodiments, the mutant CFTR is a Phe508del mutant. In certain embodiments a human subject harbors a CFTR mutation in at least one allele of the gene encoding the CFTR protein (e.g., one allele encodes wild-type CFTR and one allele encodes Phe508del CFTR). In certain embodiments, a human subject harbors a CFTR mutation in at least two of the alleles of the gene encoding the CFTR protein. In certain embodiments, a human subject harbors the same mutation in at least two of the alleles of the gene encoding the CFTR protein (e.g., both alleles encode a Phe508del mutant, i.e., homozygous). In certain embodiments, a human subject harbors different mutations in at least two of the alleles of the gene encoding the CFTR protein (e.g., one allele encodes a Phe508del mutant and one allele encodes a Gly551Asp mutant, i.e., heterozygous). In certain embodiments a cell harbors a CFTR mutation in at least one allele of the gene encoding the CFTR protein (e.g., one allele encodes wild-type CFTR and one allele encodes Phe508del CFTR). In certain embodiments, a cell harbors a CFTR mutation in at least two of the alleles of the gene encoding the CFTR protein. In certain embodiments, a cell harbors the same mutation in at least two of the alleles of the gene encoding the CFTR protein (e.g., both alleles encode a Phe508del mutant, i.e., homozygous). In certain embodiments, a cell harbors different mutations in at least two of the alleles of the gene encoding the CFTR protein (e.g., one allele encodes a Phe508del mutant and one allele encodes a Gly551Asp mutant, i.e., heterozygous). In certain embodiments, the cell is an epithelial cell. In certain embodiments, the epithelial cell is a lung epithelial cell. In certain embodiments, the lung epithelial cell is a bronchial epithelial cell. In certain embodiments, the bronchial epithelial cell is derived from a patient with cystic fibrosis.

The Phe508del mutant is the most common mutant among patients with cystic fibrosis. The Phe508del mutant results from a deletion mutation in which the codon for the phenylalanine at amino acid position 508 is deleted, resulting in a CFTR protein that lacks residue 508 (e.g., is 1479 amino acids in length). Phe508del CFTR has the following standard amino acid sequence (GenBank and NCBI Reference Sequence Accession Number:

```
(NM_000492.3(CFTR):c.1521_1523delCTT):
                                          (SEQ ID NO: 2)
MQRSPLEKASVVSKLFFSWTRPILRKGYRQRLELSDIYQIPSVDSADNLS

EKLEREWDRELASKKNPKLINALRRCFFWRFMFYGIFLYLGEVTKAVQPL

LLGRIIASYDPDNKEERSIAIYLGIGLCLLFIVRTLLLHPAIFGLHHIGM

QMRIAMFSLIYKKTLKLSSRVLDKISIGQLVSLLSNNLNKFDEGLALAHF

VWIAPLQVALLMGLIWELLQASAFCGLGFLIVLALFQAGLGRMMMKYRDQ

RAGKISERLVITSEMIENIQSVKAYCWEEAMEKMIENLRQTELKLTRKAA

YVRYFNSSAFFFSGFFVVFLSVLPYALIKGIILRKIFTTISFCIVLRMAV
```

-continued

```
TRQFPWAVQTWYDSLGAINKIQDFLQKQEYKTLEYNLTTTEVVMENVTAF

WEEGFGELFEKAKQNNNNRKTSNGDDSLFFSNFSLLGTPVLKDINFKIER

GQLLAVAGSTGAGKTSLLMVIMGELEPSEGKIKHSGRISFCSQFSWIMPG

TIKENIIGVSYDEYRYRSVIKACQLEEDISKFAEKDNIVLGEGGITLSGG

QRARISLARAVYKDADLYLLDSPFGYLDVLTEKEIFESCVCKLMANKTRI

LVTSKMEHLKKADKILILHEGSSYFYGTFSELQNLQPDFSSKLMGCDSFD

QFSAERRNSILTETLHRFSLEGDAPVSWTETKKQSFKQTGEFGEKRKNSI

LNPINSIRKFSIVQKTPLQMNGIEEDSDEPLERRLSLVPDSEQGEAILPR

ISVISTGPTLQARRRQSVLNLMTHSVNQGQNIHRKTTASTRKVSLAPQAN

LTELDIYSRRLSQETGLEISEEINEEDLKECFFDDMESIPAVTTWNTYLR

YITVHKSLIFVLIWCLVIFLAEVAASLVVLWLLGNTPLQDKGNSTHSRNN

SYAVIITSTSSYYVFYIYVGVADTLLAMGFFRGLPLVHTLITVSKILFIH

KMLHSVLQAPMSTLNTLKAGGILNRFSKDIAILDDLLPLTIFDFIQLLLI

VIGAIAVVAVLQPYIFVATVPVIVAFIMLRAYFLQTSQQLKQLESEGRSP

IFTHLVTSLKGLWTLRAFGRQPYFETLFHKALNLHTANWFLYLSTLRWFQ

MRIEMIFVIFFIAVTFISILTTGEGEGRVGIILTLAMNIMSTLQWAVNSS

IDVDSLMRSVSRVFKFIDMPTEGKPTKSTKPYKNGQLSKVMIIENSHVKK

DDIWPSGGQMTVKDLTAKYTEGGNAILENISFSISPGQRVGLLGRTGSGK

STLLSAFLRLLNTEGEIQIDGVSWDSITLQQWRKAFGVIPQKVFIFSGTF

RKNLDPYEQWSDQEIWKVADEVGLRSVIEQFPGKLDFVLVDGGCVLSHGH

KQLMCLARSVLSKAKILLLDEPSAHLDPVTYQIIRRTLKQAFADCTVILC

EHRIEAMLECQQFLVIEENKVRQYDSIQKLLNERSLFRQAISPSDRVKLF

PHRNSSKCKSKPQIAALKEETEEEVQDTRL
```

In certain embodiments, a CFTR protein is a mutant CFTR protein, e.g., the sequence of the protein comprises the sequence of a naturally occurring mutant form of CFTR. In certain embodiments, the mutant CFTR protein is at least 70%, 80%, 90%, 95%, 96%, 97%, 98%, 99%, 99.5% or more, e.g. 100%, identical in sequence to Phe508del CFTR of SEQ ID NO: 2. In certain embodiments, the mutant CFTR protein is at least 70% identical in sequence to Phe508del CFTR of SEQ ID NO: 2. In certain embodiments, the mutant CFTR protein is at least 80% identical in sequence to Phe508del CFTR of SEQ ID NO: 2. In certain embodiments, the mutant CFTR protein is at least 90% identical in sequence to Phe508del CFTR of SEQ ID NO: 2. In certain embodiments, the mutant CFTR protein is at least 95% identical in sequence to Phe508del CFTR of SEQ ID NO: 2. In certain embodiments, the mutant CFTR protein is at least 96% identical in sequence to Phe508del CFTR of SEQ ID NO: 2. In certain embodiments, the mutant CFTR protein is at least 97% identical in sequence to Phe508del CFTR of SEQ ID NO: 2. In certain embodiments, the mutant CFTR protein is at least 98% identical in sequence to Phe508del CFTR of SEQ ID NO: 2. In certain embodiments, the mutant CFTR protein is at least 99% identical in sequence to Phe508del CFTR of SEQ ID NO: 2. In certain embodiments, the mutant CFTR protein is at least 99.5% identical in sequence to Phe508del CFTR of SEQ ID NO: 2. In certain embodiments, the mutant CFTR protein is at least 100% identical in sequence to Phe508del CFTR of SEQ ID NO: 2.

In certain embodiments, the CFTR protein cannot be properly processed by traditional cellular machinery in the endoplasmic reticulum (ER). In certain embodiments, the CFTR protein cannot fold properly. In certain embodiments, the CFTR protein cannot be properly trafficked to the plasma membrane (e.g., remains in the cytoplasm or in the endoplasmic reticulum). In certain embodiments, the CFTR protein displays impaired ion channel gating functionality, i.e., cannot open properly for chloride ions to be transported out of the cell.

In certain embodiments, the CFTR protein is a variant or fragment of Phe508del CFTR of SEQ ID NO: 2. In certain embodiments, the CFTR variant comprises or consists of a polypeptide that is over at least 50%, 60%, 70%, 80%, 90%, 95%, 96%, 97%, 98%, 99%, 99.5%, or 100% of the Phe508del CFTR of SEQ ID NO: 2. In certain embodiments, the CFTR variant comprises or consists of a polypeptide that is over at least 50% of the Phe508del CFTR of SEQ ID NO: 2. In certain embodiments, the CFTR variant comprises or consists of a polypeptide that is over at least 60% of the Phe508del CFTR of SEQ ID NO: 2. In certain embodiments, the CFTR variant comprises or consists of a polypeptide that is over at least 70% of the Phe508del CFTR of SEQ ID NO: 2. In certain embodiments, the CFTR variant comprises or consists of a polypeptide that is over at least 80% of the Phe508del CFTR of SEQ ID NO: 2. In certain embodiments, the CFTR variant comprises or consists of a polypeptide that is over at least 90% of the Phe508del CFTR of SEQ ID NO: 2. In certain embodiments, the CFTR variant comprises or consists of a polypeptide that is over at least 95% of the Phe508del CFTR of SEQ ID NO: 2. In certain embodiments, the CFTR variant comprises or consists of a polypeptide that is over at least 96% of the Phe508del CFTR of SEQ ID NO: 2. In certain embodiments, the CFTR variant comprises or consists of a polypeptide that is over at least 97% of the Phe508del CFTR of SEQ ID NO: 2. In certain embodiments, the CFTR variant comprises or consists of a polypeptide that is over at least 98% of the Phe508del CFTR of SEQ ID NO: 2. In certain embodiments, the CFTR variant comprises or consists of a polypeptide that is over at least 99% of the Phe508del CFTR of SEQ ID NO: 2. In certain embodiments, the CFTR variant comprises or consists of a polypeptide that is over at least 99.5% of the Phe508del CFTR of SEQ ID NO: 2. In certain embodiments, the CFTR variant comprises or consists of a polypeptide that is over at least 100% of the Phe508del CFTR of SEQ ID NO: 2. These variants may be biologically active variants of Phe508del CFTR, such that the ion channel gating function and/or the chloride transport function of the CFTR is retained in the variant. These variants may be biologically inactive variants of Phe508del CFTR, such that the ion channel gating function and/or the chloride transport function of the CFTR is abrogated (e.g., not functional) in the variant.

In some embodiments a mammalian nucleic acid sequence, e.g., a human nucleic acid sequence, e.g., a human DNA sequence encoding a CFTR protein (e.g., wild-type CFTR, Phe508del CFTR) may be codon optimized for increased expression in a cell. In certain embodiments, a sequence encoding a CFTR protein may be codon optimized for increased expression in an epithelial cell. In certain embodiments, the epithelial cell is a small intestine epithelial cell. In certain embodiments, the epithelial cell is a lung epithelial cell. In certain embodiments, the lung epithelial cell is a bronchial epithelial cell. The bronchial epithelial cell may be derived from a subject with cystic fibrosis.

In some embodiments, a CFTR protein provided in a purified form. In some embodiments, a CFTR protein is provided in the form of a cell lysate. In some embodiments, a CFTR protein is provided in the form of a tissue homogenate.

EXAMPLES

In order that the invention described herein may be more fully understood, the following examples are set forth. The examples described in this application are offered to illustrate the methods, compositions, and systems provided herein and are not to be construed in any way as limiting their scope.

General Experimental

Ussing chamber equipment for cell culture: EM-CSYS-8 Ussing Chamber System, P2300 Chambers, P2302 Sliders, VCC MC8 Multichannel Voltage/current Clamp, P2020 Electrodes, and DM MC6 Single Channel Electrode Input Module and Dummy Membranes (Physiologic Instruments, San Diego, CA).

Electrodes: Silver/silver chloride (Ag/AgCl) electrodes placed in 4% agar-Ringer buffer-containing electrode tips Ringer solution: 115 mM NaCl, 25 mM $NaHCO_{3-}$, 2.4 mM $K_2HPO_4$, 0.4 mM $KH_2PO_4$, 1.2 mM $MgCl_2$, 1.2 mM $CaCl_2$, and 20 mM HEPES. NaOH to adjust pH to 7.4. Osmolarity 290-300 mOsm.

Example 1

Described herein are select amino acids (AA) or their combinations in a formulation that are able to stimulate chloride secretion and reduce ENaC activity by increasing CFTR and decreasing ENaC expression and activity on the apical membrane. The AA formulations were tested in primary human bronchial epithelial cells (HBEC) with the mutation CFTRΔF508. The cells were obtained from CF and non-CF patients. Cells were grown to 80% confluence in culture dishes and the they were transferred to snapwell permeable inserts. Cells were grown to mature and differentiated in permeable cell culture supports for ~30 days in air-media interface. Thereafter the cells were studied in Ussing chamber for measuring the transepithelial current and resistance.

Short-circuit current (Isc) and resistance (R) was measured in fully differentiated primary homozygous CFTRΔF508 HBEC cultured at an air-liquid interface for 28 to 42 days after exposure to the select AA formulation (CF3AA, CF4AA-1/2/4, CF5AA), CF4AA-3 (negative control) and vehicle (control) in Ussing chambers. Changes in Isc were measured following inhibition of ENaC with 6 μM benzamil, activation of cAMP-activated CFTR channel activity using 10 μM forskolin, 1 μM PG01 (potentiator), blocking CFTR channel using 20 μM CFTR(inh)-172 and blocking basal Ca-activated chloride channel (CaCC) activity using 10 μM CaCCinh-A01, respectively. Similar experiments were repeated in CFTRΔF508 HBEC treated for 24 hrs prior to the experiment with 6 μM C18, a corrector for CFTR misfolding. Cellular CFTR and ENaC protein expression were analyzed using western blot, and protein localization was demonstrated using immunofluorescence microscopy.

Figure 1B:
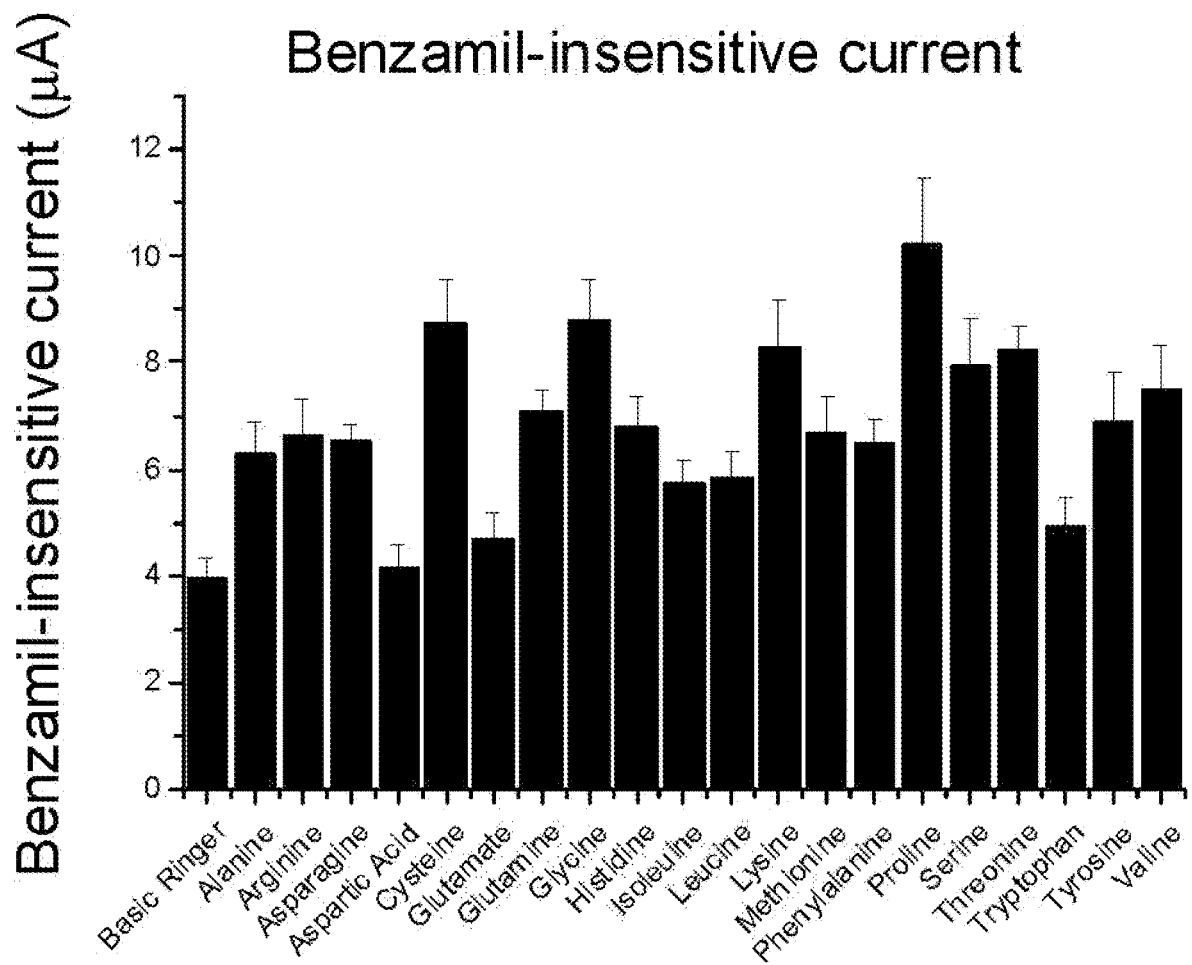
FIG. 1B shows a graph of benzamil-insensitive current (μA) with C18 for a control (Basic Ringers) solution and for various individual AA (n=4).

FIG. 1A shows a graph of benzamil-insensitive current (μA) without C18 for a control (Basic Ringers) solution and for various individual amino acids (AA) (n=4). FIG. 1B shows a graph of benzamil-insensitive current (μA) with C18 for a control (Basic Ringers) solution and for various individual AA (n=4). Benzamil is an ENaC blocker, so Benzamil-insensitive current therefore represents the current remaining after blocking the ENaC. For both FIG. 1A and FIG. 1B, the best amino acids were selected from the single amino acids based on the delta change in the selected current.

Figure 2A:
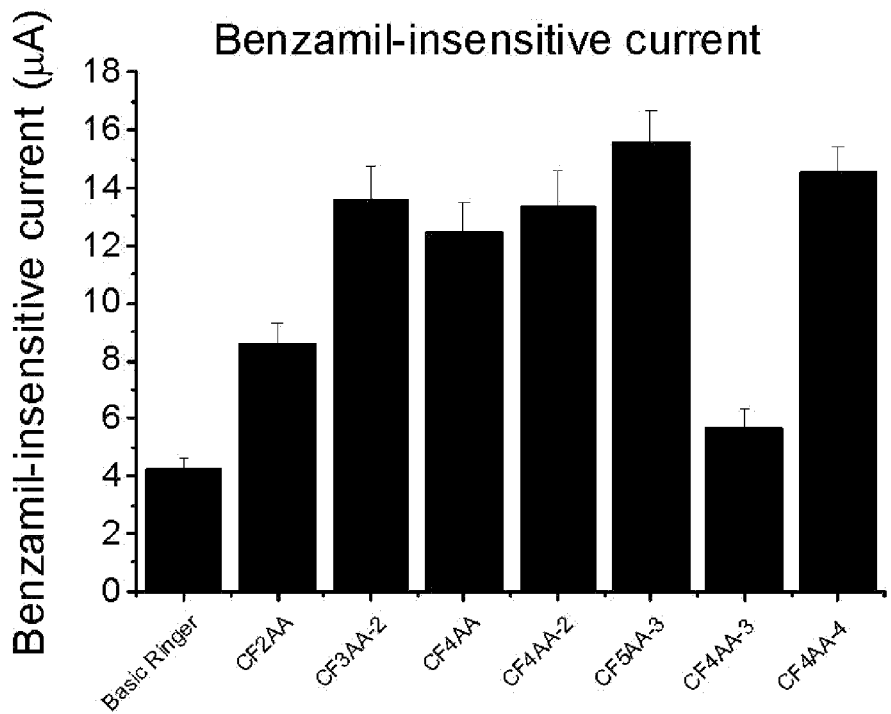
FIG. 2A shows a graph of benzamil-insensitive current (μA) without C18 for a control (Basic Ringers) solution and for various AA combinations (CF2AA, CF3AA-2, CF4AA, CF4AA-2, CF5AA-3, CF4AA-3 and CF4AA-4) (n=4).
Figure 2B:
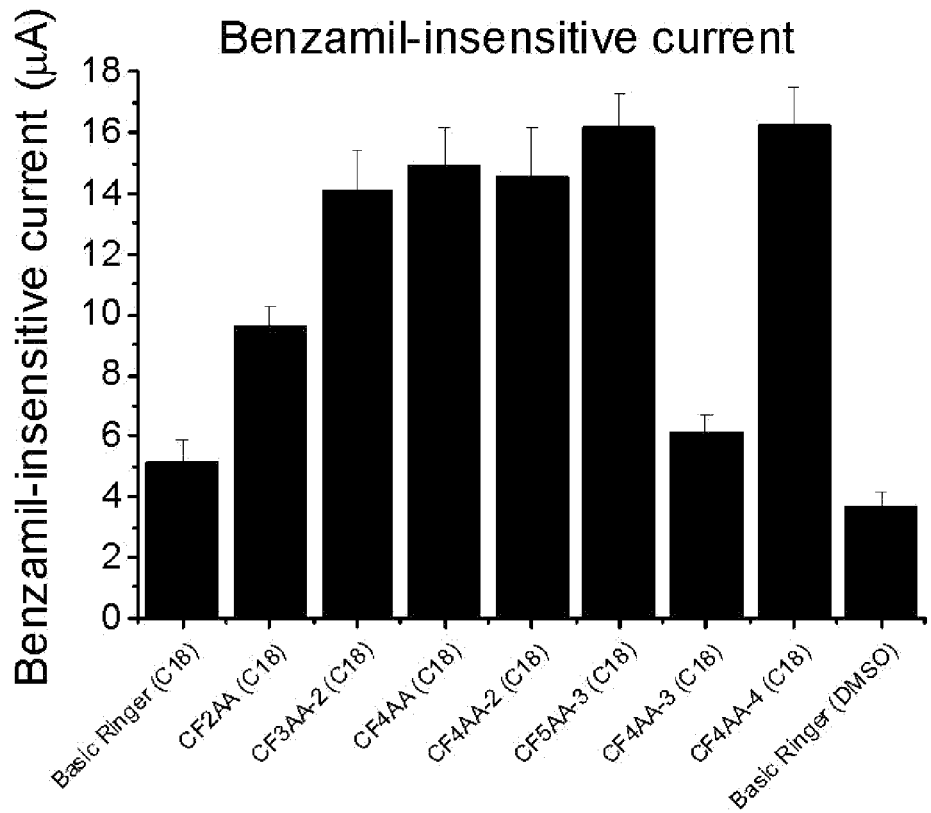
FIG. 2B shows a graph of benzamil-insensitive current (μA) with C18 for a control (Basic Ringers) solution, Basic Ringers with DMSO, and for various AA combinations (CF2AA, CF3AA-2, CF4AA, CF4AA-2, CF5AA-3, CF4AA-3 and CF4AA-4) (n=4).

FIG. 2A shows a graph of benzamil-insensitive current (μA) without C18 for a control (Basic Ringers) solution and for various AA combinations (CF2AA, CF3AA-2, CF4AA, CF4AA-2, CF5AA-3, CF4AA-3 and CF4AA-4) (n=4). CF5AA-3 yielded the highest Benzamil-insensitive current and CF4AA-3 was a negative control. FIG. 2B shows a graph of benzamil-insensitive current (μA) with C18 for a control (Basic Ringers) solution, Basic Ringers with DMSO, and for various AA combinations (CF2AA, CF3AA-2, CF4AA, CF4AA-2, CF5AA-3, CF4AA-3 and CF4AA-4) (n=4). CF5AA-3 still yielded the highest Benzamil-insensitive current and CF4AA-3 was a negative control.

Figure 3A:
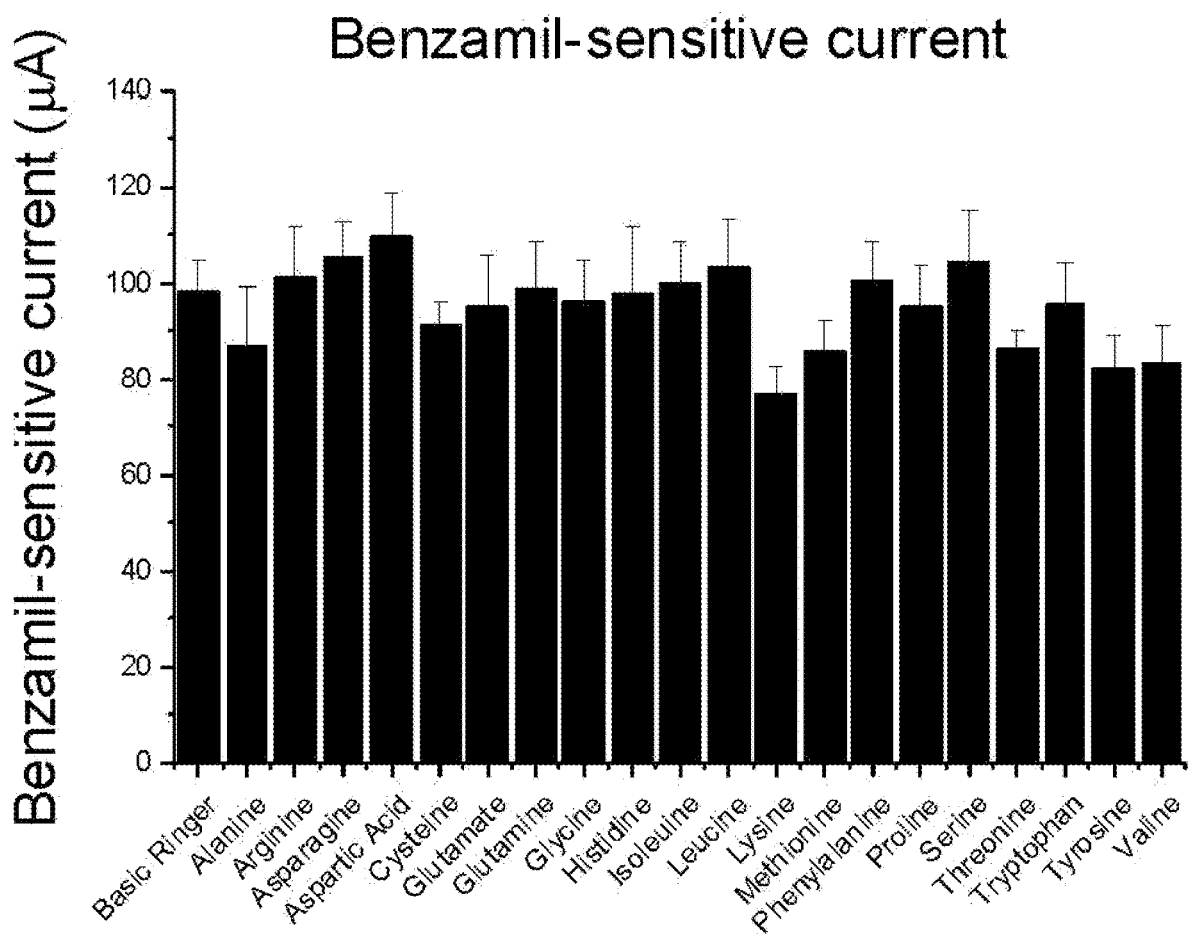
FIG. 3A shows a graph of benzamil-sensitive current (μA) without C18 for a control (Basic Ringers) solution and for various individual amino acids (AA) (n=4).
Figure 3B:
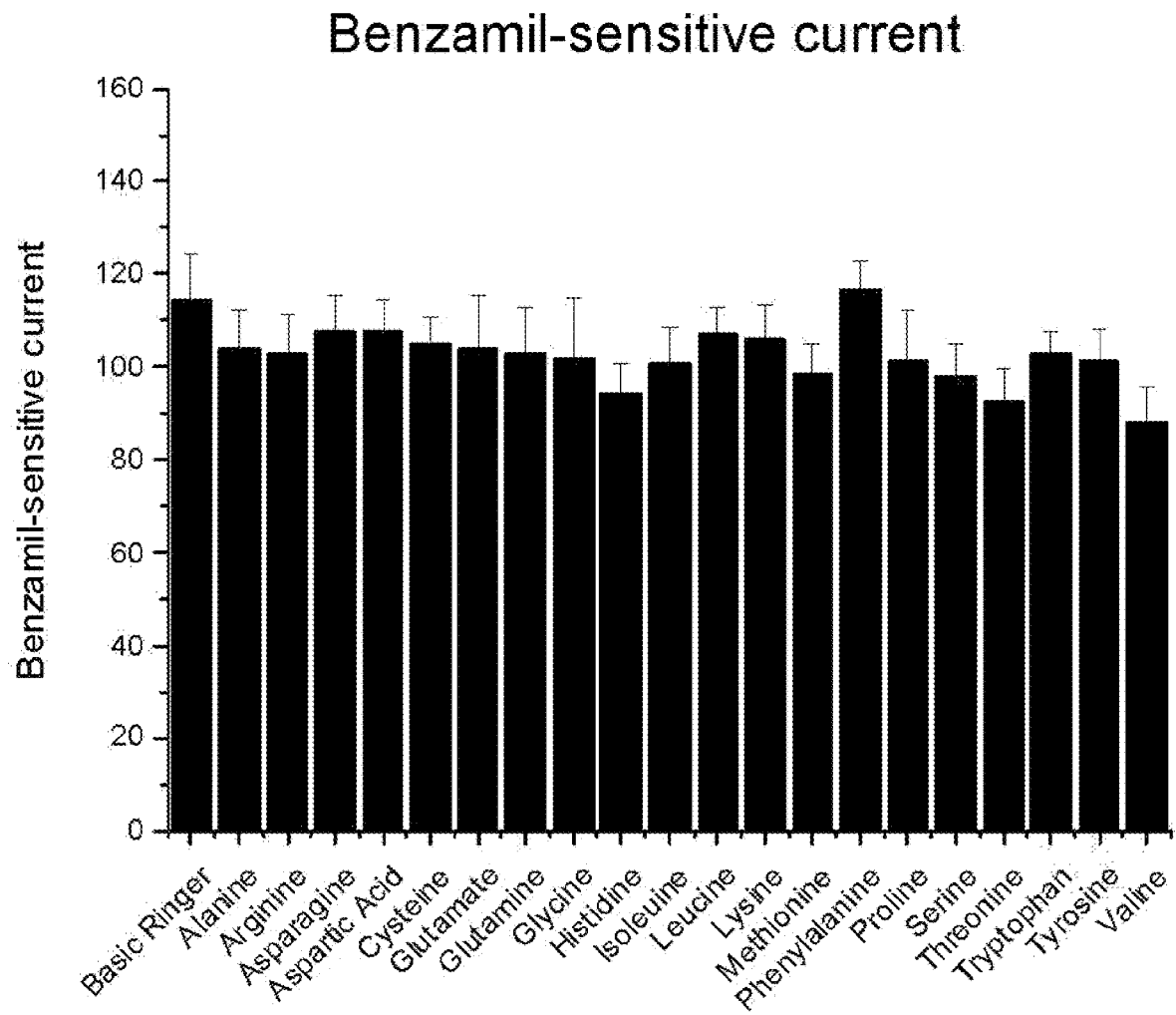
FIG. 3B shows a graph of benzamil-sensitive current (μA) with C18 for a control (Basic Ringers) solution and for various individual amino acids (AA) (n=4).

FIG. 3A shows a graph of benzamil-sensitive current (μA) without C18 for a control (Basic Ringers) solution and for various individual amino acids (AA) (n=4). FIG. 3B shows a graph of benzamil-sensitive current (μA) with C18 for a control (Basic Ringers) solution and for various individual amino acids (AA) (n=4). A higher Benzamil-sensitive current means that more ENaC activity remains. AA solutions that could inhibit ENaC activity show a low Benzamil-sensitive current.

Figure 4A:
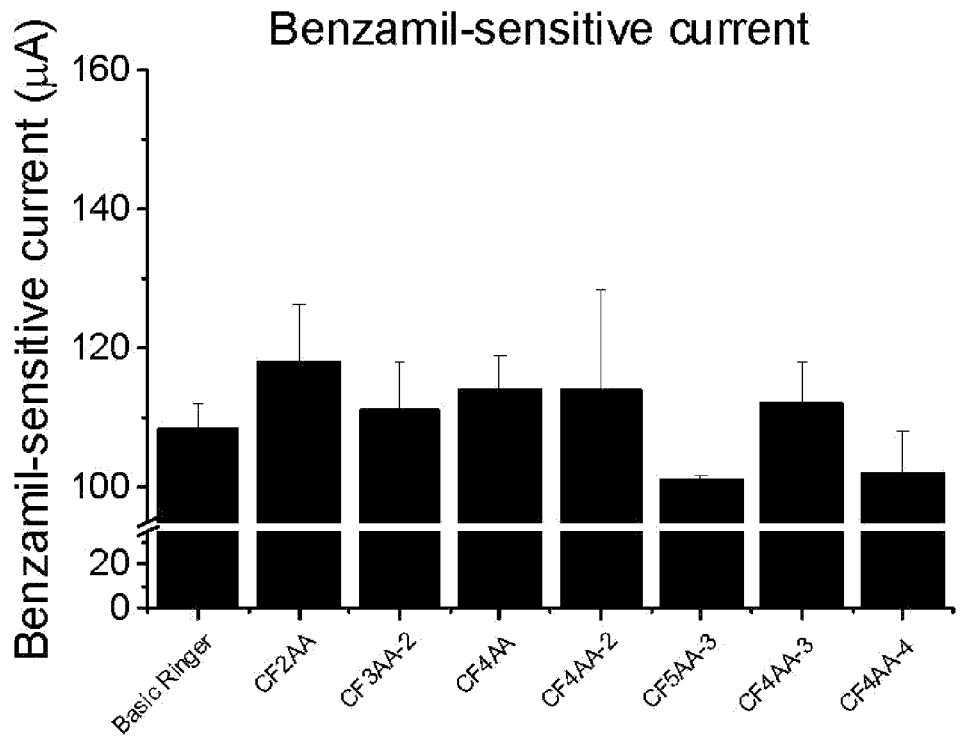
FIG. 4A shows a graph of benzamil-sensitive current (μA) without C18 for a control (Basic Ringers) solution and for various AA combinations (CF2AA, CF3AA-2, CF4AA, CF4AA-2, CF5AA-3, CF4AA-3 and CF4AA-4) (n=4).
Figure 4B:
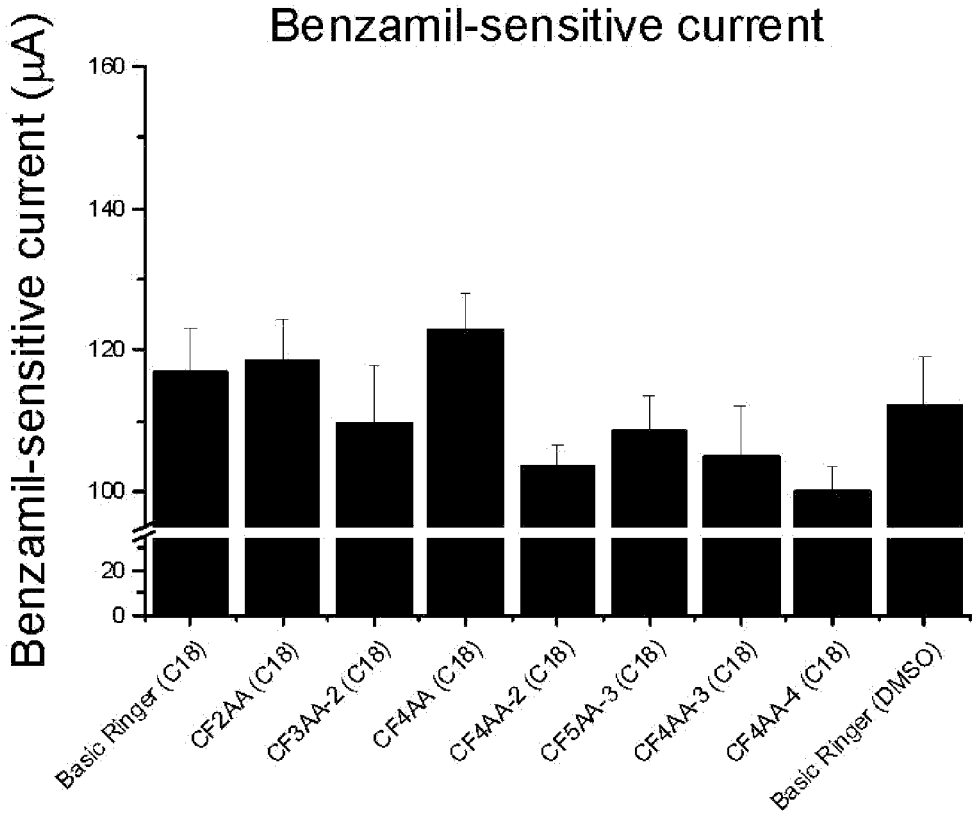
FIG. 4B shows a graph of benzamil-sensitive current (μA) with C18 for a control (Basic Ringers) solution, Basic Ringers with DMSO, and for various AA combinations (CF2AA, CF3AA-2, CF4AA, CF4AA-2, CF5AA-3, CF4AA-3 and CF4AA-4) (n=4).
Figure 5:
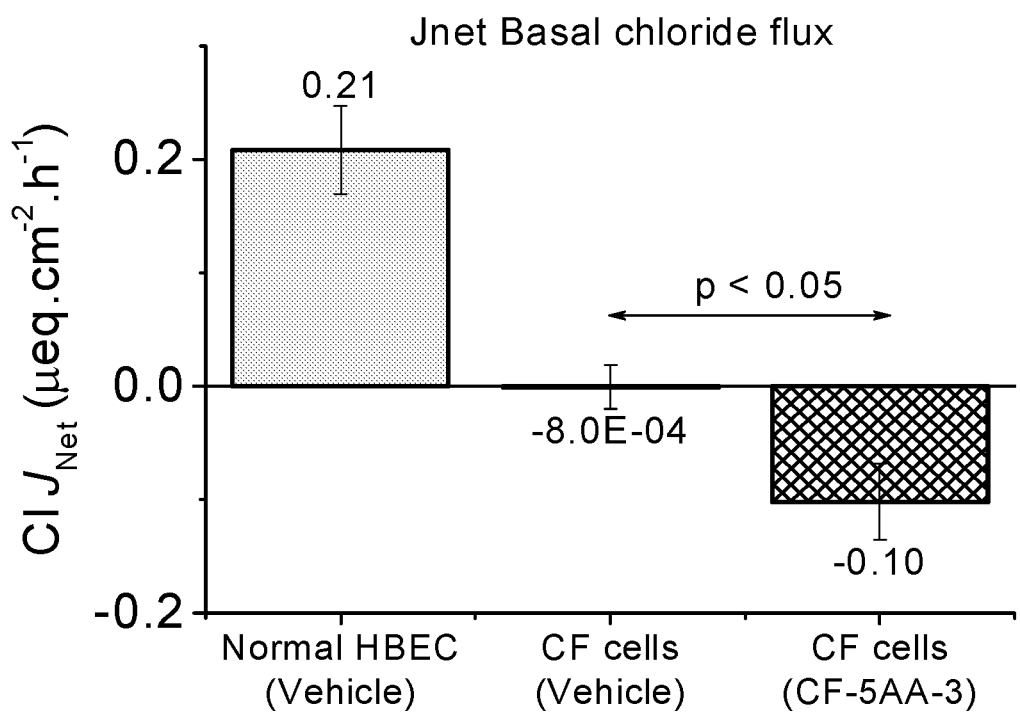
FIG. 5 shows a graph depicting basal chloride flux. Non-stimulated CF cells bathed in vehicle do not secrete chloride. However, chloride secretion was significantly increased in CF cells bathed in CF-5AA-3 (P<0.05; n=7).
Figure 6:
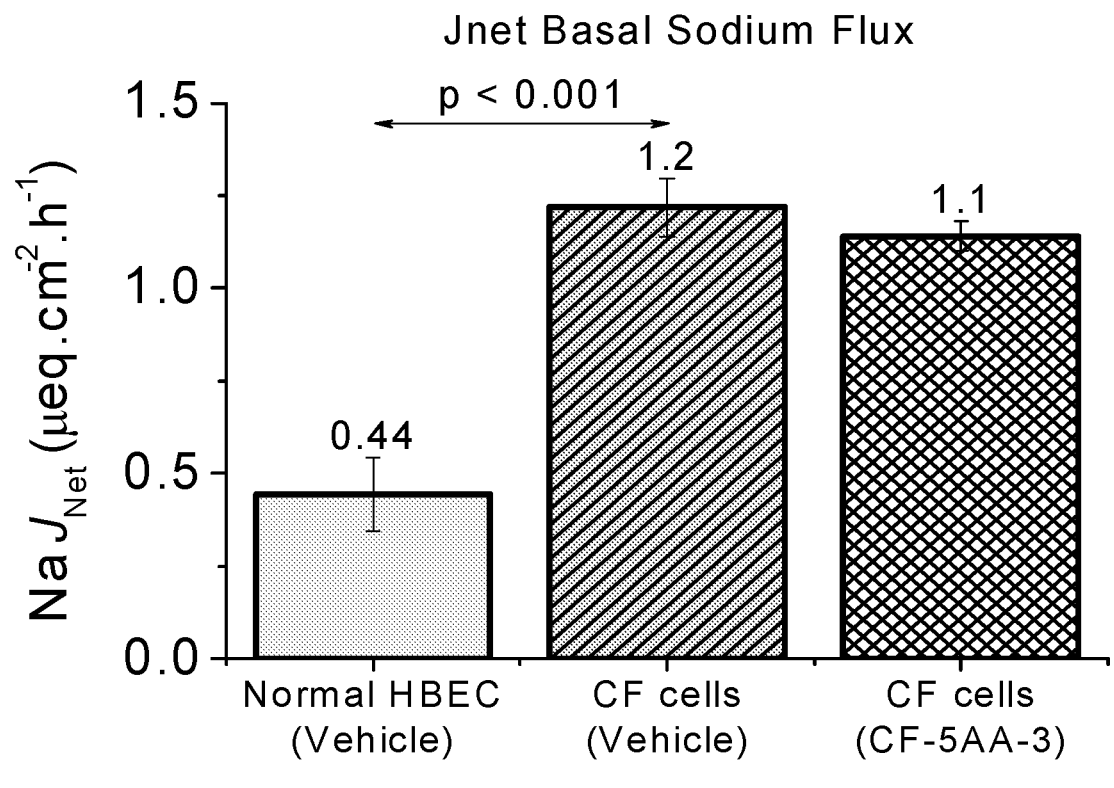
FIG. 6 shows a graph depicting basal chloride flux. Non-stimulated CF cells bathed in vehicle and CF-5AA-3 have a significantly higher sodium absorption compared to non-stimulated normal HBECs (P<0.001; n=6).

FIG. 4A shows a graph of benzamil-sensitive current (μA) without C18 for a control (Basic Ringers) solution and for various AA combinations (CF2AA, CF3AA-2, CF4AA, CF4AA-2, CF5AA-3, CF4AA-3 and CF4AA-4) (n=4). FIG. 4B shows a graph of benzamil-sensitive current (μA) with C18 for a control (Basic Ringers) solution, Basic Ringers with DMSO, and for various AA combinations (CF2AA, CF3AA-2, CF4AA, CF4AA-2, CF5AA-3, CF4AA-3 and CF4AA-4) (n=4). CF5AA-3 yields the greatest decrease in ENaC current.

Overall, the basal resistance of the cells was between 350 and 500 Ohm. CF4AA-4 and CF5AA-3 reduced ENaC activity compared to controls as shown in the FIG. 4A (benzamil-sensitive current). The benzamil-insensitive current representing chloride secretion was higher in cells treated with AA formulations, except for CF4AA-3, and C18 did not result in a significant change in Isc (FIGS. 2A and 2B). Forskolin and PG01 further increased the Isc in cells exposed to AA formulations when compared to controls and CF4AA-3. CFTR was the main contributor to the chloride secretion in HBEC treated with AA formulations, but not CaCC. Pre-treatment with C18 showed a small increase in Isc following forskolin, PG01 and a small inhibition following CFTR(inh)-172 compared to corresponding controls. Expression of CFTR protein increased, and ENaC decreased in HBEC treated with AA formulations, with the majority of CFTR located in the apical membrane of cells.

In conclusion, formulations based on a select set of AAs can improve dysfunctional chloride and sodium channel activity in CFTRΔF508 HBEC by modifying the membrane channel expression and function. These formulations could be used alone or in conjunction with existing standard of care.

Example 2

Materials and Methods

Cell model: Fully differentiated primary normal human bronchial epithelial cells (HBEC), and homozygous CFTRΔF508 HBEC (CF cells) were cultured on snapwells at an air-liquid interface for 28 to 40 days.

Ussing chamber: Transepithelial short-circuit current (Is), resistance (R), and unidirectional ($J_{ms}$ & $J_{sm}$) and net fluxes ($J_{net}$) of $^{22}$Na and $^{36}$Cl were measured in normal HBECs and CF cells while bathing in vehicle, or CF-5AA-3 and CF-4AA-3. Chloride secretion was stimulated with forskolin (FSK, 10 μM apical and basolateral) and the potentiator GLPG1837 (3 μM apical), and benzamil (6 μM apical) and bumetanide (20 uM apical and basolateral) were used to block ENaC and NKCC.

Statistics: Statistical differences between vehicle and AA formulations were calculated using analysis of variance (OriginPlus 2016). P<0.05 was considered statistically significant.

Figure 11:
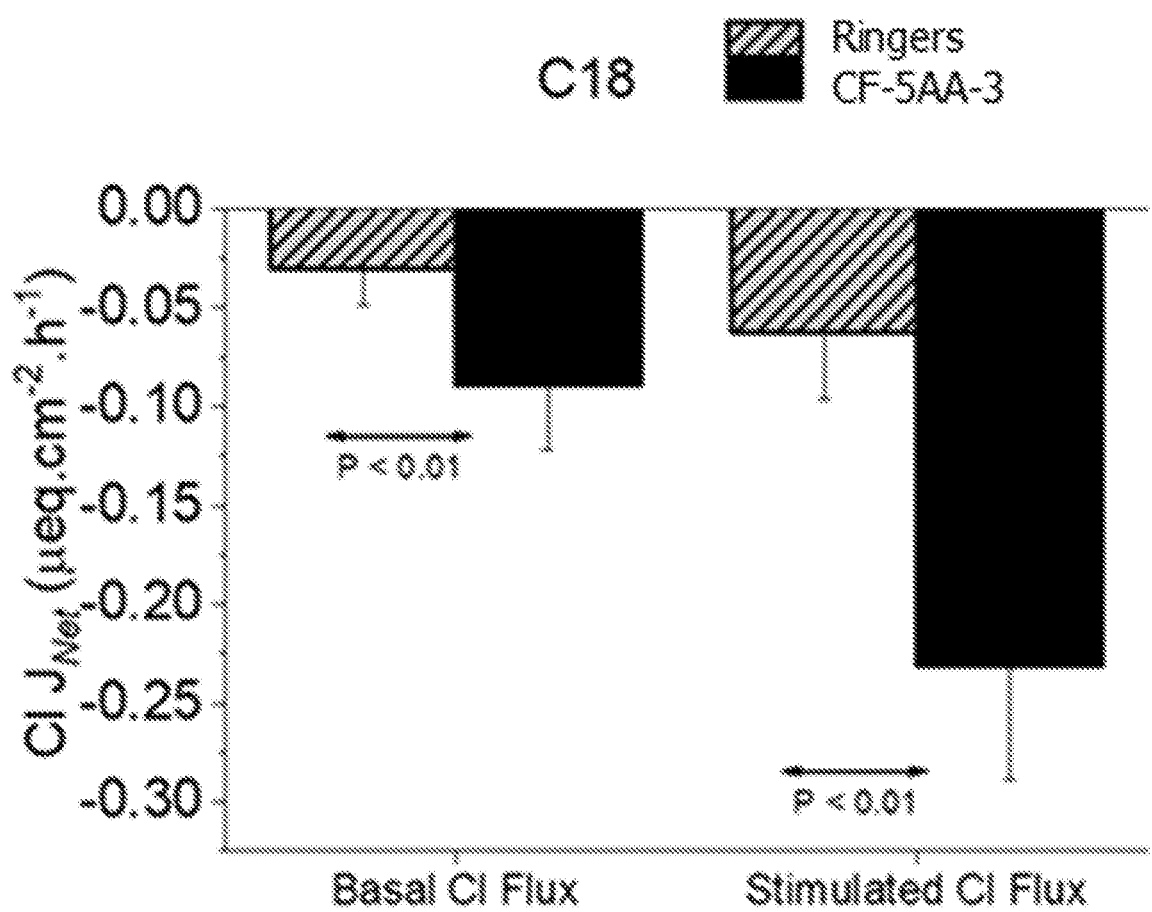
FIG. 11 shows a graph depicting $^{36}$Chloride flux studies in primary HBECs with CFTRΔF508 showed increased chloride secretion responsive to CF-5AA-3.

Additional experimental details relating in particular to FIGS. 10 and 11 are as follows:

Effect of C18 and/or VX661 on primary human bronchial epithelial cells with CFTRΔF508 was investigated by incubating the cells with DMSO, 6 μM C18 and/or 3 μM VX661 in DMSO for 24 hours prior to the experiment. Experiments were repeated in the presence or absence of GLPG (N-(3-Carbamoyl-5,5,7,7-tetramethyl-5,7-dihydro-4H-thieno[2,3-c]pyran-2-yl)-IH-pyrazole-5-carboxamide). Cells were bathed in Basic Ringers or amino acid (AA) solutions and bubbled with 5% $CO_2$ and 95% $O_2$, respectively. Basolateral Basic Ringer or AA solutions contained 5 mM glucose.

Treatments were as follows:
1. 30 min Baseline Current
2. 6 μM Benzamil (1 μL, M)—15 min
3. With or without 10 uM Forskolin (1 μL, M/S)+3 uM GLPG1837 (1 μL, M)—15 min
4. 20 uM CFTR Inh 172 (2 μL, M/S)—15 min
5. 10 uM CaCC Inh AO1 (1 μL, M)—10 min
6. 20 uM Bumetanide (2 μL, S)—15 min Lumacaftor: C18; Symdeko: VX661(tezacaftor)/C18; Ivacaftor: GLPG1837 (reversible potentiator)

Results

FIGS. 5-9 show that select AA combinations can improve dysfunctional chloride and sodium channel activity in CFTRΔF508 HBEC by correcting and/or modifying plasma membrane channel function. These formulations could successfully complement existing standard of care in patients with the CFTRΔF508 mutation.

FIG. 10A and FIG. 10B show that CF5AA-3 is more effective than corrector and more effective than corrector/s plus potentiator. FIG. 10A and FIG. 10B also show that CF5AA-3 plus corrector/s and potentiator act synergistically.

FIG. 11 shows that CF-5AA-3 induces a statistically significant increase in chloride secretion relative to C18 (corrector) alone, either with respect to basal chloride flux or stimulated chloride flux.

Figure 12:
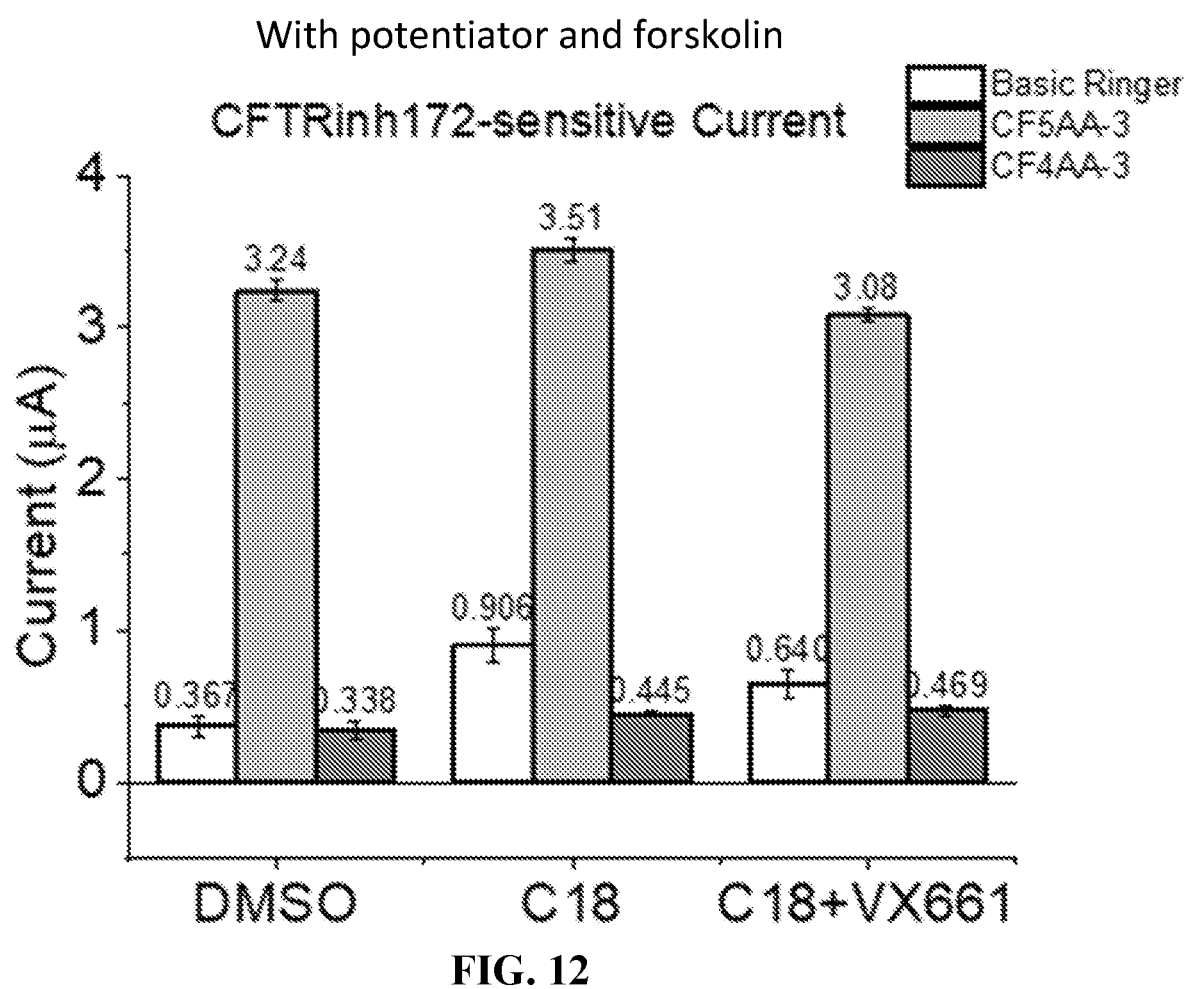
FIG. 12 presents a graph showing that CF5AA-3 increased anion current via CFTR in primary HBECs with CFTRΔF508. Anion current by CF5AA-3 is significantly higher and sustained when compared to triple combination.

FIG. 12 shows a graph showing that CF5AA-3 increased anion current via CFTR Anion current by CF5AA-3 is significantly higher and sustained when compared to triple combination.

FIG. 12 shows that CF5AA-3 stimulates the CFTR channel better than corrector and better than corrector plus potentiator. These results present evidence that CF5AA-3 directly affects the CFTR channel.

Figure 13:
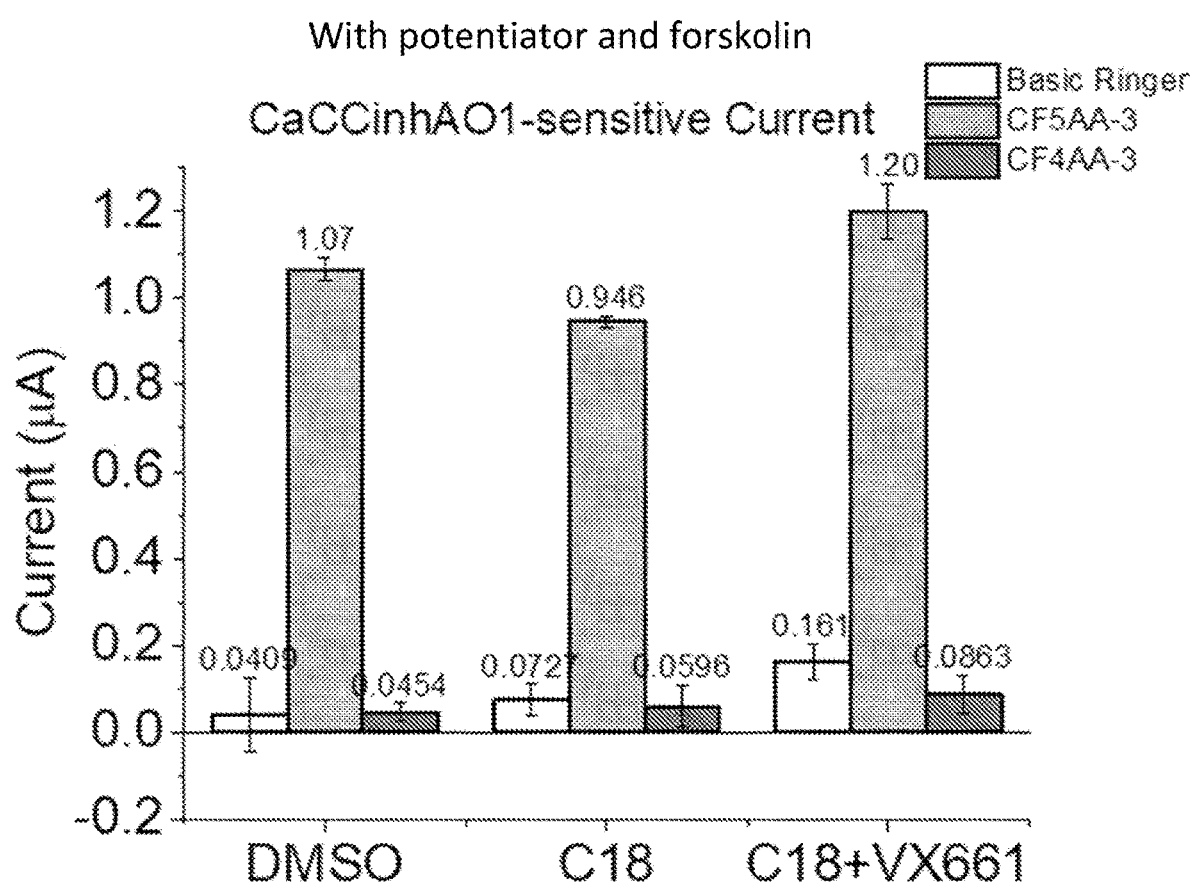
FIG. 13 presents a graph showing that CF5AA-3 increased anion current via Ano1. Ano1-mediated current by CF5AA-3 is significantly higher and sustained when compared to the current observed with triple combination.

FIG. 13 shows that CF5AA-3 stimulates the CaCC channel better than corrector and better than corrector plus potentiator. These results present evidence that CF5AA-3 directly affects the CaCC channel.

Example 3

Background: In patients with Cystic Fibrosis, homozygous F508del mutation causes CFTR protein misfolding, defective trafficking and abnormal gating resulting in decreased chloride secretion which leads to chronic airway inflammation and infection. Combinations of small molecules that correct CFTR misfolding/trafficking (VX809 and VX661), and potentiate CFTR gating (VX770) have been approved for treatments of patients with F508del with suboptimal drug efficacy and adverse effects. The present inventors compared the efficiency or additive efficiency of CF5AA-3 to treatment with VX809/VX770 or VX661/VX770 alone in trafficking defective CFTR and increasing chloride secretion in primary human bronchial epithelial cells with homozygous F508del (HBEC-F508del).

Methods: Transepithelial short-circuit current and $^{36}$Cl net flux ($J_{net}$) were measured in differentiated HBEC-F508del bathed in vehicle (no AA), AA test formulation (CF5AA-3) or AA negative control (NC; CF4AA-3) in Ussing chambers. Cells were treated with C18 (VX809-analogue), VX661 or DMSO for 24 hours. After blocking ENaC with benzamil, chloride secretion was stimulated using GLPG1837 (VX770-analogue) with or without forskolin. CFTRinh-172, CaCCinh-A01 or bumetanide were added to distinguish CFTR-, TMEM16A- and NKCC1-sensitive chloride currents, respectively. Western blot was performed on HBEC-F508del membrane fractions to determine apical CFTR expression.

Figure 14:
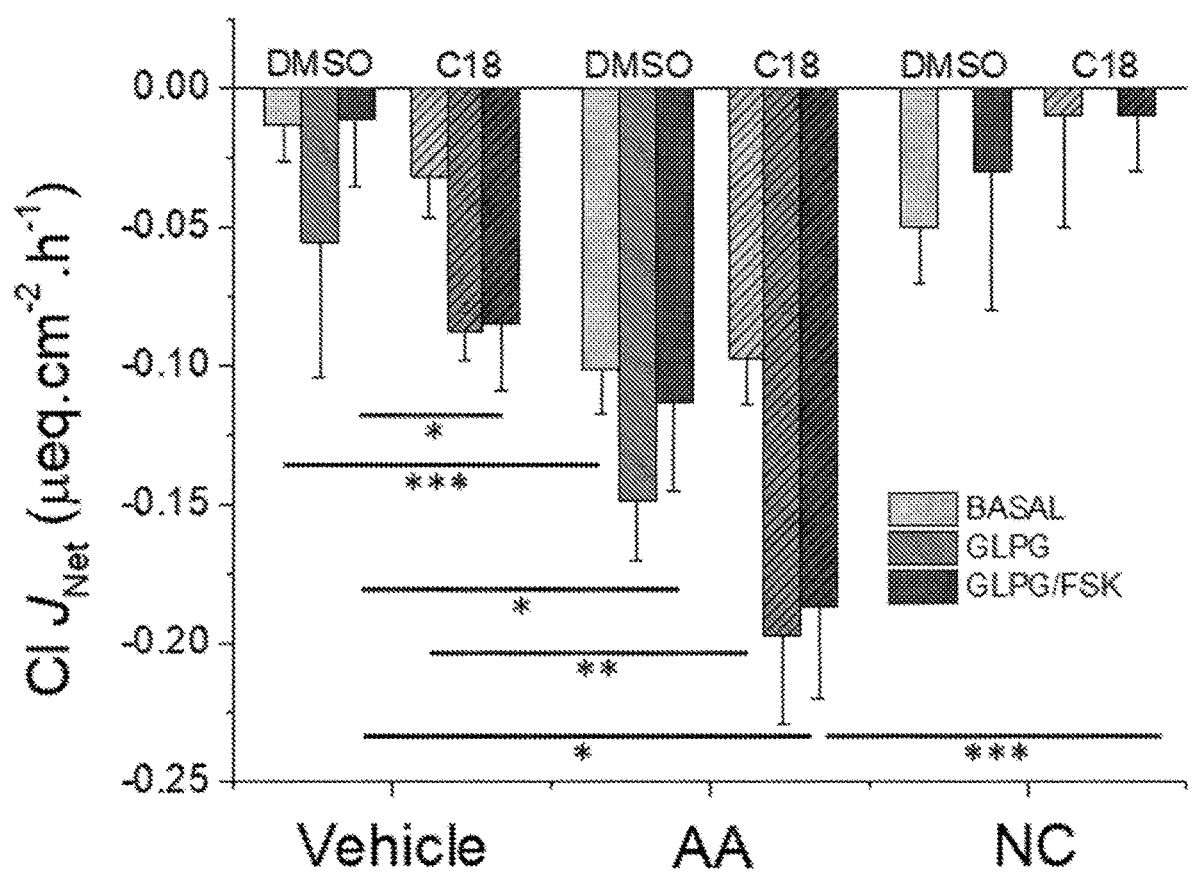
FIG. 14 presents a graph showing that CF5AA-3 increases apical anion secretion to a degree similar to that of the indicated correctors and potentiators.

Results: HBEC-F508del bathed in AA showed significantly higher basal anion currents when compared to vehicle or NC whether cells, pretreated with DMSO (10.7±0.2 μA vs 1.4±0.1 μA vs 2.1±0.1 μA), C18 (11.1±0.2 μA vs 1.6±0.1 μA vs 2.1±0.1 μA) or VX661 (10.8±0.3 μA vs 1.5±0.2 μA vs 2.0±0.2 μA). Stimulation with GLPG1837 caused minor increase in current, with a peak of 12.7±0.4 μA in C18-AA. Anion currents were significantly higher in HBEC-F508del pretreated with C18 and VX661, and stimulated with forskolin and GLPG1837, and peaked at 14.8±0.4 μA in VX661-AA, compared to 7.9±0.7 μA in VX661-vehicle. In the presence of AA, CFTR contributed the most to the stimulated currents (60%), while AA also activated TMEM16A (16%) and other bumetanide-sensitive chloride channels (24%). Flux studies using $^{36}$Cl confirmed increased chloride secretion in HBEC-F508del bathed in AA compared to vehicle or NC regardless of prior treatment (FIG. 14). CFTR membrane expression (c-Band) increased with AA with or without correctors: from 6 (arbitrary units) (DMSO-vehicle) to 9 (C18-vehicle), and from 8 (DMSO-AA) to 12 (C18-AA) respectively. See FIG. 14.

Conclusion: CF5AA-3 increases apical anion secretion similar to correctors and potentiators indicating that CF5AA-3 is a promising pharmaceutically active ingredient as a stand-alone treatment option for CF patients or as an additive in conjunction therapies already implemented for treating CF patients following additional preclinical and clinical studies.

Example 4

Animal Model of CF

A genetically modified rat model will be used in this protocol. This model has alterations to its cystic fibrosis transmembrane conductance regulator (CFTR) gene. The rat model has the human version of the CFTR gene, with a common patient mutation, G551D, inserted, so that it makes a humanized CFTR protein (hCFTR) with the G551D mutation (Class III). The rat model is referred to herein and in the art as the hG551D. Like other animal models of cystic fibrosis, approximately 40% of the hG551D rats exhibit intestinal blockage by 6 weeks of age. Some incidence of intestinal blockage can be prevented with the administration of Go-LYTELY via water, as well as DietGel added to the food for hydration. Additionally, CF knock out (KO) rats develop teeth abnormalities, including malocclusion, which may make it more difficult to chew. Therefore, the rats will receive softened rat food, three times weekly. The affected rats will also be monitored for the need to trim their teeth, to facilitate eating and prevent morbidity or mortality.

The hG551D rat strain was designed to mimic the human disease cystic fibrosis. This disease is characterized by lack of chloride secretion through epithelial cell layers, for example, the nasal epithelial layer. We have shown that the rat airway of hG551D rats exhibits characteristics of cystic fibrosis lung disease. In particular, the rat expresses submucosal glands in the airways, which are similar to those of human patients, and thus, offers a pathology consistent with that seen in human cystic fibrosis patients.

In order to test chloride secretion in hG551D rats and the response to drugs, the nasal potential difference procedure (NPD) will be performed. For the NPD procedure, the rat tail is gently abraded, placed in Lactated Ringer's solution, and connected through a calomel cell to a high impedance voltage follower (VF 1; World Precision Instruments). An exploring probe is established by connecting a Ag/AgCl electrode (wire) bridge into a syringe which pumps solutions at a rate of 180 µl/hr. After approximately five minutes, rats are appropriately somnolent to permit cannulation of the nostril with a PE 10 cannula pulled to a tip diameter of ~0.15 mm. The solutions perfused include Ringer's lactate plus amiloride, a low [Cl] solution containing $K_2HPO_4$, $KH_2PO_4$, Na Gluconate, $NaHCO_3$, Ca Gluconate, and forskolin. Each perfused solution will be administered at approximately a rate of 2 mL/min, with less than 80 uL total per rat into the nasal cavity. Each superperfused condition is studied for 6-10 minutes. Rats will be allowed to recover from anesthesia, and will have atipamazole administered for reversal.

Animals in this study will, for example, be treated with one of four compounds: a test formulation (CF5AA-3), a positive control (ivacaftor), a negative control (CF4AA-3), or the vehicle. Ivacaftor will be given by oral gavage; the other compounds will be given by aerosol nebulization. Animals will be treated once daily for seven days, and then will undergo a nasal potential difference procedure to test for drug efficacy. Nasal potential difference 24 hours after final dose of ivacaftor or VS-009 will be compared. Once this is complete, the animals will be euthanized for tissue collection and subsequent analysis.

Table C presents exemplary dosing for the indicated agents.

| Procedure or Purpose | Agent | Dosage | Route | Frequency |
| --- | --- | --- | --- | --- |
| CFTR modulation | ivacaftor | 40 mg/kg/day | oral gavage | daily, for seven days |
| CFTR modulation | CF5AA-3 | 3 mM | nebulization | daily, for seven days |
| CFTR modulation | CF4AA-3 | 3 mM | nebulization | daily, for seven days |
| CFTR modulation | vehicle | NA | nebulization | daily, for seven days |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims. Where the claims or description relate to a product (e.g., a composition of matter), it should be understood that methods of making or using the product according to any of the methods disclosed herein, and methods of using the product for any one or more of the purposes disclosed herein, are encompassed by the present disclosure, where applicable, unless otherwise indicated or unless it would be evident to one of ordinary skill in the art that a contradiction or inconsistency would arise. Where the claims or description relate to a method, it should be understood that product(s), e.g., compositions of matter, device(s), or system(s), useful for performing one or more steps of the method are encompassed by the present disclosure, where applicable, unless otherwise indicated or unless it would be evident to one of ordinary skill in the art that a contradiction or inconsistency would arise.

Where ranges are given herein, embodiments are provided in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, embodiments that relate analogously to any intervening value or range defined by any two values in the series are provided, and that the lowest value may be taken as a minimum and the greatest value may be taken as a maximum. Where a phrase such as "at least", "up to", "no more than", or similar phrases, precedes a series of numbers herein, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated where applicable. A reasonable lower or upper limit may be selected or determined by one of ordinary skill in the art based, e.g., on factors such as convenience, cost, time, effort, availability (e.g., of samples, agents, or reagents), statistical considerations, etc. In some embodiments an upper or lower limit differs by a factor of 2, 3, 5, or 10, from a particular value. Numerical values, as used herein, include values expressed as percentages. For each embodiment in which a numerical value is prefaced by "about" or "approximately", embodiments in which the exact value is recited are provided. For each embodiment in which a numerical value is not prefaced by "about" or "approximately", embodiments in which the value is prefaced by "about" or "approximately" are provided. "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. In some embodiments a method may be performed by an individual or entity. In some embodiments steps of a method may be performed by two or more individuals or entities such that a method is collectively performed. In some embodiments a method may be performed at least in part by requesting or authorizing another individual or entity to perform one, more than one, or all steps of a method. In some embodiments a method comprises requesting two or more entities or individuals to each perform at least one step of a method. In some embodiments performance of two or more steps is coordinated so that a method is collectively performed. Individuals or entities performing different step(s) may or may not interact.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided. It will be understood that any description or exemplification of a term anywhere herein may be applied wherever such term appears herein (e.g., in any aspect or embodiment in which such term is relevant) unless indicated or clearly evident otherwise.

REFERENCES

1. O'Sullivan B P and Freedman S D (2009) Cystic Fibrosis. *Lancet,* 373; pp. 1891-1904.
2. Brodlie M, Haq I J, Roberts K, Elborn J S (2015) Targeted therapies to improve CFTR function in cystic fibrosis. *Genome Medicine,* 7; doi: 10.1186/s13073-015-0223-6.
3. Corvol H, Thompson K E, Tabary O, et al. (2015) Translating the genetics of cystic fibrosis to personalized medicine. *Transl Res*; doi: 10.1016/j.trsl.2015.04.008.
4. McPhail G L and Clancy J P (2013) Ivacaftor: the first therapy acting on the primary cause of cystic fibrosis. Drugs Today, 49; pp. 253-260.
5. Ramsey B W, Davies J, McElvaney N G, et al. (2011) A CFTR potentiator in patients with cystic fibrosis and the G551D mutation. *N Engl J Med,* 365; pp. 1633-1672.

The invention claimed is:

1. A pharmaceutical formulation comprising free amino acids:
   the free amino acids consisting essentially of a therapeutically effective amount of each of cysteine and proline as free amino acids and
   a therapeutically effective amount of at least one additional free amino consisting of free amino acids of glycine, tyrosine, valine, or lysine, or any combination thereof,
   with the proviso that at least one of the free amino acids is an L-amino acid; and
   optionally,
   at least one pharmaceutically acceptable carrier, buffer, electrolyte, adjuvant, excipient, or water, or any combination thereof.

2. The pharmaceutical formulation of claim 1, wherein the free amino acids are L-amino acids.

3. The pharmaceutical formulation of claim 1, wherein the free amino acids consist of cysteine, proline and the at least one additional amino acid consisting of free amino acids of glycine, tyrosine, valine, or lysine, or any combination thereof.

4. The pharmaceutical formulation of claim 1, wherein the free amino acids consist essentially of or consist of cysteine, proline and glycine as free amino acids and
   optionally one or more additional free amino acids consisting of tyrosine or lysine, or a combination thereof,
   with the proviso that at least one of the free amino acids is an L-amino acid.

5. The pharmaceutical formulation of claim 1, wherein the free amino acids consist essentially of or consist of cysteine, proline, glycine and lysine as free amino acids and
   optionally, an additional free amino acid consisting of tyrosine as a free amino acid,
   with the proviso that at least one of the free amino acids is an L-amino acid.

6. The pharmaceutical formulation of claim 5, wherein the free amino acids consist essentially of or consist of cysteine, proline, glycine and lysine as free amino acids,
   with the proviso that at least one of the free amino acids is an L-amino acid.

7. The pharmaceutical formulation of claim 1, wherein the free amino acids consist essentially of or consist of cysteine, proline, glycine, tyrosine and lysine as free amino acids with the proviso that at least one of the free amino acids is an L-amino acid.

8. The formulation of claim 7, wherein the free amino acids consist of free amino acids of cysteine, proline, glycine, tyrosine and lysine.

9. A pharmaceutical formulation comprising free amino acids:
   the free amino acids consisting essentially of a therapeutically effective amount of each of cysteine, proline, and valine as free amino acids and
   optionally, a therapeutically effective amount of an additional free amino acid consisting of free amino acids of glycine or tyrosine,
   with the proviso that at least one of the free amino acids is an L-amino acid; and
   optionally, at least one pharmaceutically acceptable carrier, buffer, electrolyte, adjuvant, excipient, or water, or any combination thereof.

10. A method for treating a subject afflicted with cystic fibrosis, asthma, or COPD, the method comprising
    administering to the subject afflicted with cystic fibrosis, asthma, or COPD the formulation of claim 1,
    wherein the administering reduces at least one symptom of cystic fibrosis, asthma, or COPD.

11. The method of claim 10, wherein the subject has a mutation in the CFTR gene.

12. The method of claim 11, wherein the mutation in the CFTR comprises Gly542X, Gly551Asp, Arg553X, Arg117His, 120del23, Phe508del, or a combination thereof, wherein X is any amino acid.

13. The method of claim 10, further comprising administering an additional therapeutic agent.

14. The method of claim 13, wherein the additional therapeutic agent is at least one of a CFTR potentiator, CFTR corrector, CFTR read-through agent, or a combination thereof.

15. The method of claim 14, wherein the CFTR potentiator is ivacaftor.

16. A method for increasing the number of cystic fibrosis transmembrane conductance regulator (CFTR) proteins present on the plasma membrane of at least one cell, the method comprising:
    contacting the at least one cell with an effective amount of the pharmaceutical formulation of claim 1,
    wherein the contacting promotes at least one of folding of CFTR or transport of CFTR to the plasma membrane, thereby increasing the number of CFTR proteins present on the plasma membrane of the cell.

17. The method of any one of claim 16, wherein one or more of the CFTR proteins comprise Gly542X, Gly551Asp, Arg553X, Arg117His, 120del23, Phe508del, or a combination thereof, wherein X is any amino acid.

18. The method of claim 16, wherein increasing the number of CFTR proteins present on the plasma membrane of the cell is detected by increased chloride ion export from the cell.

19. The method of claim 16, wherein the cell is a bronchial epithelial cell isolated from a subject afflicted with cystic fibrosis.

20. A method for treating a subject afflicted with cystic fibrosis, asthma, or COPD, the method comprising
administering to the subject afflicted with cystic fibrosis, asthma, or COPD the formulation of claim 9,
wherein the administering reduces at least one symptom of cystic fibrosis, asthma, or COPD.

21. A method for selecting a pharmaceutical formulation optimized to promote activity of a mutant CFTR protein, the method comprising:
contacting at least one cell expressing the mutant CFTR protein with each of the pharmaceutical formulations of claim 1, wherein each of the at least one cells expressing the mutant CFTR protein is contacted with a single one of the pharmaceutical formulations of claim 1;
measuring chloride ion export from each of the at least one cells expressing the mutant CFTR protein contacted with the single one of the pharmaceutical formulations, wherein the chloride ion export is indicative of activity of the mutant CFTR protein;
comparing the chloride ion export from each of the at least one cells contacted with the single one of the pharmaceutical formulations to evaluate and rank relatively each of the pharmaceutical formulations for its ability to promote chloride ion export from the at least one cell expressing the mutant CFTR protein;
wherein each of the at least one cells expressing the mutant CFTR protein contacted with the single one of the pharmaceutical formulations comprise an equal number of cells; and
wherein the single one of the pharmaceutical formulations ranked as promoting the highest level of chloride ion export from the at least one cell expressing the mutant CFTR protein is selected as the pharmaceutical formulation optimized to promote activity of the mutant CFTR protein.

22. The method of claim 21, wherein the at least one cell is a bronchial epithelial cell isolated from a subject afflicted with cystic fibrosis.

23. A method for selecting a pharmaceutical formulation optimized to promote activity of a mutant CFTR protein, the method comprising:
contacting at least one cell expressing the mutant CFTR protein with each of the pharmaceutical formulations of claim 9, wherein each of the at least one cells expressing the mutant CFTR protein is contacted with a single one of the pharmaceutical formulations of claim 9;
measuring chloride ion export from each of the at least one cells expressing the mutant CFTR protein contacted with the single one of the pharmaceutical formulations, wherein the chloride ion export is indicative of activity of the mutant CFTR protein;
comparing the chloride ion export from each of the at least one cells contacted with the single one of the pharmaceutical formulations to evaluate and rank relatively each of the pharmaceutical formulations for its ability to promote chloride ion export from the at least one cell expressing the mutant CFTR protein;
wherein each of the at least one cells expressing the mutant CFTR protein contacted with the single one of the pharmaceutical formulations comprise an equal number of cells; and
wherein the single one of the pharmaceutical formulations ranked as promoting the highest level of chloride ion export from the at least one cell expressing the mutant CFTR protein is selected as the pharmaceutical formulation optimized to promote activity of the mutant CFTR protein.

24. The method of claim 23, wherein the at least one cell is a bronchial epithelial cell isolated from a subject afflicted with cystic fibrosis.

* * * * *

SEQUENCE LISTING

```
<160> NUMBER OF SEQ ID NOS: 2

<210> SEQ ID NO 1
<211> LENGTH: 1480
<212> TYPE: PRT
<213> ORGANISM: Homo sapiens

<400> SEQUENCE: 1

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
```

```
             20                  25                  30
Glu Leu Ser Asp Ile Tyr Gln Ile Pro Ser Val Asp Ser Ala Asp Asn
         35                  40                  45

Leu Ser Glu Lys Leu Glu Arg Glu Trp Asp Arg Glu Leu Ala Ser Lys
 50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
                115                 120                 125

Leu Leu Phe Ile Val Arg Thr Leu Leu Leu His Pro Ala Ile Phe Gly
         130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
                195                 200                 205

Ala Leu Leu Met Gly Leu Ile Trp Glu Leu Leu Gln Ala Ser Ala Phe
         210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
                260                 265                 270

Lys Ala Tyr Cys Trp Glu Glu Ala Met Glu Lys Met Ile Glu Asn Leu
                275                 280                 285

Arg Gln Thr Glu Leu Lys Leu Thr Arg Lys Ala Ala Tyr Val Arg Tyr
         290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
         355                 360                 365

Asn Lys Ile Gln Asp Phe Leu Gln Lys Gln Glu Tyr Lys Thr Leu Glu
370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
                420                 425                 430

Phe Ser Leu Leu Gly Thr Pro Val Leu Lys Asp Ile Asn Phe Lys Ile
         435                 440                 445
```

```
Glu Arg Gly Gln Leu Leu Ala Val Ala Gly Ser Thr Gly Ala Gly Lys
    450                 455                 460
Thr Ser Leu Leu Met Val Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
            500                 505                 510
Asp Glu Tyr Arg Tyr Arg Ser Val Ile Lys Ala Cys Gln Leu Glu Glu
        515                 520                 525
Asp Ile Ser Lys Phe Ala Glu Lys Asp Asn Ile Val Leu Gly Glu Gly
    530                 535                 540
Gly Ile Thr Leu Ser Gly Gly Gln Arg Ala Arg Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
        595                 600                 605
His Leu Lys Lys Ala Asp Lys Ile Leu Ile Leu His Glu Gly Ser Ser
    610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
            660                 665                 670
Gly Asp Ala Pro Val Ser Trp Thr Glu Thr Lys Lys Gln Ser Phe Lys
        675                 680                 685
Gln Thr Gly Glu Phe Gly Glu Lys Arg Lys Asn Ser Ile Leu Asn Pro
    690                 695                 700
Ile Asn Ser Ile Arg Lys Phe Ser Ile Val Gln Lys Thr Pro Leu Gln
705                 710                 715                 720
Met Asn Gly Ile Glu Glu Asp Ser Asp Glu Pro Leu Glu Arg Arg Leu
                725                 730                 735
Ser Leu Val Pro Asp Ser Glu Gln Gly Glu Ala Ile Leu Pro Arg Ile
            740                 745                 750
Ser Val Ile Ser Thr Gly Pro Thr Leu Gln Ala Arg Arg Arg Gln Ser
        755                 760                 765
Val Leu Asn Leu Met Thr His Ser Val Asn Gln Gly Gln Asn Ile His
    770                 775                 780
Arg Lys Thr Thr Ala Ser Thr Arg Lys Val Ser Leu Ala Pro Gln Ala
785                 790                 795                 800
Asn Leu Thr Glu Leu Asp Ile Tyr Ser Arg Arg Leu Ser Gln Glu Thr
                805                 810                 815
Gly Leu Glu Ile Ser Glu Glu Ile Asn Glu Glu Asp Leu Lys Glu Cys
            820                 825                 830
Phe Phe Asp Asp Met Glu Ser Ile Pro Ala Val Thr Thr Trp Asn Thr
        835                 840                 845
Tyr Leu Arg Tyr Ile Thr Val His Lys Ser Leu Ile Phe Val Leu Ile
    850                 855                 860
```

```
Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
            885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
            965                 970                 975

Ser Lys Asp Ile Ala Ile Leu Asp Asp Leu Pro Leu Thr Ile Phe
            980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile
    1010                1015                1020

Val Ala Phe Ile Met Leu Arg Ala Tyr Phe Leu Gln Thr Ser Gln
    1025                1030                1035

Gln Leu Lys Gln Leu Glu Ser Glu Gly Arg Ser Pro Ile Phe Thr
    1040                1045                1050

His Leu Val Thr Ser Leu Lys Gly Leu Trp Thr Leu Arg Ala Phe
    1055                1060                1065

Gly Arg Gln Pro Tyr Phe Glu Thr Leu Phe His Lys Ala Leu Asn
    1070                1075                1080

Leu His Thr Ala Asn Trp Phe Leu Tyr Leu Ser Thr Leu Arg Trp
    1085                1090                1095

Phe Gln Met Arg Ile Glu Met Ile Phe Val Ile Phe Phe Ile Ala
    1100                1105                1110

Val Thr Phe Ile Ser Ile Leu Thr Thr Gly Glu Gly Glu Gly Arg
    1115                1120                1125

Val Gly Ile Ile Leu Thr Leu Ala Met Asn Ile Met Ser Thr Leu
    1130                1135                1140

Gln Trp Ala Val Asn Ser Ser Ile Asp Val Asp Ser Leu Met Arg
    1145                1150                1155

Ser Val Ser Arg Val Phe Lys Phe Ile Asp Met Pro Thr Glu Gly
    1160                1165                1170

Lys Pro Thr Lys Ser Thr Lys Pro Tyr Lys Asn Gly Gln Leu Ser
    1175                1180                1185

Lys Val Met Ile Ile Glu Asn Ser His Val Lys Lys Asp Asp Ile
    1190                1195                1200

Trp Pro Ser Gly Gly Gln Met Thr Val Lys Asp Leu Thr Ala Lys
    1205                1210                1215

Tyr Thr Glu Gly Gly Asn Ala Ile Leu Glu Asn Ile Ser Phe Ser
    1220                1225                1230

Ile Ser Pro Gly Gln Arg Val Gly Leu Leu Gly Arg Thr Gly Ser
    1235                1240                1245

Gly Lys Ser Thr Leu Leu Ser Ala Phe Leu Arg Leu Leu Asn Thr
    1250                1255                1260

Glu Gly Glu Ile Gln Ile Asp Gly Val Ser Trp Asp Ser Ile Thr
```

```
            1265                1270                1275

Leu Gln Gln Trp Arg Lys Ala Phe Gly Val Ile Pro Gln Lys Val
        1280                1285                1290

Phe Ile Phe Ser Gly Thr Phe Arg Lys Asn Leu Asp Pro Tyr Glu
        1295                1300                1305

Gln Trp Ser Asp Gln Glu Ile Trp Lys Val Ala Asp Glu Val Gly
        1310                1315                1320

Leu Arg Ser Val Ile Glu Gln Phe Pro Gly Lys Leu Asp Phe Val
        1325                1330                1335

Leu Val Asp Gly Gly Cys Val Leu Ser His Gly His Lys Gln Leu
        1340                1345                1350

Met Cys Leu Ala Arg Ser Val Leu Ser Lys Ala Lys Ile Leu Leu
        1355                1360                1365

Leu Asp Glu Pro Ser Ala His Leu Asp Pro Val Thr Tyr Gln Ile
        1370                1375                1380

Ile Arg Arg Thr Leu Lys Gln Ala Phe Ala Asp Cys Thr Val Ile
        1385                1390                1395

Leu Cys Glu His Arg Ile Glu Ala Met Leu Glu Cys Gln Gln Phe
        1400                1405                1410

Leu Val Ile Glu Glu Asn Lys Val Arg Gln Tyr Asp Ser Ile Gln
        1415                1420                1425

Lys Leu Leu Asn Glu Arg Ser Leu Phe Arg Gln Ala Ile Ser Pro
        1430                1435                1440

Ser Asp Arg Val Lys Leu Phe Pro His Arg Asn Ser Ser Lys Cys
        1445                1450                1455

Lys Ser Lys Pro Gln Ile Ala Ala Leu Lys Glu Glu Thr Glu Glu
        1460                1465                1470

Glu Val Gln Asp Thr Arg Leu
        1475                1480

<210> SEQ ID NO 2
<211> LENGTH: 1479
<212> TYPE: PRT
<213> ORGANISM: Homo sapiens

<400> SEQUENCE: 2

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140
```

```
Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Gly Val Ser Tyr Asp
            500                 505                 510

Glu Tyr Arg Tyr Arg Ser Val Ile Lys Ala Cys Gln Leu Glu Glu Asp
        515                 520                 525

Ile Ser Lys Phe Ala Glu Lys Asp Asn Ile Val Leu Gly Glu Gly Gly
    530                 535                 540

Ile Thr Leu Ser Gly Gly Gln Arg Ala Arg Ile Ser Leu Ala Arg Ala
545                 550                 555                 560

Val Tyr Lys Asp Ala Asp Leu Tyr Leu Leu Asp Ser Pro Phe Gly Tyr
```

```
                565                 570                 575
Leu Asp Val Leu Thr Glu Lys Glu Ile Phe Glu Ser Cys Val Cys Lys
            580                 585                 590

Leu Met Ala Asn Lys Thr Arg Ile Leu Val Thr Ser Lys Met Glu His
            595                 600                 605

Leu Lys Lys Ala Asp Lys Ile Leu Ile Leu His Glu Gly Ser Ser Tyr
            610                 615                 620

Phe Tyr Gly Thr Phe Ser Glu Leu Gln Asn Leu Gln Pro Asp Phe Ser
625                 630                 635                 640

Ser Lys Leu Met Gly Cys Asp Ser Phe Asp Gln Phe Ser Ala Glu Arg
                645                 650                 655

Arg Asn Ser Ile Leu Thr Glu Thr Leu His Arg Phe Ser Leu Glu Gly
                660                 665                 670

Asp Ala Pro Val Ser Trp Thr Glu Thr Lys Lys Gln Ser Phe Lys Gln
                675                 680                 685

Thr Gly Glu Phe Gly Glu Lys Arg Lys Asn Ser Ile Leu Asn Pro Ile
            690                 695                 700

Asn Ser Ile Arg Lys Phe Ser Ile Val Gln Lys Thr Pro Leu Gln Met
705                 710                 715                 720

Asn Gly Ile Glu Glu Asp Ser Asp Glu Pro Leu Glu Arg Arg Leu Ser
                725                 730                 735

Leu Val Pro Asp Ser Glu Gln Gly Glu Ala Ile Leu Pro Arg Ile Ser
                740                 745                 750

Val Ile Ser Thr Gly Pro Thr Leu Gln Ala Arg Arg Arg Gln Ser Val
            755                 760                 765

Leu Asn Leu Met Thr His Ser Val Asn Gln Gly Gln Asn Ile His Arg
            770                 775                 780

Lys Thr Thr Ala Ser Thr Arg Lys Val Ser Leu Ala Pro Gln Ala Asn
785                 790                 795                 800

Leu Thr Glu Leu Asp Ile Tyr Ser Arg Arg Leu Ser Gln Glu Thr Gly
                805                 810                 815

Leu Glu Ile Ser Glu Glu Ile Asn Glu Glu Asp Leu Lys Glu Cys Phe
                820                 825                 830

Phe Asp Asp Met Glu Ser Ile Pro Ala Val Thr Thr Trp Asn Thr Tyr
            835                 840                 845

Leu Arg Tyr Ile Thr Val His Lys Ser Leu Ile Phe Val Leu Ile Trp
            850                 855                 860

Cys Leu Val Ile Phe Leu Ala Glu Val Ala Ala Ser Leu Val Val Leu
865                 870                 875                 880

Trp Leu Leu Gly Asn Thr Pro Leu Gln Asp Lys Gly Asn Ser Thr His
                885                 890                 895

Ser Arg Asn Asn Ser Tyr Ala Val Ile Ile Thr Ser Thr Ser Ser Tyr
                900                 905                 910

Tyr Val Phe Tyr Ile Tyr Val Gly Val Ala Asp Thr Leu Leu Ala Met
            915                 920                 925

Gly Phe Phe Arg Gly Leu Pro Leu Val His Thr Leu Ile Thr Val Ser
            930                 935                 940

Lys Ile Leu His His Lys Met Leu His Ser Val Leu Gln Ala Pro Met
945                 950                 955                 960

Ser Thr Leu Asn Thr Leu Lys Ala Gly Gly Ile Leu Asn Arg Phe Ser
                965                 970                 975

Lys Asp Ile Ala Ile Leu Asp Asp Leu Leu Pro Leu Thr Ile Phe Asp
            980                 985                 990
```

```
Phe Ile Gln Leu Leu Leu Ile Val  Ile Gly Ala Ile Ala  Val Val Ala
        995              1000                1005

Val Leu Gln Pro Tyr Ile Phe  Val Ala Thr Val Pro  Val Ile Val
    1010            1015                1020

Ala Phe Ile Met Leu Arg Ala  Tyr Phe Leu Gln Thr  Ser Gln Gln
    1025            1030                1035

Leu Lys Gln Leu Glu Ser Glu  Gly Arg Ser Pro Ile  Phe Thr His
    1040            1045                1050

Leu Val Thr Ser Leu Lys Gly  Leu Trp Thr Leu Arg  Ala Phe Gly
    1055            1060                1065

Arg Gln Pro Tyr Phe Glu Thr  Leu Phe His Lys Ala  Leu Asn Leu
    1070            1075                1080

His Thr Ala Asn Trp Phe Leu  Tyr Leu Ser Thr Leu  Arg Trp Phe
    1085            1090                1095

Gln Met Arg Ile Glu Met Ile  Phe Val Ile Phe Phe  Ile Ala Val
    1100            1105                1110

Thr Phe Ile Ser Ile Leu Thr  Thr Gly Glu Gly Glu  Gly Arg Val
    1115            1120                1125

Gly Ile Ile Leu Thr Leu Ala  Met Asn Ile Met Ser  Thr Leu Gln
    1130            1135                1140

Trp Ala Val Asn Ser Ser Ile  Asp Val Asp Ser Leu  Met Arg Ser
    1145            1150                1155

Val Ser Arg Val Phe Lys Phe  Ile Asp Met Pro Thr  Glu Gly Lys
    1160            1165                1170

Pro Thr Lys Ser Thr Lys Pro  Tyr Lys Asn Gly Gln  Leu Ser Lys
    1175            1180                1185

Val Met Ile Ile Glu Asn Ser  His Val Lys Lys Asp  Asp Ile Trp
    1190            1195                1200

Pro Ser Gly Gly Gln Met Thr  Val Lys Asp Leu Thr  Ala Lys Tyr
    1205            1210                1215

Thr Glu Gly Gly Asn Ala Ile  Leu Glu Asn Ile Ser  Phe Ser Ile
    1220            1225                1230

Ser Pro Gly Gln Arg Val Gly  Leu Leu Gly Arg Thr  Gly Ser Gly
    1235            1240                1245

Lys Ser Thr Leu Leu Ser Ala  Phe Leu Arg Leu Leu  Asn Thr Glu
    1250            1255                1260

Gly Glu Ile Gln Ile Asp Gly  Val Ser Trp Asp Ser  Ile Thr Leu
    1265            1270                1275

Gln Gln Trp Arg Lys Ala Phe  Gly Val Ile Pro Gln  Lys Val Phe
    1280            1285                1290

Ile Phe Ser Gly Thr Phe Arg  Lys Asn Leu Asp Pro  Tyr Glu Gln
    1295            1300                1305

Trp Ser Asp Gln Glu Ile Trp  Lys Val Ala Asp Glu  Val Gly Leu
    1310            1315                1320

Arg Ser Val Ile Glu Gln Phe  Pro Gly Lys Leu Asp  Phe Val Leu
    1325            1330                1335

Val Asp Gly Gly Cys Val Leu  Ser His Gly His Lys  Gln Leu Met
    1340            1345                1350

Cys Leu Ala Arg Ser Val Leu  Ser Lys Ala Lys Ile  Leu Leu Leu
    1355            1360                1365

Asp Glu Pro Ser Ala His Leu  Asp Pro Val Thr Tyr  Gln Ile Ile
    1370            1375                1380
```

-continued

```
Arg Arg Thr Leu Lys Gln Ala Phe Ala Asp Cys Thr Val Ile Leu
    1385                1390                1395

Cys Glu His Arg Ile Glu Ala Met Leu Glu Cys Gln Gln Phe Leu
    1400                1405                1410

Val Ile Glu Glu Asn Lys Val Arg Gln Tyr Asp Ser Ile Gln Lys
    1415                1420                1425

Leu Leu Asn Glu Arg Ser Leu Phe Arg Gln Ala Ile Ser Pro Ser
    1430                1435                1440

Asp Arg Val Lys Leu Phe Pro His Arg Asn Ser Ser Lys Cys Lys
    1445                1450                1455

Ser Lys Pro Gln Ile Ala Ala Leu Lys Glu Glu Thr Glu Glu Glu
    1460                1465                1470

Val Gln Asp Thr Arg Leu
    1475
```